(12) United States Patent
Accili et al.

(10) Patent No.: US 9,309,514 B2
(45) Date of Patent: Apr. 12, 2016

(54) G PROTEIN-COUPLED PURINERGIC RECEPTOR GPR17 MEDIATES OREXIGENIC EFFECTS OF FOXO1 IN AGRP NEURONS

(71) Applicants: Domenico Accili, New York, NY (US); Hongxia Ren, New York, NY (US)

(72) Inventors: Domenico Accili, New York, NY (US); Hongxia Ren, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/374,977

(22) PCT Filed: Jan. 28, 2013

(86) PCT No.: PCT/US2013/023509
§ 371 (c)(1),
(2) Date: Jul. 28, 2014

(87) PCT Pub. No.: WO2013/113032
PCT Pub. Date: Aug. 1, 2013

(65) Prior Publication Data
US 2015/0087690 A1    Mar. 26, 2015

Related U.S. Application Data

(60) Provisional application No. 61/591,909, filed on Jan. 28, 2012, provisional application No. 61/646,544, filed on May 14, 2012.

(51) Int. Cl.
| | | |
|---|---|---|
| C07H 21/02 | (2006.01) | |
| C07H 21/04 | (2006.01) | |
| C12Q 1/68 | (2006.01) | |
| C12N 15/113 | (2010.01) | |
| A61K 31/557 | (2006.01) | |
| A61K 31/7072 | (2006.01) | |
| A61K 31/713 | (2006.01) | |
| A61K 45/06 | (2006.01) | |

(52) U.S. Cl.
CPC .......... *C12N 15/1138* (2013.01); *A61K 31/557* (2013.01); *A61K 31/7072* (2013.01); *A61K 31/713* (2013.01); *A61K 45/06* (2013.01); *C12N 2310/14* (2013.01); *C12N 2310/531* (2013.01)

(58) Field of Classification Search
CPC ........................... C12N 15/113; C12N 15/111
See application file for complete search history.

(56) References Cited

FOREIGN PATENT DOCUMENTS

WO      2005/040829      5/2005

OTHER PUBLICATIONS

ISA/USPTO, "International Search Report for PCT/US2013/023509", Jun. 26, 2013, Publisher: United States Patent & Trademark Office Receiving Office.
Ciana et al., The Orphan Receptor GPR17 Identified as a New Dual Uracil Nucleotides/Cysteinylleukotrienes Receptor, Oct. 4, 2006. vol. 25, No. 19, p. 4615-4627; Publisher: EMBO Journal; http://www.ncbi.nlm.nih.gov/pmc/articles/PMC1589991/.
Alaa Khaled Al-Helaili, Evidence for Involvement of the Cysteinyl Leukotriene Type 2 Receptor (CysLTsR) in the Regulation of Food Intake and Body Weight and Possible Role for Vagal Afferents; Jan. 2011, p. 1-65; Publisher: Queens University; http://qspace.library.queensu.ca/bitstream/1974/6333/1/Al-Helaili__Alaa__K__201101__MS.pdf.
Engel et al., Reduced Food Intake and Body Weight in Mice Deficient for the G. Protein-Coupled Receptor GPR82 Dec. 28, 2011; p. 1-13 Publisher: PLoS ONE; http://www.plosone.org/article/info%3Adoi%2F10.1371%2Fjournal.pone.0029400.

*Primary Examiner* — Amy Bowman
(74) *Attorney, Agent, or Firm* — Beusse Wolter Sanks & Maire PLLC; Judith A. Evans

(57) ABSTRACT

G protein-coupled receptor (GPCR) Gpr17 expressed in hypothalamic Agouti-related peptide-expressing (AgRP) neurons increases appetite and glucose tolerance and insulin sensitivity. By contrast, increasing Gpr17 reduced glucose tolerance and increased appetite. Gpr17-agonists had no effect on FoxO1-deficient mice, indicating, together with other data, that Gpr17 is a FoxO1 target. Certain embodiments are directed to methods for reducing appetite, increasing glucose tolerance and insulin sensitivity and treating diabetes by administering Gpr17 antagonists or inhibitory oligonucleotides. Appetite can be increased by administering Gpr17 agonists.

2 Claims, 34 Drawing Sheets

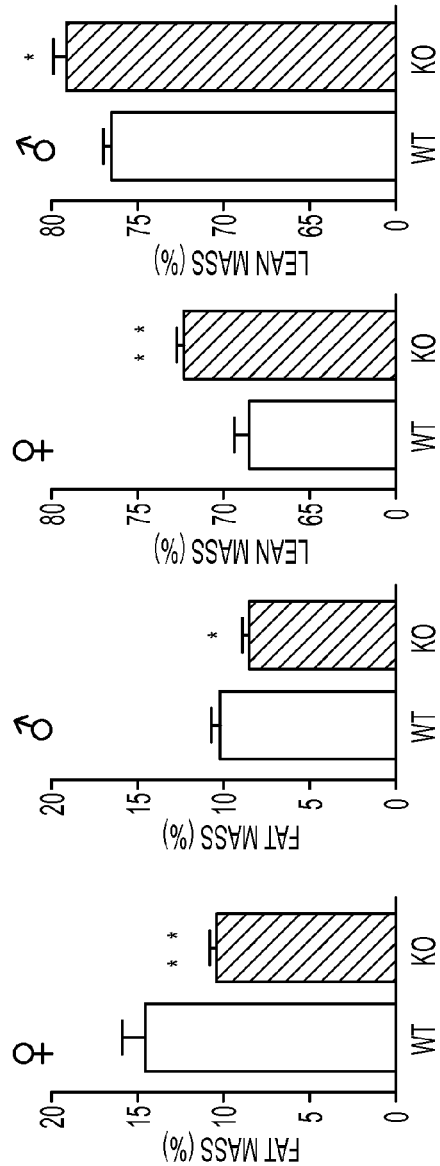
FIG. 1C
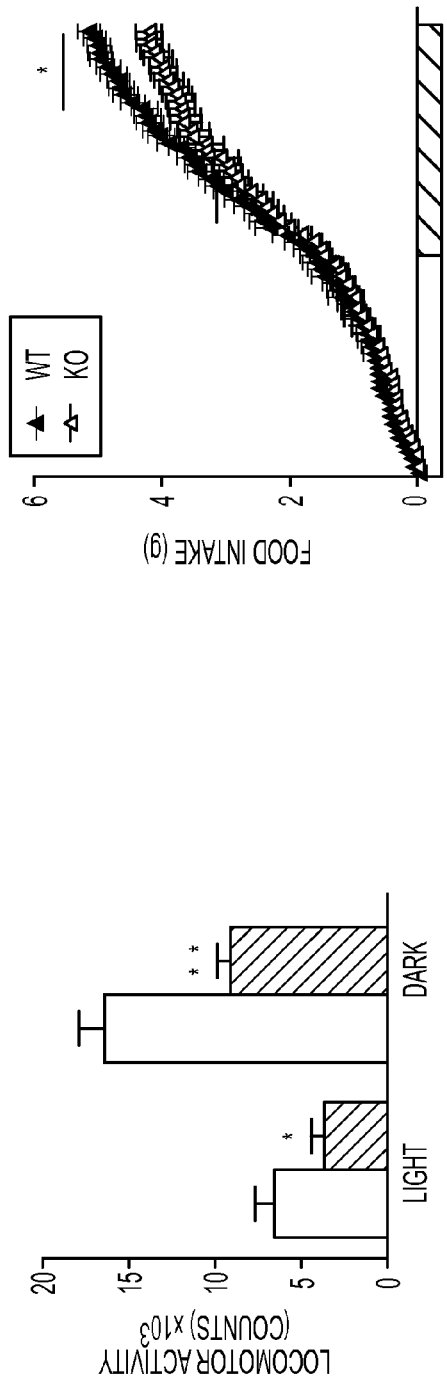
FIG. 1E
FIG. 1D

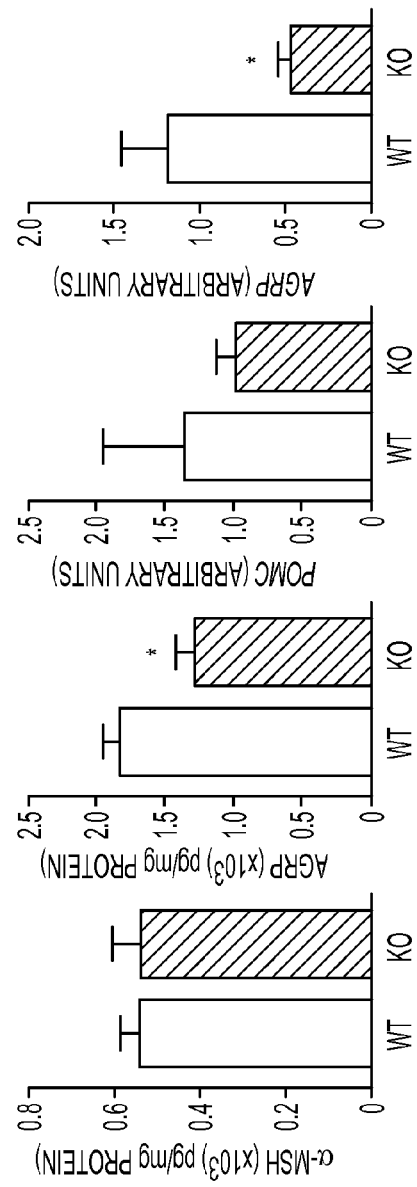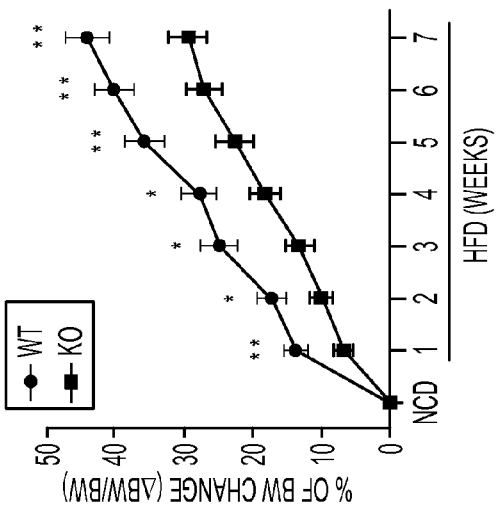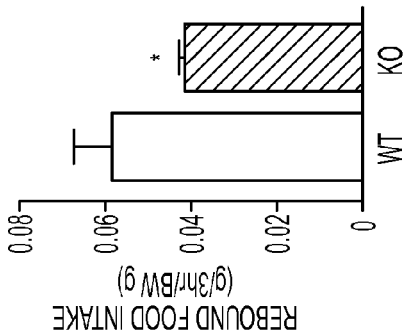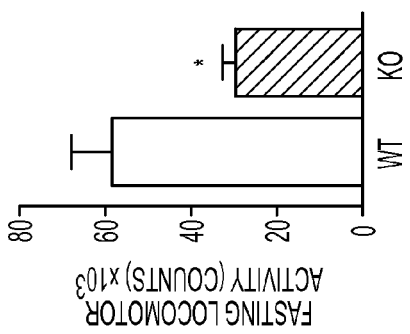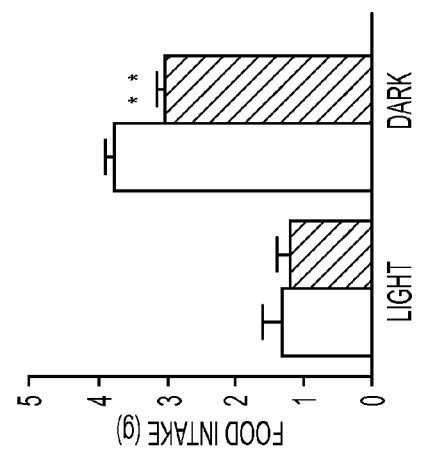

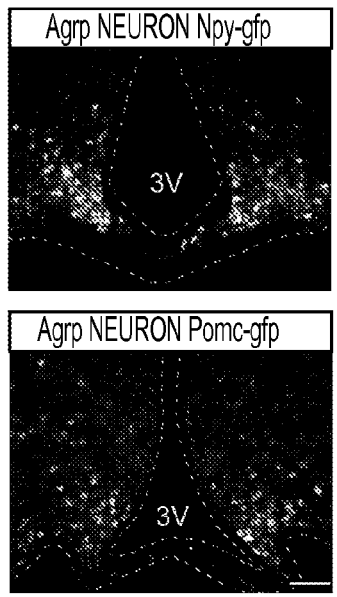
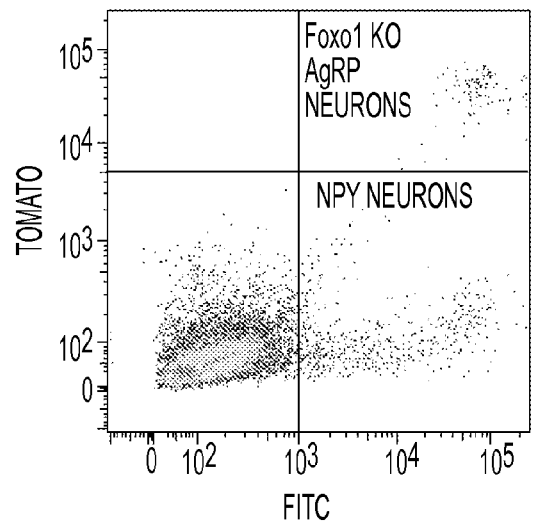
FIG. 5A
FIG. 5B
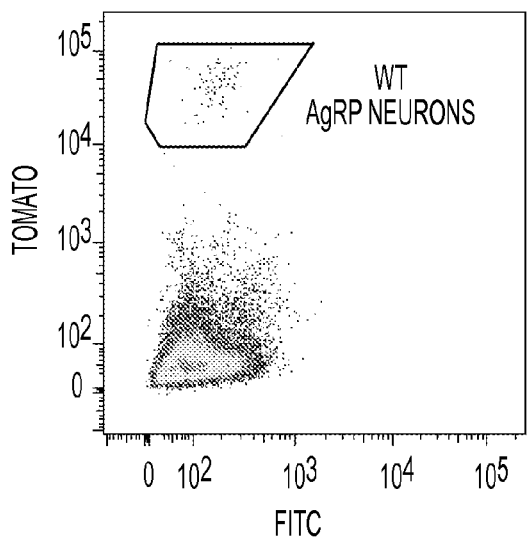
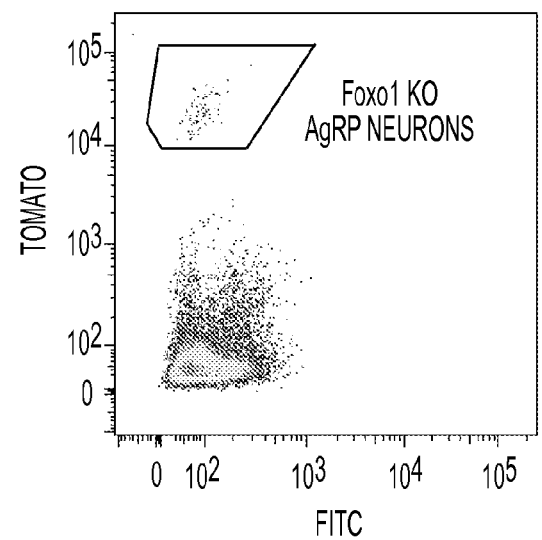
FIG. 5C

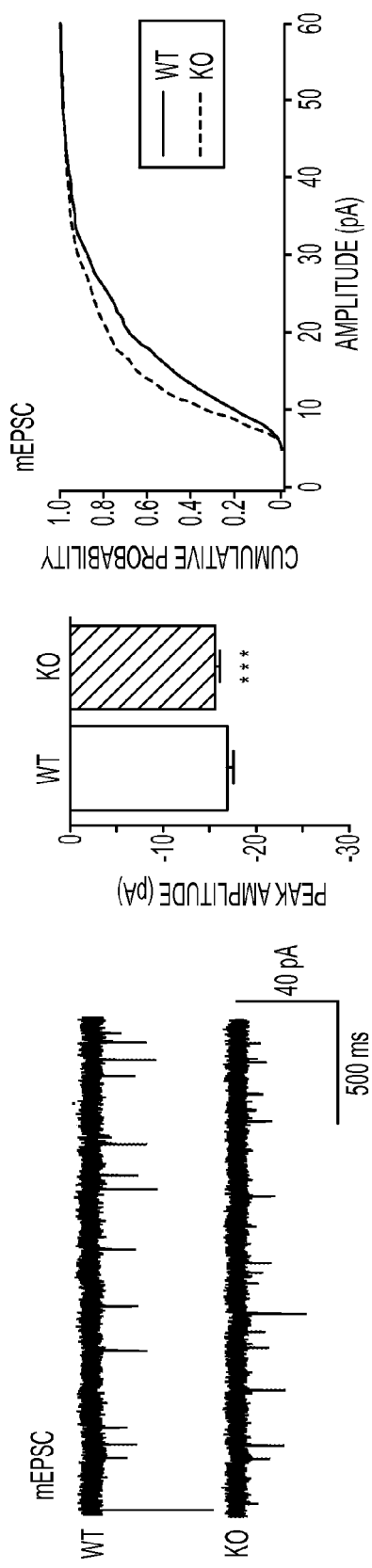
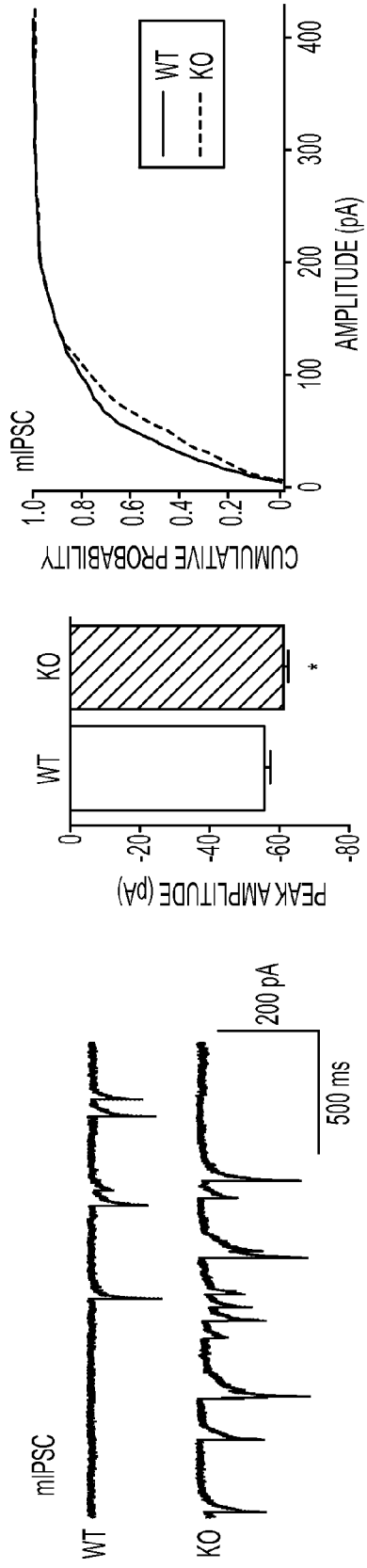
FIG. 5G
FIG. 5H

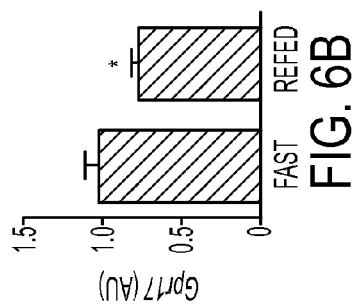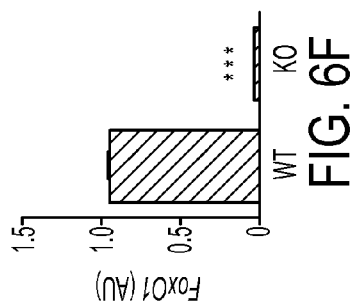
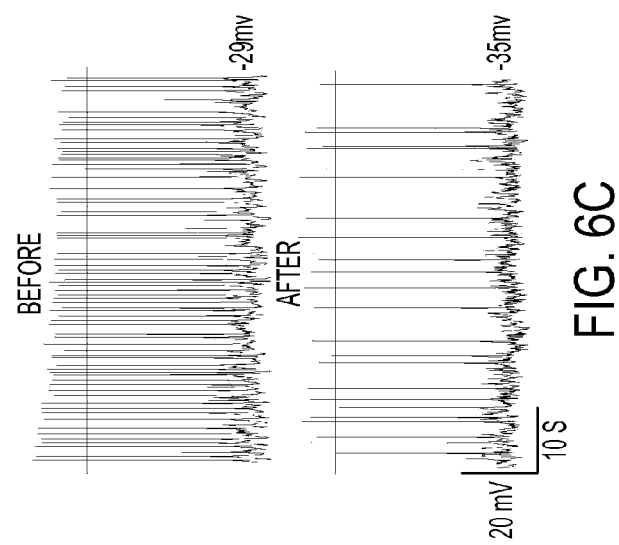
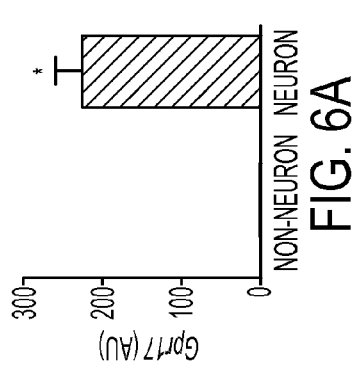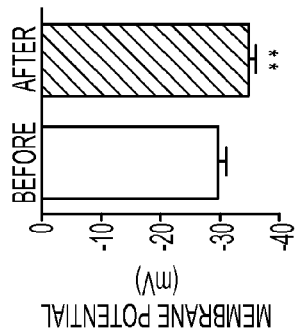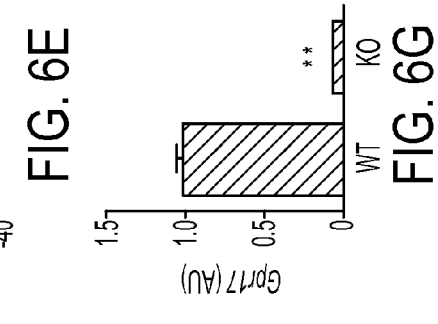
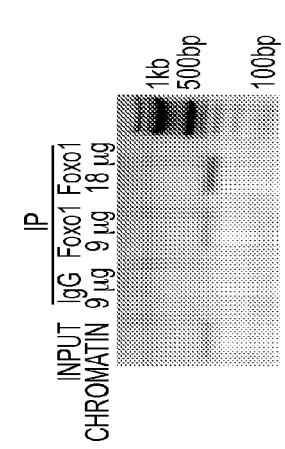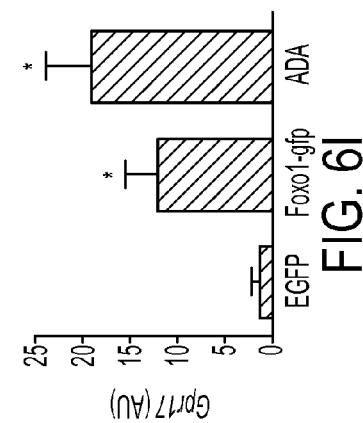

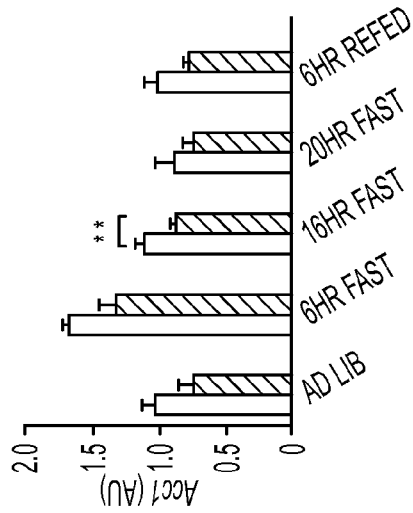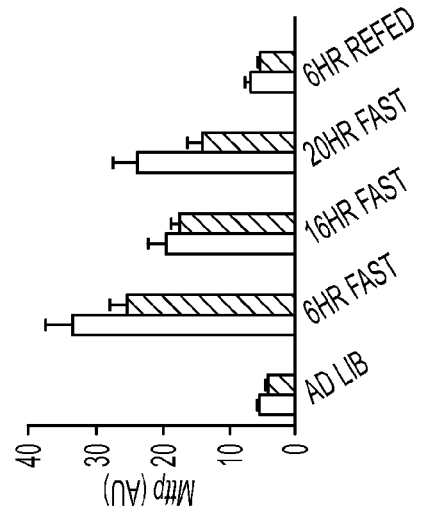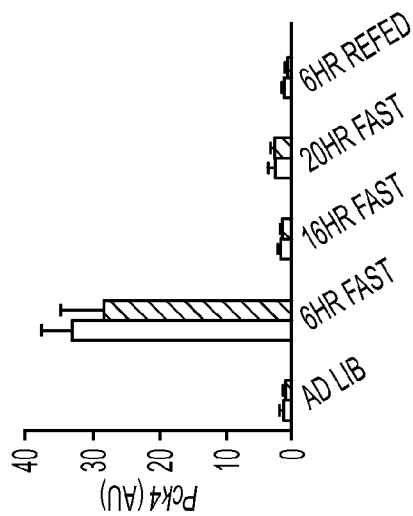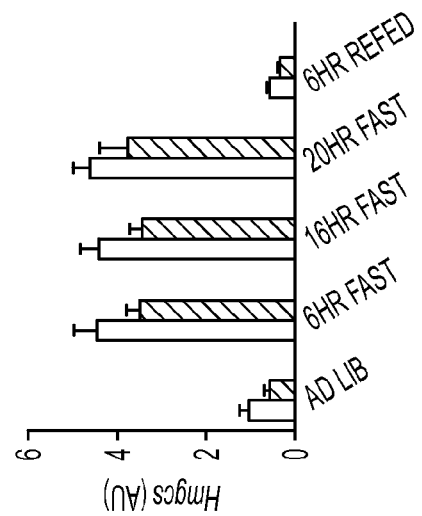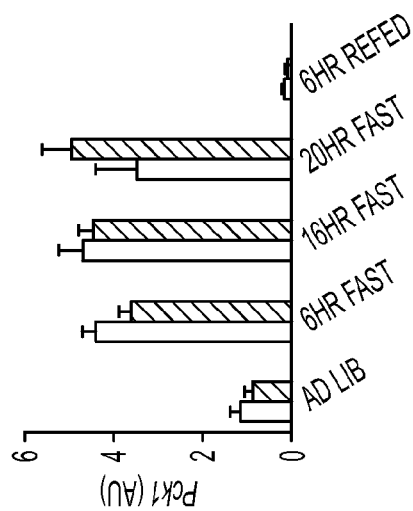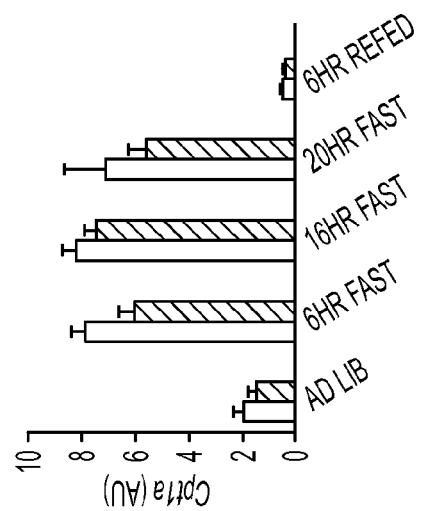

A) Gfp TRANSFECTED;
B) Gpr17-Gfp TRANSFECTED;

G PROTEIN-COUPLED PURINERGIC RECEPTOR GPR17 MEDIATES OREXIGENIC EFFECTS OF FOXO1 IN AGRP NEURONS

CROSS-REFERENCE TO RELATED APPLICATIONS

This application is a 371 national stage application of PCT Application No. PCT/US2013/023509, filed Jan. 28, 2013, and claims the benefit of U.S. Application No. 61/591,909 filed Jan. 28, 2012, and U.S. Application No. 61/646,544 filed May 14, 2012, the entire contents of which are hereby incorporated by reference as if fully set forth herein.

STATEMENT OF GOVERNMENTAL INTEREST

This invention was made with government support under National Institutes of Health Grant DK57539. The government has certain rights in the invention.

BACKGROUND

The prevalence of obesity has grown at alarming rates, reaching pandemic proportions. One third of U.S. adults are obese, leading to increased numbers of patients affected by the comorbidities of obesity, such as cardiovascular disease, type 2 diabetes, respiratory disorders and cancer (Wang et al., 2011). Considering the staggering cost and serious challenges to public health associated with this condition, identification of biochemical pathways that can be effectively and safely targeted for obesity therapy has acquired new urgency.

Hypothalamic neurons expressing agouti-related protein (AgRP) have been directly implicated in promoting feeding. AgRP neuron activation by either light-gated Channelrhodopsin-2 or ligand-activated G-proteins rapidly increases food intake (Aponte et al., 2011; Krashes et al., 2011). Conversely, acute ablation of AgRP neurons in adulthood causes cessation of feeding and results in starvation (Luquet et al., 2005). Despite the established functional importance of AgRP neurons in feeding behavior, genetic analyses of specific hormonal pathways that impinge on this process have yielded limited and occasionally conflicting results. For example, transgenic overexpression of AgRP results in obesity, and acute intracerebroventricular delivery of AgRP or Neuropeptide Y (Npy), another peptide produced in AgRP neurons, elicits hyperphagia (Levine et al., 2004; Ollmann et al., 1997; Rossi et al., 1998). However, mice with loss of AgRP, Npy, or both exhibit no feeding or body weight phenotypes and maintain a normal response to starvation (Qian et al., 2002).

The key anorexigenic hormones, insulin and leptin, inhibit AgRP neurons, raising their activation threshold (Konner et al., 2007; Takahashi and Cone, 2005). Surprisingly though, genetic ablation of insulin receptor in AgRP neurons has no effect on energy homeostasis, even though it impairs insulin-mediated suppression of hepatic glucose production (Konner et al., 2007). Similarly, inactivation of leptin receptors in AgRP neurons results in a mild increase of weight, without affecting feeding behavior and energy balance (van de Wall et al., 2008). Thus, neither pathway appears to exert obligate control over AgRP neuron-dependent feeding and energy homeostasis. There is a need to solve the apparent paradox of the absence of food intake abnormalities following ablation of leptin or insulin receptors, and to identify alternative pathways that regulate AgRP neuron-dependent food intake.

SUMMARY OF THE INVENTION

A first set of embodiments of the invention is directed to methods of treating or preventing obesity in a subject by administering an agent that reduces Gpr17 expression or biological activity (such as a Gpr17 antagonist or inhibitory oligonucleotide) to the subject in need of such treatment in therapeutically or prophylactically effective amounts that reduce the subjects appetite thereby treating the obesity. Inhibitory oligonucleotides include but are not limited to siRNAs, shRNAs and antisense oligonucleotides that block the expression of Gpr17. In an embodiment, a combination of at least one Gp17 purinergic antagonist and at least one cysteinyl-leukotriene (cysLT) antagonist are administered either simultaneously or at different times.

A second set of embodiments is directed to methods for increasing glucose tolerance and/or insulin sensitivity in a subject having impaired glucose tolerance or abnormally low insulin sensitivity by administering an agent that reduces Gpr17 expression or biological activity (such as a Gpr17 antagonist or inhibitory oligonucleotide) to the subject in an amount that increases glucose tolerance and/or insulin sensitivity. A related embodiment is directed to a method for treating diabetes in a subject by administering an agent that reduces Gpr17 expression or biological activity (such as a Gpr17 antagonist or inhibitory oligonucleotide) to the subject in an amount that increases glucose tolerance and/or insulin sensitivity, thereby treating the diabetes. Ren, Hongxia et al., *Cell* 149 (6): 1314-1326.

A third set of embodiments is directed to methods for treating anorexia (or increasing appetite) by administering therapeutically or prophylactically effective amounts of a Gpr17 agonist to a subject in need of such treatment thereby treating the anorexia or increasing the appetite. Gpr17 agonists include those identified herein. In an embodiment, anorexia or other eating disorder associated with weight loss and loss of appetite, is treated by administering therapeutically- or prophylactically-effective amounts of a combination of at least one Gp17 purinergic agonist such as a uracil nucleotide (UDP, UDP-glucose, and UDP-galactose; Jacobson and Boeynaems, 2010) and at least one cysteinyl-leukotriene (cysLT) agonist (such as LTC4, LTD4, and LTE4). These agonists can be administered simultaneously or separately.

A fourth set of embodiments, is directed to pharmaceutical formulations comprising at least one purinergic agonist such as a uracil nucleotide and at least one cysteinyl-leukotriene (cysLT) agonist (such as LTC4, LTD4, and LTE4) in amounts that increase appetite and/or food intake. Other formulations comprise at least one purinergic antagonist and at least one cysteinyl-leukotriene antagonist in amounts that decrease appetite and/or food intake or glucose tolerance.

A fifth set of embodiments is directed to cell-based screening methods for identifying Gpr17 agonists and antagonists.

BRIEF DESCRIPTION OF THE FIGURES

FIG. 1A-1J. Generation and analysis of Agrp-Foxo1$^{-/-}$ mice. (A) Immunohistochemistry of ARH in wild-type (WT) and Agrp-Foxo1$^{-/-}$ mice (KO) using Rfp as a reporter of Cre-mediated recombination (red) and Foxo1 (green) to determine co-localization and DAPI to counterstain nuclei (blue). Scale bar 50 µm. (B) Growth curves of female and male WT and KO on chow diet. (C) Body fat and lean mass content in female (n=12-13 for each genotype) and male (n=6 for each genotype) mice analyzed by MRI. (D) Locomotor activity in light and dark phase (n=5-8 for each genotype). (E-F) Cumulative 24-h (E) and dark phase food intake (F) (g of food per mouse) (n=5-8 for each genotype). (G) Locomotor activity during overnight fasting (n=5 for each genotype). (H) Rebound food intake (g/g lean body mass) after an overnight fast (n=9 for each genotype). (I) Hypothalamic neuropeptide (aMSH and AGRP) levels after overnight fast (n=5-6 for each genotype). Agrp and Pomc mRNA in ARH after overnight fast (n=6 for each genotype). (J) Percentage of body weight gain of 10 wk-old mice after switching to HFD (n=8-9). Data presented as means±SEM. *=P<0.05, **=P<0.01.

FIG. 5A-5H. FACS, RNA profiling and electrophysiology of AgRP neurons. (A) Fluorescence microscopy of ARH from Agrp-Foxo1$^{-/-}$; Rosa-tomato mice carrying a Npy-Gfp or Pomc-Gfp transgene. Foxo1-deficient AgRP neurons (red) retain Npy-Gfp expression (green, upper panel), giving rise to merged yellow color (upper panel), whereas they fail to co-localize with Pomc-Gfp (green, lower panel). Scale bar 100 µm. (B) FACS analysis of dissociated hypothalamic neurons of Agrp-Foxo1$^{-/-}$ mice carrying a Npy-Gfp transgene (Agrp-Foxo1$^{-/-}$; Rosa-tomato; Npy-Gfp). Npy neurons were sorted by green fluorescence (FITC, horizontal axis) and AgRP neurons were identified by red fluorescence (Tomato, vertical axis). (C) Representative FACS analysis of dissociated hypothalamic neurons of Agrp-Foxo1$^{-/-}$; Rosa-tomato mice and Agrp-Foxo1$^{-/loxP}$; Rosa-tomato mice. (D-F) Representative traces recorded in AgRP neurons from WT and Agrp-Foxo1$^{-/-}$ mice (D). Quantified results: firing frequency normalized to WT without insulin treatment (E), membrane potential (F). WT–insulin n=6, WT+insulin n=10, KO–insulin n=11, KO+insulin n=4. (G,H) mEPSC (G) and mIPSC (H) recorded in AgRP neurons from WT and Agrp-Foxo1$^{-/-}$ mice illustrating representative traces (left), peak amplitude (middle) and size distribution (right) (mEPSC n=30, and mIPSC n=27-29 for each genotype). Data presented as means±SEM. *=P<0.05, =P<0.01, *=P<0.001.

FIG. 6A-6I. G protein-coupled receptor Gpr17 is a Foxo1 target in AgRP neurons. (A) Gpr17 mRNA levels in flow-sorted neurons and non-neurons (identified using Synapsin-Cre; Rosa-tomato mice) (n=2 for each genotype). (B) Gpr17 mRNA in mediobasal hypothalamus from overnight-fasted and refed mice (n=7 for each genotype). (C-E) Representative traces of electrophysiological recordings from the same AgRP neurons before and after cangrelor treatment (90 nM) (C). Quantified results: firing frequency normalized to the values before cangrelor treatment (D) and membrane potential (E). (N=9) (F,G) Foxo1 (F) and Gpr17 (G) expression in flow-sorted AgRP neurons from WT and KO mice (n=3 for each genotype). (H) ChIP assay of the Gpr17 promoter in Neuro2A cells transfected with constitutively nuclear Foxo1. (I) Endogenous Gpr17 mRNA in Neuro2A cells transfected with GFP-tagged wild-type Foxo1 (Foxo1-gfp) or constitutively nuclear Foxo1 (ADA) (n=3 for each genotype). Data presented as means±SEM. *=P<0.05, =P<0.01, *=P<0.001.

FIG. 10A-10F. Additional liver gene expression. Expression of Pck1 (A), Pdk4 (B), Acc1 (C), Cpt1a (D), Hmgcs (E), and Mttp (F) in livers of Agrp-Foxo1–/– (KO) and wild-type mice (WT) under the following conditions: ad libitum-fed (WT n=5, KO n=4), 6-hr fast (WT n=7, KO n=10), 16-hr fast (WT n=7, KO n=9), 20-hr fast (WT n=6, KO n=6), 6-hr refed (WT n=8, KO n=7). Data presented as means±SEM.

DETAILED DESCRIPTION

Figure 1A:
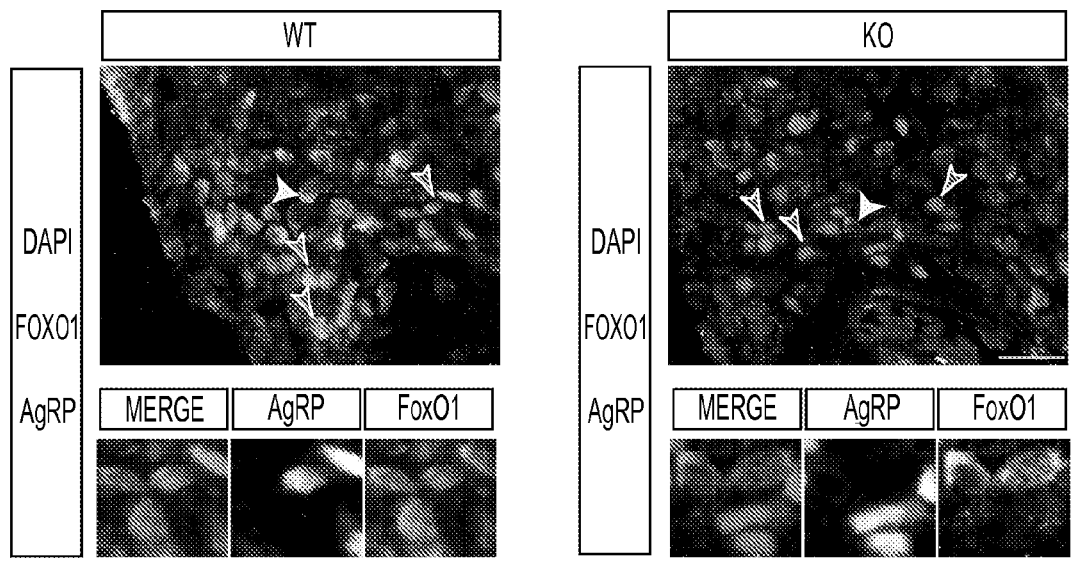

There is a need to identify new pathways involved in appetite and weight control to treat not only obesity but also eating disorders such as anorexia. There is also a need for new treatments for diabetes, types 1 or 2. It is known that hypothalamic neurons expressing Agouti-related peptide (AgRP) are critical for initiating food intake, and inhibition of Ag neurons has anorexigenic effects. However, genetic ablation of anorexigenic signaling by insulin or leptin in AgRP neurons failed to affect food intake. It has now been discovered that the G protein-coupled receptor (GPCR) Gpr17 expressed in hypothalamic Agouti-related peptide-expressing (AgRP) neurons increases appetite and reduces both glucose tolerance and insulin sensitivity through the FoxO1 pathway. By contrast, increasing Gpr17 caused a reduction in glucose tolerance and increased appetite. Ren, Hongxia; et al., *Cell* 149 (6): 1314-1326. Gpr17-agonists had no effect on FoxO1-deficient mice, indicating, together with other data presented here, that Gpr17 is a FoxO1 target.

1. DEFINITIONS

"Anorexia nervosa" is an eating disorder characterized by immoderate food restriction and irrational fear of gaining weight, as well as a distorted body self-perception. It typically involves excessive weight loss and is usually found more in females than in males. Anorexia nervosa, and the associated malnutrition that results from self-imposed starvation, can cause severe complications in every major organ system in the body.

"Impaired glucose tolerance (IGT)" means a pre-diabetic state of hyperglycemia that is associated with insulin resistance and increased risk of cardiovascular pathology. IGT may precede type 2 diabetes mellitus by many years. IGT is also a risk factor for mortality. Barr E L, et al. (2007). *Circulation* 116 (2): 151-7. According to the criteria of the World Health Organization and the American Diabetes Association, impaired glucose tolerance is defined as: two-hour glucose levels of 140 to 199 mg per dL (7.8 to 11.0 mmol) on the 75-g oral glucose tolerance test. A patient is said to be under the condition of IGT when he/she has an intermediately raised glucose level after 2 hours, but less than would qualify for type 2 diabetes mellitus. The fasting glucose may be either normal or mildly elevated. World Health Organization, Definition, diagnosis and classification of diabetes mellitus and its complications: Report of a WHO Consultation. Part 1. Diagnosis and classification of diabetes mellitus; American Diabetes, Association (2005). "*Diabetes Care* 28 Suppl 1: S37-42. From 10 to 15 percent of adults in the United States have impaired glucose tolerance or impaired fasting glucose.

"Preventing a disease" includes, but is not limited to, preventing the disease from occurring in a subject that may be predisposed to the disease (or disorder), but has not yet been diagnosed as having the disease; inhibiting the disease, for example, arresting the development of the disease; relieving the disease, for example by causing its regression; relieving the condition caused by the disease, for example by reducing its symptoms, and/or delaying disease onset. An example is reducing blood glucose levels in a hyperglycemic subject, and/or maintaining acceptable control of blood glucose levels in the subject. Such treatment, prevention, symptoms and/or conditions can be determined by one skilled in the art and are described in standard textbooks.

"Treating" a disease, disorder or condition in a patient means taking steps to obtain beneficial or desired results, including clinical results. For purposes of this invention, beneficial or desired clinical results include, but are not limited to alleviation or amelioration of one or more symptoms of the disease; diminishing the extent of disease; delaying or slowing disease progression; amelioration and palliation or stabilization of the disease state.

"Type 1 diabetes" may be diagnosed by methods well known to one of ordinary skill in the art. For example, commonly, diabetics have a plasma of fasting blood glucose result of greater than 126 mg/dL of glucose. Diabetes type 1 symptoms include frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections. These symptoms are associated with characteristic clinical laboratory findings that include hyperglycemia, loss of glycemic control (i.e., frequent and excessive swings of blood sugar levels above and below the physiological range, generally maintained between 40-125 mg/dl), fluctuations in postprandial blood glucose, fluctuations in blood glucagon, fluctuations in blood triglycerides and include reduction in rate of or diminution of or improved outcomes of conditions that are accelerated by and/or occur because of or more frequently with diabetes including microvascular and microvascular disease.

"Prediabetes" means a condition that is commonly diagnosed in patients with a blood glucose level between 100 and 125 mg/dL of glucose.

"Reduction" of a symptom(s) means decreasing of the severity or frequency of the symptom(s), or elimination of the symptom(s).

"Administering" or "administration of" a drug or therapeutic pharmaceutical composition to a subject means using any method known in the art including both direct administration, including self-administration (including oral administration or intravenous, subcutaneous, intramuscular or intraperitoneal injections, rectal administration by way of suppositories), local administration directly into or onto a target or administration by any route or method that delivers a therapeutically effective amount of the drug or composition to the cells or tissue to which it is targeted.

A "subject" or "patient" means a mammal, typically a human, but optionally a mammalian animal of veterinary importance, including but not limited to horses, cattle, sheep, dogs, and cats.

A "therapeutically effective amount" of an active agent or pharmaceutical composition means an amount that achieves the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

A "prophylactically effective amount" of a drug means an amount of a drug that, when administered to a subject, will have the intended prophylactic effect, e.g., preventing or delaying the onset (or reoccurrence) of the disease or symptoms, or reducing the likelihood of the onset (or reoccurrence) of the disease or symptoms. The full prophylactic effect does not necessarily occur by administration of one dose and may occur only after administration of a series of doses. Thus, a prophylactically effective amount may be administered in one or more administrations. For diabetes, a therapeutically effective amount can also be an amount that increases insulin secretion, increases insulin sensitivity, increases glucose tolerance, or decreases weight gain, weight loss, or fat mass.

An "effective amount" of an agent means an amount that produces the desired effect.

By "pharmaceutically acceptable," it means meant the carrier, diluent or excipient must be compatible with the other ingredients of the formulation and not deleterious to the recipient thereof.

Administration of an agent "in combination with" includes parallel administration of two agents to the patient over a period of time, co-administration (in which the agents are administered at approximately the same time, e.g., within about a few minutes to a few hours of one another), and co-formulation (in which the agents are combined or compounded into a single dosage form suitable for oral, subcutaneous or parenteral administration).

2. OVERVIEW

Gpr17 is a G protein-coupled receptor (GPCR). Gpr17 is a uracil nucleotide/cysteinyl leukotriene receptor is a protein that in humans is encoded by the GPR17 gene. G protein-coupled receptor 17, GPR17, also known as uracil nucleotide/cysteinyl leukotriene receptor or P2Y-like receptor (P2YL), is a 367 amino acid member of the G-protein coupled receptor family of proteins. While GPR17 is expressed in kidney, heart and umbilical vein endothelial cells, it is expressed in the highest levels in the brain. Activation of GPR17 by UDP-glucose induced a partial heterologous desensitization of LTD4-mediated responses, suggesting that nucleotides have a hierarchy in producing desensitizing signals. Gpr17 is also referred to as Uracil nucleotide/cysteinyl leukotriene receptor, UDP/CysLT receptor, P2Y-like receptor, R'1, and AI853548. Gpr17 is a P2Y-like receptor that responds to both uracil nucleotides (as UDP-glucose) and cysteinyl-leukotrienes (cysLTs, as LTD4).

Gpr17 has been deorphanized as a dual receptor for uracil nucleotides and cysteinyl-leukotrienes (Ciana et al., 2006). Inhibition of Gpr17 in vivo can reduce ischemic damage in rodents, presumably by lowering neuronal excitability (Ciana et al., 2006). In addition, purinergic receptors, including Gpr17, have been widely reported to modulate $Ca^{2+}$ and $K^+$ channels and neurotransmitter receptors (Fischer and Krugel, 2007; Pugliese et al., 2009). But neither the role of Gpr17 in satiety and glucose homeostasis, nor its CNS distribution is known (Chen et al., 2009; Lecca et al., 2008). To examine the latter point, neurons were labeled with Rfp by intercrossing Synapsin-Cre and Rosa-tomato mice, then flow-sorted neuron and non-neuron populations and measured Gpr17 levels. qPCR analysis showed that Gpr17 is overwhelmingly enriched in neurons (FIG. 6A).

It has been reported that inhibition of Gpr17 by either antagonist ligands or using antisense technology in an animal ischemia model markedly reduced brain damage. Abbracchio, United States Patent Application 20090156521 (herein Abbracchio). Abbracchio tested the Gpr17 antagonists montelukast and AR-C69931MX. Further described in Abbracchio are methods of administering and preparing pharmaceutical formulations of Gpr17-receptor antagonists and antisense oligonucleotides for therapeutic use. Antisense nucleotides that block expression of Gpr17 were successfully administered in vivo in Abbracchio to control ischemia including those identified in 20090156521 as SEQ ID NO: 1 and SEQ ID NO: 2 (shown below). These antisense oligonucleotides can also be administered in certain embodiments of the present invention where it is desired to inhibit Gpr17, such as methods for treating obesity or methods for increasing glucose tolerance. Seven specific new siRNA molecules (SEQ ID NOS. 3-9) were made and used to reduce Gpr17 expression in the experiments described here. These seven siRNAs are identified below and also have therapeutic utility in treating obesity and diabetes.

Foxo1 (herein also "FoxO") is a shared mediator of both of these pathways, and its inhibition is required for their anorexigenic effects. Transcription (Kim et al., 2006; Kitamura et al., 2006). In order to create a metabolic and energy balanced phenotype that recapitulated constitutive insulin and leptin signaling in Ag neurons, FoxO neurons were ablated and experiments were designed to identify Foxo1 targets that are involved in appetite and weight regulation.

3. SUMMARY OF RESULTS

1) Agrp-Foxo1$^{-/-}$ mice were generated. Foxo1 was highly expressed in ARH neurons, including AgRP neurons, of wild-type mice, but was selectively undetectable in AgRP neurons of Agrp-Foxo1$^{-/-}$ mice.

2) Improved energy homeostasis was observed in Agrp-Foxo1$^{-/-}$ mice. Both female and male Agrp-Foxo1$^{-/-}$ mice showed altered body composition, with a remarkable 18-30% decrease of fat mass and a significant 3-5% increase of lean mass.

3) Altered hepatic glucose production and gene expression were seen in Agrp-Foxo1$^{-/-}$ mice, including elevated fasting plasma FFA and glycerol, and smaller fat cells having larger mitochondria of normal morphology were seen in the epididymal white adipose tissue (EWAT).

4) Knocking out Foxo1 in AgRP neurons rendered mice more sensitive to leptin and insulin signaling in the hypothalamus, and increased pS6 staining in ARH and DMH was seen.

5) Gene set enrichment analysis of microarray data demonstrated increased expression of genes encoding components of the electron transport chain, translation, generation of precursor metabolites and energy, mitochondrial genome maintenance, and cellular component biogenesis in Foxo1-deficient AgRP neurons which is consistent with a state of increased energy availability.

6) Electrophysiological profiles indicate that Agrp-Foxo1$^{-/-}$ neurons have heightened insulin-sensitivity such that even when with significantly lower membrane potential and firing frequency, insulin still caused a 100-fold reduction in the basal firing rate of Agrp-Foxo1$^{-/-}$ neurons compared to a threefold reduction in wild type neurons.

7) Foxo1 ablation in AgRP neurons led to increased GABAergic and decreased glutaminergic responses, indicating altered neurotransmitter receptor expression at the post-synaptic level.

8) mRNA encoding the G protein-coupled receptor, Gpr17, was profoundly decreased in flow-sorted Foxo1-deficient AgRP neurons.

9) Gpr17 antagonist, cangrelor, produced significantly reduced firing frequency and lower membrane potential in AgRP neurons in wild type mice.

10) Foxo1 binds to the Gpr17 promoter, and transfection of either wild-type Foxo1-Gfp or constitutively active Foxo1 significantly increased Gpr17 levels.

11) Gpr17 antagonism directly and specifically increased pSTAT3 content (a measurement of leptin signaling) in wild type AgRP neurons in vivo.

12) Activating Gpr17 rapidly induced food intake in wild type, but not in Agrp-Foxo1$^{-/-}$ mice showing that Gpr17 is a direct Foxo1 target, and that its decreased expression mediates—at least partly—the anorexigenic phenotype of Agrp-Foxo1$^{-/-}$ mice.

Figure 13A:
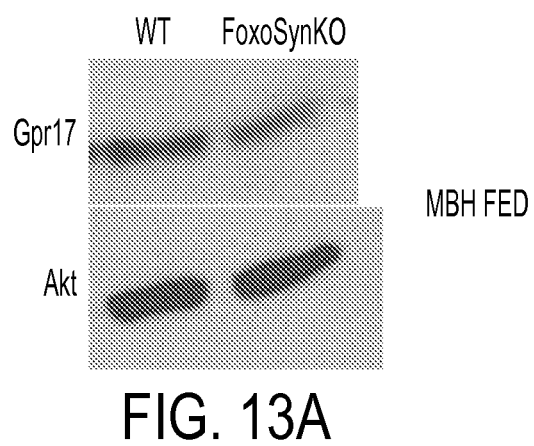
FIG. 13A-B. In vivo regulation of Gpr17 expression. (A) FoxO regulates Gpr17 expression in vivo. Mediobasal hypothalamus (MBH) extracts from wild type and FoxO-SynCre-KO mice were processed. Gpr17 was detected by western blot. Knocking out FoxO in MBH causes a concomitant reduction of Gpr17. (B) Gpr17 expression is elevated in insulin resistant diabetic GIRKO mice by western blot.
Figure 13B:
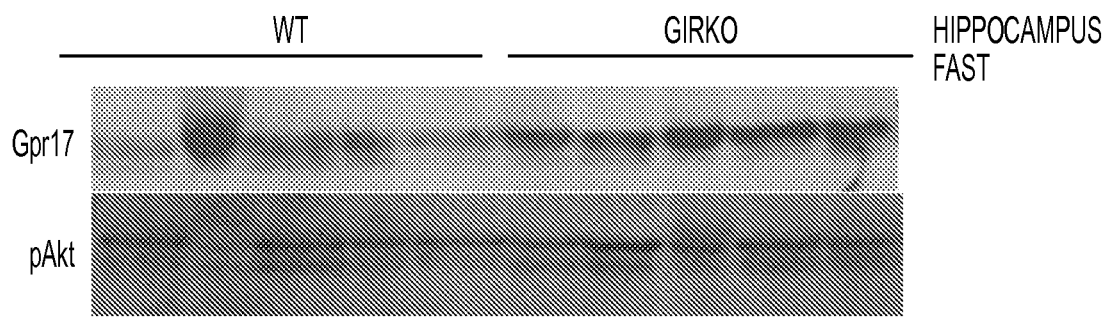

13) Knocking out FoxO in the medio basal hypothalamus (MBH) of wild type mice caused a concomitant reduction of Gpr17, showing that Gpr17 is an endogenous target of FoxO. Moreover, Gpr17 expression was elevated in insulin resistant diabetic GIRKO mice. FIG. 13.

Figure 14:
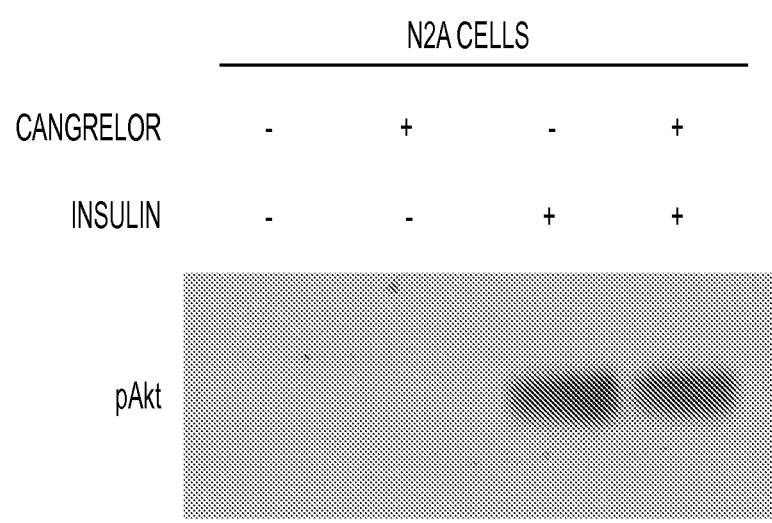
FIG. 14. Neuro2A (N2A) cells are a suitable model for studying the molecular mechanisms of Gpr17 signaling. Wild type N2A cells (treated with or without cangrelor) were serum starved overnight and stimulated with insulin. Insulin signaling activity was gauged by measuring pAkt by western blot. N2A cells express minimal endogenous Gpr17. Antagonizing Gpr17 has minimal effect on insulin signaling in wild type N2A cells.
Figure 15:
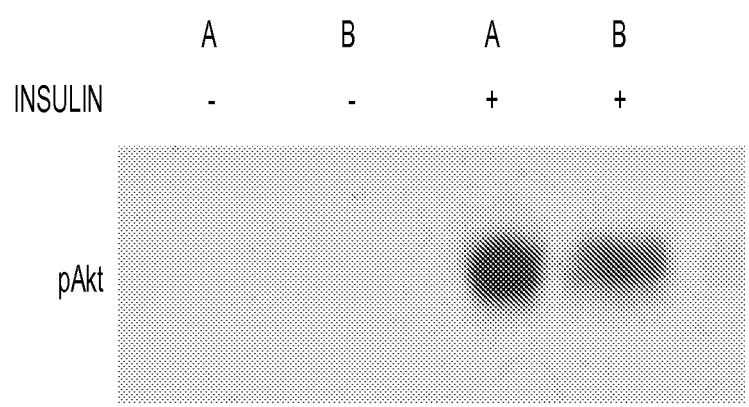
FIG. 15. Gpr17 reduces insulin signaling in N2A cells. N2A cells were transfected with control or Gpr17-Gfp construct. Insulin signaling activity was measured by pAkt western blot. N2A cells transfected with Gpr17-Gfp have reduced pAkt in response to insulin stimulation, suggesting Gpr17 directly antagonizes insulin signaling.

14) Antagonizing Gpr17 in N2A cells that express minimal endogenous Gpr17 had minimal effect on insulin signaling in wild type N2A cells. Mice were engineered to overexpress Gpr17 in N2A cells to show that overexpression of Gpr17 reduced insulin signaling. FIG. 14 and FIG. 15.

15) Gpr17 overexpression reduced leptin signaling in N2A cells as was detected by reduced pSTAT3 in response to leptin stimulation. FIGS. 4 and 5.

16) Insulin-induced pAkt was visualized by staining (green fluorescence), and Gpr17-mCherry overexpressing cells were identified by red fluorescence. Ten minutes after insulin treatment, Gpr17-mCherry cells have less plasma membrane localized pAkt compared with wild type cells. 30 minutes after insulin treatment, as expected, pAkt staining decayed in both Gpr17-mCherry and wild type cells, thus confirming pAkt staining as a valid way of measuring insulin-induced Akt activity. FIG. 7.

Figure 8A:
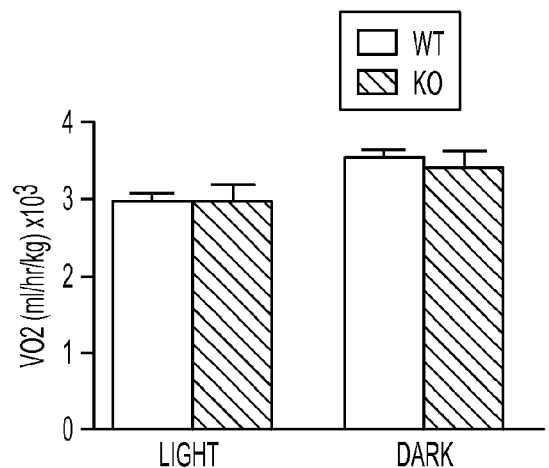
FIG. 8A-8C. Indirect calorimetry analysis of Agrp-Foxo1–/– mice. (A) oxygen consumption (VO2), (B) respiratory quotient (RQ), and (C) energy expenditure (normalized to lean body mass) (n=5-8 for each genotype). Data presented as means±SEM.
Figure 8B:
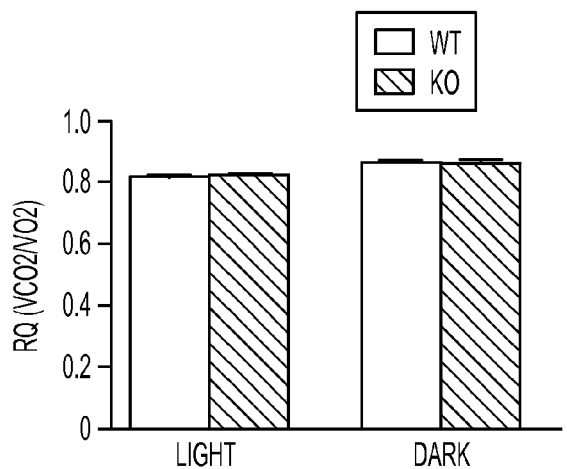
Figure 8C:
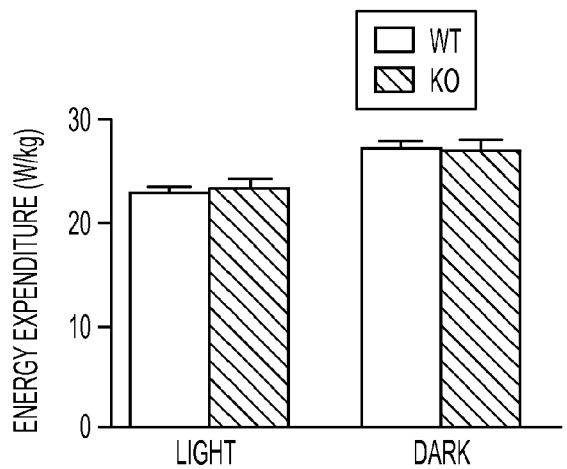

17) Gpr17 reduced leptin signaling, FIG. 8, and increased N2A neuronal cell line resting membrane potential. FIG. 9.

18) siRNA oligomers were identified that knocked down Gpr17 expression in the Gpr17-mCherry stable line. These siRNAs have potential therapeutic use to inhibit or reduce expression of Gpr17 in a targeted cell, thereby increasing insulin sensitivity. The most effective siRNA sequences at reducing Gpr17 expression were SEQ ID NOs: 6, 7, and 9.

Based on these observations certain embodiments of the invention are directed to methods of treating or preventing obesity and/or reducing appetite by administering an agent that reduces Gpr17 expression or biological activity (such as a Gpr17 antagonist or inhibitory oligonucleotide such as siRNA) to a subject in need of such treatment in an amount that treats obesity and/or reduces appetite. Gpr17 antagonists include those identified herein, and others known in the art. Inhibitory RNA and DNA are well-known in the art and include certain siRNA oligomers described herein. Certain embodiments are also directed to the seven new siRNA molecules (SEQ ID Nos: 3-9) herein described that hybridize to and reduce expression of endogenous Gpr17.

Other embodiments are directed to methods for treating eating disorders such as anorexia that are associated with abnormal weight loss, or increasing weight gain by administering therapeutically or prophylactically effective amounts of a Gpr17 agonist to a subject in need of such treatment. Gpr17 agonists include those identified in herein, and others known in the art.

Other embodiments are directed to methods for increasing glucose tolerance and/or insulin sensitivity in a subject having impaired glucose tolerance or low insulin sensitivity by administering an agent that reduces Gpr17 expression or biological activity (such as a Gpr17 antagonist or inhibitory oligonucleotide) to a subject in need of such treatment, in therapeutically or prophylactically effective amounts. A related embodiment is directed to a method for treating diabetes in a subject by administering an agent that reduces Gpr17 expression or biological activity (such as a Gpr17 antagonist or inhibitory oligonucleotide) to the subject in an amount that increases glucose tolerance and/or insulin sensitivity, thereby treating the diabetes.

In certain embodiments the therapeutically effective amount of Gpr17 agonist or antagonist or inhibitory oligonucleotide ranges from 1 microgram/kg to about 100 microgram/kg. The amount will not only vary depending on well-known factors including patient variability and response, the medications he/she is taking, and the formulation, route of administration and bioavailability. Certain other embodiments are directed to the chimeric mice described herein, and to the Agrp-Foxo1$^{-/-}$ mice (KO) knockout mouse.

4. DISCUSSION

Desirable as it might be to inhibit FoxO1 to treat metabolic diseases, this transcription factor is a poor drug target (Pajvani et al., 2011). By contrast, Gpr17 meets several criteria as a drugable target. Inhibiting Gpr27 will r reduce appetite, and treat obesity; it will also increase glucose tolerance and insulin sensitivity. Gpr17 antagonists mimic the effects of FoxO1 ablation on hypothalamic hormone signaling. Importantly, pharmacological inhibition of this receptor inhibits food intake, providing a ready alternative to FoxO1 inhibition. About one-third of all approved drugs target G-protein-coupled receptors (Erlinge, 2011). Gpr17 antagonists are currently in clinical use for the treatment of asthma by inhibiting leukotriene release (e.g., montelukast and pranlukast), and cangrelor has been used as short-acting anti-platelet aggregation agent (Kastrati and Ndrepepa, 2009). Alternately, appetite can be increased thereby treating eating disorders associated with weight loss such as anorexia nervosa, cachexia associated, for example with cancer or HIV.

Figure 7A:
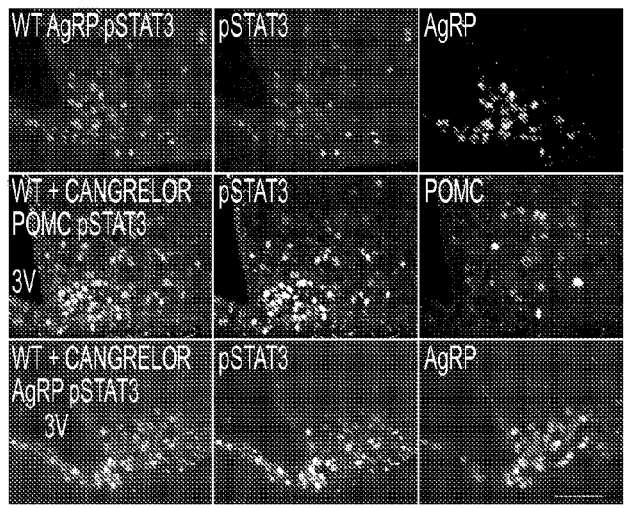
FIG. 7A-7G. Gpr17 modulation affects pSTAT3 content of AgRP neurons and food intake. (A-C) ARH immunohistochemistry of refed AgRP or POMC reporter mice with pSTAT3 (A), pS6 (B), and pAkt (C) following administration of cangrelor into the 3V after an overnight fast. Scale bar 100 µm. (D) Food intake during refeeding in overnight-fasted WT and Agrp-Foxo1$^{-/-}$ mice following ICV administration of saline or cangrelor (n=6). Data presented as means±SEM. *=P<0.05. (E) ARH immunohistochemistry of refed WT and Agrp-Foxo1$^{-/-}$ AgRP reporter mice with pSTAT3 following administration of LTD4 into the 3V after an overnight fast. Scale bar 100 µm. (F) Food intake in satiated WT and Agrp-Foxo1$^{-/-}$ mice after ICV injection of saline or Gpr17 agonist (n=5-9). Data presented as means±SEM. ***=P<0.001. (G) Under fasting conditions (nuclear Foxo1, indicated by the green color), Gpr17 is induced and modulates ion channel activity, leading to increased orexigenic neuropeptide secretion as well as glutaminergic activity (+labeled synapse), and contributing to food intake and HGP. Under fed conditions (phenocopied by the Foxo1 knockout) insulin and leptin signaling concur to inactivate Foxo1 and reduce Gpr17 expression.
Figure 7B:
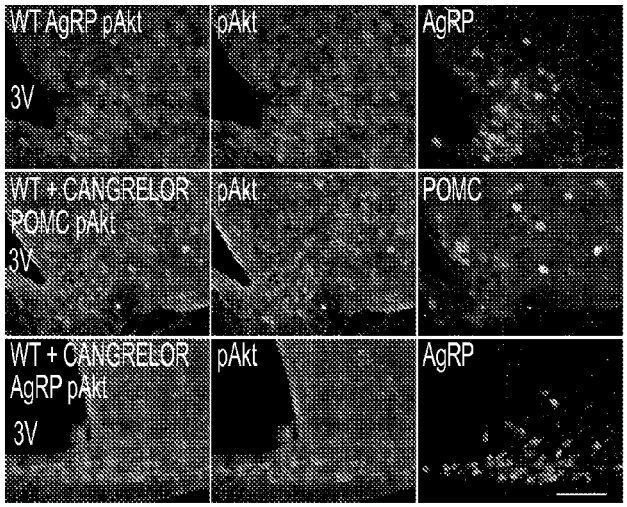
Figure 7C:
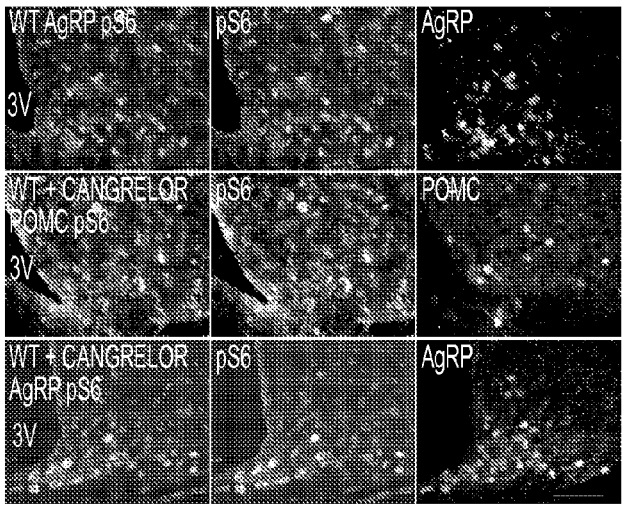
Figure 7D:
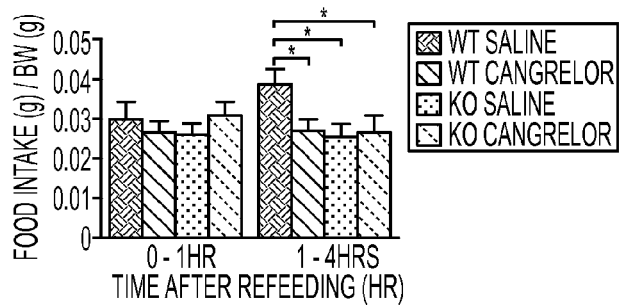
Figure 7E:
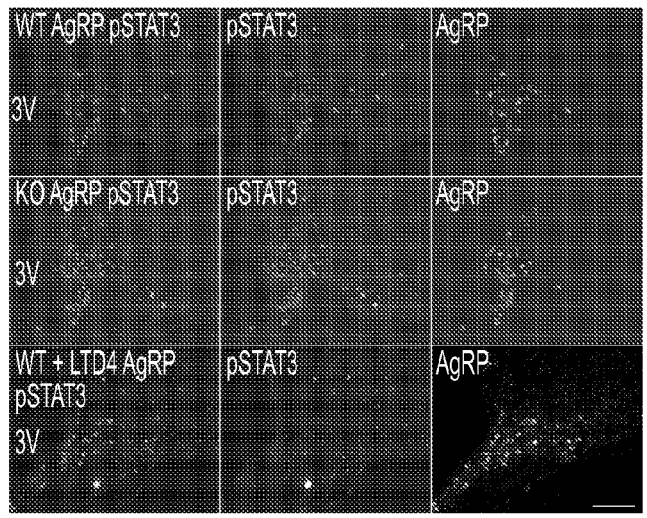

The suitability of Gpr17 antagonists in therapy for treating obesity, diabetes or impaired glucose tolerance or Gpr17 agonists to treat eating disorders associated with abnormal weight loss, and increasing appetite, is bolstered by the fact that these agents act specifically on AgRP neurons. Direct ICV infusion of the Gpr17 antagonist cangrelor resulted in a remarkably specific activation of STAT3 phosphorylation in AgRP neurons (FIG. 7A), while the agonist LTD4 caused a decrease of phospho-STAT3 (FIG. 7E). Phosphorylated Stat3 is herein referred to as "(phospho-STAT3 and pSTAT3"). This is consistent with the observation that Gpr17 levels are extraordinarily high in on AgRP neurons (only 2 cycles less abundant than actin by qPCR), and thus AgRP neurons are sensitive to manipulations of Gpr17, despite the broad distribution of Gpr17 in the brain, facilitating targeted therapy.

Gpr17 Antagonists and Agonists

Gpr17 antagonists for use in embodiments of the invention to reduce appetite and increase glucose tolerance and treat diabetes include:

Leukotriene Antagonists:

CR3465 [CR3465 (L-Tyrosine, N-[(2-quinolinyl)carbonyl]-O-(7-fluoro-2-quinolinylmethyl) sodium salt), MEN91507 [MEN91507 (8-[2-(E)-[4-[4-(4-fluorophenyl)butyloxy]phenyl]vinyl]-4-oxo-2-(5-1H-tetrazolyl)-4H-1-benzopyran sodium salt))], YM158 [YM158 (3-[(4-tert-butylthiazol-2-yl)methoxy]-5'-[3-(4-chlorobenzenesulfonyl)propyl]-2'-(1H-tetrazol-5-ylmethoxy)benzanilide monosodium salt monohydrate), Montelukast with Bambuterol hydrochloride STERLING [bambuterol hydrochloride; montelukast], Mondeslor [desloratadine; montelukast], Alerdain-M [levocetirizine dihydrochloride; montelukast sodium], Loratadine, montelukast sodium Merck & Co. [loratadine; montelukast sodium], MCC847 [masilukast], SKF104353 [pobilukast], Azlaire [pranlukast hydrate], Accolate [zafirlukast]; cysteinylleukotrienes (CysLTs) and 5-phosphoribosyl 1-pyrophosphate (PRPP) Nonaka2005 *Biochem Biophys Res Commun*. 2005 Nov. 11; 337(1):281-8.

P2Y12 Antagonists:

P2Y12 Inhibitor LG LIFE, ZK816667, ARC69931MX [cangrelor], Agreplat [clopidogrel], PRT060128 [elinogrel], Aplet [prasugrel], INS50589 [regrelor disodium], Clotidone [ticlopidine]; S-Clopidogrel; 2-(methythio) adenosine 5-diphosphate trisodium salt, Kobayashi et al. The Journal of Neuroscience, Mar. 12, 2008-28(11):2892-2902; RGS4 (Regulator of G protein signaling 4), BODOR et al. Mol Pharmacol 64, Prasugrel Enantiomers, Leukotriene C4 D4 E4 Antagonists: Montelukast, IUPAC (S,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetic acid, IUPAC sodium (2S)-3-[4-[(7-fluoro-2-quinolyl)methoxy]phenyl]-2-(quinoline-2-carbonylamino)propanoate, CR3465, Bambuterol, Desloratadine; and ATPγS.

Gpr17 Agonists:

include purinergic agonists such as a uracil nucleotides including UDP, UDP-glucose, and UDP-galactose; Jacobson and Boeynaems, 2010) and cysteinyl-leukotriene (cysLT) agonists such as LTC4, LTD4, and LTE4.

Preparation and isolation of the long isoform of hGpr17, hGpr17-L (GenBank accession number NM_005291) are described in *Pugliese*, A. M., et al., Functional characterization of two isoforms of the P2Y-like receptor Gpr17: [$^{35}$S] GTPγS binding and electrophysiological studies in 1321N1 cells, *Am J Physiol Cell Physiol* October 2009 vol. 297 no. 4 C1028-C1040. Routine methods are available for isolating Gpr17.

The sequence for Mus musculus G protein-coupled receptor 17 (Gpr17), mRNA, is NCBI Reference Sequence: NM_001025381.2, LOCUS NM_001025381 5209 bp mRNA linear.

The gene encoding [*Homo sapiens*] GPR17 (Other Designations: G-protein coupled receptor 17; P2Y-like receptor; R12; UDP/CysLT receptor; uracil nucleotide/cysteinyl leukotriene receptor; Location: 2q21) is identified as Annotation: Chromosome 2, NC_000002.11 (128403439 . . . 128410213) MIM: 603071.

*Homo sapiens* G protein-coupled receptor 17 (GPR17). transcript variant 3; mRNA; 1. 2,544 bp; linear mRNA; is identified by Accession: NM_00 1161416.1 Gl: 238814304, GenBank FAST A Graphics Related Sequences.

*Homo sapiens* G protein-coupled receptor 17 (GPR171. transcript variant 1. mRNA, 2. 2,609 bp linear mRNA, Accession: NM_00 1161415.1 Gl: 238814301, GenBank FAST A Graphics Related Sequences.

*Homo sapiens* G protein-coupled receptor 17 (GPR171; transcript variant 4; mRNA; 5. 2,315 bp; linear mRNA is identified by Accession: NM_00 1161417.1 Gl: 238814306, GenBank FAST A Graphics Related Sequences.

*Homo sapiens* G protein-coupled receptor 17 (GPR171; transcript variant 2; mRNA; 6. 2,360 bp; linear mRNA is identified by Accession: NM_005291.2 Gl: 238814303, GenBank FAST A Graphics Related Sequences.

Agents that reduce Gpr17 expression and/or translation include shRNA, (small hairpin RNA), siRNA (small interfering RNA), antisense RNA, ribozymes, and microRNA as described below. Because of the sequence homology of Gpr17 in different species, antisense or siRNA made against human Gpr17 might be used in other animals, and vice versa. The gene and mRNA sequences for Gpr17 are set forth herein.

5. DESCRIPTION OF THE EMBODIMENTS

Screening for Gpr17 Antagonists and Agonists

The present invention further provides methods for the identification of compounds that antagonize Gpr17 and Gpr17 agonists using cell-based assays to detect the effect of the test compound on phosphorylated STAT3 activity in Grp17 overexpressing cells. Gpr17 antagonists identified via assays such as those described herein may be useful, for example, for reducing appetite, increasing glucose tolerance and treating diabetes. Gpr17 agonists can be used to increase appetite and treat eating disorders associated with abnormal weight loss. It is to be noted that the compositions of the invention include pharmaceutical compositions comprising one or more of the compounds identified via such methods. Such pharmaceutical compositions can be formulated, for example, as discussed, below.

An embodiment of a screening assay includes (a) providing a cell that overexpresses Gpr17, (b) determining a first level of pSTAT3 in the cell, (c) contacting the cell with a test compound under conditions and for a time sufficient to allow the test compound to interact with Gpr17 (and for pSTAT3 to change in response to the effect of the test compound on Gpr17), (d) determining a second level of pSTAT3 in the test cell at a predetermined time after contact with the test compound, (e) comparing the first and second levels of pSTAT3, and (f) if the second level is significantly higher compared to the first level, then identifying the test compound as a Gpr17 antagonist; if the second level is significantly lower compared to the first level, then identifying the test compound as a Gpr17 agonist.

In another embodiment, a control cell and a test cell are provided that both overexpress Gpr17, and a first level of pSTAT3 in each cell is determined at a first time point. The test cell is then contacted with a test compound under conditions that permit them to interact. At a second predetermined time after the test cell has been contacted with the test compound, a second level of pSTAT3 is determined in the control and test cells. If the second pSTAT3 test level is significantly higher than both the first control pSTAT3 level and the first test pSTAT3 level, the concluding that the test compound is a Gpr17 antagonist. If the second pSTAT3 test level is significantly lower than both the first control pSTAT3 level and the first test pSTAT3 level, the concluding that the test compound is a Gpr17 agonist.

FACS can be used to detect expression of pSTAT3 in cells and it can be automated for 96 well plates. pSTAT3 can be detected by western blot, for example using the infrared western blot system. Odyssey CLx for Infrared Fluorescent Western Blots from LI-COR Crop. The advantage of the FACS system is that it permits an assay of each single cell in the population for the pStat3 signal intensity while tracking the percentage of pStat3 positive cells in the total population. In an embodiment, the FACS protocol will be optimized for tube based assay using to analyze pSTAT3. Then a high throughput format will be set up using 96- or 384-well plate based for example, on the BD FACS bulletin. (BD High Throughput Sampler User's Guide for the BD LSR II, BD FACSCanto, BD FACSCanto II.)

In another embodiment, pSTAT3 is detected by determining the level of pSTAT3 transcription activity by using a luciferase reporter system that measures the total pSTAT3 in the total cellular population.

Pharmaceuticals and Routes of Administration

The active therapeutic agents (antagonists/agonists/therapeutic oligonucleotides) can be administered as often as is deemed necessary. Fortunately, changes in weight, appetite and glucose tolerance can be measured by well-known methods. Active agents can be administered daily at least once, multiple times per day, or less often, and they can be formulated for administration can be via any route as is explained below.

Cangrelor is a $P2Y_{12}$ inhibitor under investigation as an antiplatelet drug for intravenous application. IUPAC name [dichloro-[[[(2R,3S,4R,5R)-3,4-dihydroxy-5-[6-(2-methylsulfanylethylamino)-2-(3,3,3-trifluoropropylsulfanyl)purin-9-yl]oxolan-2-yl]methoxy-hydroxyphosphoryl]oxy-hydroxyphosphoryl]methyl]phosphonic acid. Unlike the anticoagulant clopidogrel (Plavix), which is a prodrug, cangrelor is an active drug that does not requiring metabolic conversion. Cangrelor is a Gpr17 receptor antagonist (also referred to as an IV ADP-P2Y12 receptor antagonist) with a quick onset and quick offset. It has a plasma half-life of three to six minutes and patients being treated with cangrelor as an anticoagulant returned to normal platelet function in 60 minutes.

Identifiers for Cangrelor include CAS number 163706-06-7, PubChem 9854012, IUPHAR ligand 1776, and Jmol-3D images. The molecular formula for Cangrelor is $C_{17}H_{25}Cl_2F_3N_5O_{12}P_3S_2$, and its molar mass is 776.36 g mol$^{-1}$. Except where noted otherwise, data are given for materials in their standard state (at 25 degrees Celsius, 100 kPa).

Therapeutic doses of cangrelor of between 0.75-60 micrograms/kg/minute have been administered IV for up to 3 hours have been tested. One report by Gaglia et al., shows that a dose of 4 µg/kg per minute appears to result in 100% platelet inhibition in approximately 70% of patients after 15 min.

Therapeutic amounts of between about 0.1 and 100 micrograms/kg/minute of the Gpr17 antagonists and agonists can be used in various embodiments of the present invention, however higher amounts may also be administered depending on the severity of the disorder, the bioavailability and other factors. Reports of administering cangrelor include: with doses up to IV bolus 60 mcg/kg; 8 mcg/kg×3 hrs; J Clin Pharmacol. 2010 January; 50(1):27-35. Epub 2009 Sep. 24) 15-microg/kg bolus followed by a 2-microg/kg/min infusion or a 30-microg/kg bolus followed by a 4-microg/kg/min infusion); Novel Antiplatelet Therapy: P2Y12 Receptor Antagonist-cangrelor, Michael A. Gaglia Jr., MD, M Sc et al., American Heart Journal. 2010; 160(4):595-604 (infusion of 4-µg/kg per minute peak inhibition occurs after 15 minutes).

The optimum amount and route of administration of Gpr17 agonists (to increase appetite and weight gain) and antagonists (to reduce appetite and weight gain thereby treating or preventing obesity or diabetes) is to be determined by routine experimentation. Gpr17 agonists and antagonists are collectively referred to as Gpr17 ligands or therapeutic agents.

While Cangrelor was administered by injection into the brain of experimental animals, this route is not an optimal one for controlling weight gain/loss. Therefore, the Gpr17 ligands will be formulated to optimize their ability to cross the blood brain barrier to facilitate uptake and increase efficacy. Methods for this are known in the art.

The passage of therapeutic agents described herein (agonists, antagonists, and therapeutic oligonucleotides) through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier. The passage of the agent can also be facilitated by its covalent coupling to a peptide vector capable of transporting the agent through the blood-brain barrier. Peptide transport vectors known as blood-brain barrier permeabilizer compounds are disclosed in U.S. Pat. No. 5,268,164. Site specific macromolecules with lipophilic characteristics useful for delivery to the brain are disclosed in U.S. Pat. No. 6,005,004.

Regarding the dose of inhibitory oligonucleotides, Yuen, et al. (Clin Cancer Res November 1999 5; 3357 Phase I Study of an Antisense Oligonucleotide to Protein Kinase C-α (ISIS 3521/CGP) in Patients with Cancer) reported amounts of antisense in the range of from 0.5 to 3.0 mg/kg/day. Pharmacokinetic measurements showed rapid plasma clearance and dose-dependent steady-state concentrations of ISIS 3521. Wada et al., 20120016012, reported doses of the RNAi-molecule or the shRNA-molecule-expressing vector of from about is 0.0001 to 100 mg/kg/day. For the present invention, inhibitory oligonucleotides can be administered at from about is 0.0001 to 100 mg/kg/day.

Inhibitory Oligonucleotides

In a transient knockdown, the binding of an inhibitory oligonucleotide to the active gene or its transcripts (mRNA) causes decreased expression through blocking of transcription (in the case of gene-binding), degradation of the mRNA transcript (e.g., by small interfering RNA (siRNA) or RNase-H dependent antisense) or blocking either mRNA translation, pre-mRNA splicing sites or nuclease cleavage sites used for maturation of other functional RNAs such as miRNA (e.g., by Morpholino oligos or other RNase-H independent antisense).

The therapeutic oligonucleotides used herein include any isolated oligonucleotide that specifically hybridize to either the Gpr17 gene or mRNA, thereby reducing expression or biological activity of either the Gpr17 gene or mRNA encoding Gpr17. Therapeutic oligonucleotides are also referred to herein as "inhibitory oligonucleotides." Therapeutic oligonucleotides are synthesized in vitro and do not include compositions of biological origin. Based on these known sequences of the targeted Gpr17 gene and mRNA described herein, therapeutic oligonucleotides can be engineered using methods known in the art. Therapeutic oligonucleotides include antisense DNA or RNA (or chimeras thereof), small interfering RNA (siRNA), micro RNA (miRNA), short hairpin RNA, ribozymes, microRNA mimic. Different combinations of these therapeutic oligonucleotides can be formulated for administration to a subject using methods well known in the art.

Therapeutic oligonucleic act via a variety of mechanisms. siRNA or miRNA can down-regulate intracellular levels of specific proteins through a process termed RNA interference (RNAi). Following introduction of siRNA or miRNA into the cell cytoplasm, certain double-stranded RNA constructs can bind to a protein termed RISC (RNA-Induced Silencing Complex) that is a multiprotein complex that incorporates one strand of a small interfering RNA (siRNA) or micro RNA (miRNA). RISC uses the siRNA or miRNA as a template for recognizing complementary mRNA. When it finds a complementary strand, it activates RNase and cleaves the RNA. RNAi can provide down-regulation of specific proteins by targeting specific destruction of the corresponding mRNA that encodes for protein synthesis. To date, siRNA constructs have shown the ability to specifically down-regulate target proteins in both in vitro and in vivo models and they are currently being evaluated in clinical studies.

Antisense oligonucleotides and ribozymes can also inhibit mRNA translation into protein. In the case of antisense constructs, these single stranded deoxynucleic acids have a complementary sequence to that of the target protein mRNA and bind by Watson-Crick base pairing. This binding either prevents translation of the target mRNA and/or triggers RNase H degradation of the mRNA transcripts. Antisense has shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA.

It is desirable to optimize the stability of the phosphodiester internucleotide linkage and minimize its susceptibility to exonucleases and endonucleases in serum. (Zelphati, O., et al., Antisense. Res. Dev. 3:323-338 (1993); and Thierry, A. R., et al., pp 147-161 in Gene Regulation: Biology of Antisense RNA and DNA (Eds. Erickson, R P and Izant, J G; Raven Press, NY (1992)). Therapeutic nucleic acids being currently being developed do not employ the basic phosphodiester chemistry found in natural nucleic acids, because of these and other known problems. Modifications have been made at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130).

For use in embodiments of the present invention may be of various lengths, generally dependent upon the particular form of nucleic acid, typically from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

In particular embodiments, the therapeutic oligonucleotide (or a strand thereof) specifically hybridizes to or is complementary to a target a polynucleotide, such as an mRNA or miR molecule. "Specifically hybridizable" and "complementary" are terms which are used to indicate a sufficient degree of complementarity such that stable and specific binding occurs between the DNA or RNA target and the oligonucleotide. It is understood that a therapeutic oligonucleotide need not be 100% complementary to its target nucleic acid sequence to be specifically hybridizable. A therapeutic oligonucleotide is specifically hybridizable when binding of the oligonucleotide to the target interferes with the normal function of the target molecule to cause a loss of utility or expression of the target, and there is a sufficient degree of complementarity to avoid non-specific binding of the oligonucleotide to non-target sequences under conditions in which specific binding is desired, i.e., under physiological conditions in the case of in vivo assays or therapeutic treatment.

Small interfering RNA (siRNA) has essentially replaced antisense ODN and ribozymes as the next generation of targeted oligonucleotide drugs under development. RISC loaded with siRNA mediates the degradation of homologous mRNA transcripts; therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., Nature Reviews 6:443-453 (2007).

While the first described RNAi molecules were RNA:RNA hybrids comprising both an RNA sense and an RNA antisense strand, it has now been demonstrated that DNA sense: RNA antisense hybrids, RNA sense:DNA antisense hybrids, and DNA:DNA hybrids are capable of mediating RNAi (Lamberton, J. S, and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded oligonucleotides comprising two separate strands, i.e., a sense strand and an antisense strand, e.g., small interfering RNA (siRNA); double-stranded oligonucleotide comprising two separate strands that are linked together by non-nucleotidyl linker; oligonucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule. A single strand siRNA compound may be sufficiently long that it can enter the RISC and participate in RISC mediated cleavage of a target mRNA. A single strand siRNA compound is typically at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

A "double stranded siRNA compound" as used herein, is a siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. As used herein, term "antisense strand" means the strand of a siRNA compound that is sufficiently complementary to a target molecule, e.g., a target RNA, to reduce its expression (for example mRNA translation).

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded siRNA compound may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In some embodiments, the siRNA compound is sufficiently large that it can be cleaved by an endogenous molecule, e.g., by Dicer, to produce smaller siRNA compounds, e.g., siRNAs agents.

The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of a siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also within the invention.

As used herein, the phrase "mediates RNAi" refers to the ability to silence, in a sequence specific manner, a target RNA, such as mRNA. While not wishing to be bound by theory, it is believed that silencing uses the RNAi machinery or process and a guide RNA, e.g., an ssiRNA compound of 21 to 23 nucleotides.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA.

MicroRNAs

Micro RNAs (miRNAs) are a highly conserved class of small RNA molecules that are transcribed from DNA in the genomes of plants and animals, but are not translated into protein. Processed miRNAs are single stranded (about 17-25 nucleotide (nt)) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes. MiRNAs that is specific for Gpr17 mRNA can be used to reduce expression of Gpr17.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g., a target gene mRNA. Antisense oligonucleotides are thought to inhibit gene expression by binding to a complementary mRNA. Binding to the target mRNA can lead to inhibition of gene expression either by preventing translation of complementary mRNA strands by binding to it or by leading to degradation of the target mRNA Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use. The efficacy of antisense oligonucleotides for inhibiting protein synthesis is well established. See, for example, (U.S. Pat. No. 5,739,119 and U.S. Pat. No. 5,759,829); (Jaskulski et al., Science. 1988 Jun. 10; 240(4858):1544-6; Vasanthakumar and Ahmed, Cancer Commun. 1989; 1(4):225-32; Penis et al., Brain Res Mol Brain Res. 1998 Jun. 15; 57(2):310-20; U.S. Pat. No. 5,801, 154; U.S. Pat. No. 5,789,573; U.S. Pat. No. 5,718,709 and U.S. Pat. No. 5,610,288); (U.S. Pat. No. 5,747,470; U.S. Pat. No. 5,591,317 and U.S. Pat. No. 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Ribozymes

According to another embodiment of the invention, targeted mRNA is inhibited by ribozymes, which have specific catalytic domains that possess endonuclease activity (Kim and Cech, Proc Natl Acad Sci USA. 1987 December; 84(24): 8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction. The enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis delta virus, group I intron or RNaseP RNA (in association with an RNA guide sequence) or Neurospora VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

miRNA Mimics

The term "microRNA mimic" refers to synthetic non-coding RNAs (i.e., the miRNA is not obtained by purification from a source of the endogenous miRNA) that are capable of entering the RNAi pathway and regulating gene expression through inhibiting targeted mRNA. miRNA mimics can be designed as mature molecules (e.g. single stranded) or mimic precursors (e.g., pri- or pre-miRNAs) miRNA mimics can be comprised of nucleic acid (modified or modified nucleic acids) including oligonucleotides comprising, without limitation, RNA, modified RNA, DNA, modified DNA, locked nucleic acids, or 2'-O,4'-C-ethylene-bridged nucleic acids (ENA), or any combination of the above (including DNA-RNA hybrids). In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-O methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality. In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications of oligonucleotides can confer improved properties, and, e.g., can render oligonucleotides more stable to nucleases. As oligonucleotides are polymers of subunits or monomers, many of the modifications described below occur at a position which is repeated within an oligonucleotide, e.g., a modification of a base, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal region, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of a double-stranded oligonucleotide or may only occur in a single strand region of a double-stranded oligonucleotide. For example, a phosphorothioate modification at a non-bridging oxygen position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g., different nucleotides of an oligonucleotide have different modifications described herein.

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown.

A modified RNA can include modification of all or some of the sugar groups of the ribonucleic acid. For example, the 2' hydroxyl group (OH) can be modified or replaced with a number of different "oxy" or "deoxy" substituents. The sugar group can also contain one or more carbons that possess the opposite stereochemical configuration than that of the corresponding carbon in ribose. Thus, an oligonucleotide can include nucleotides containing e.g., arabinose, as the sugar.

The 3' and 5' ends of an oligonucleotide can be also modified at either or both ends to increase stability. When a linker/phosphate-functional molecular entity-linker/phosphate array is interposed between two strands of a dsRNA, this array can substitute for a hairpin RNA loop in a hairpin-type RNA agent.

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases", "modified bases", "non-natural bases" and "universal bases" described herein, can be employed. U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Modifications to oligonucleotides can also include attachment of one or more cationic groups to the sugar, base, and/or the phosphorus atom of a phosphate or modified phosphate backbone moiety.

As used herein, a "therapeutically effective amount" of the siRNA is an amount sufficient to cause RNAi-mediated degradation of the target mRNA, or an amount sufficient to inhibit the progression of an enumerated disease in a subject or to reduce Gpr17 expression or biological activity.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Antisense SEQ ID No 1 and 2 for use in certain embodiments of the invention are described in Abbracchio.

SEQ ID NO. 1
AACTGTACCG GGAGAAGGCC

SEQ ID NO. 2
GGGATCACAA GTCAGGCAC

Other siRNAs are described herein for use in the embodiments of the invention and include SEQ ID NOs: 3-9

Pharmaceutical Preparations

Embodiments of the present invention involve administration of pharmaceutical compositions and formulations which include the antagonists of Gpr17, therapeutic oligonucleotides that reduce Gpr17 protein expression and/or biological activity, which compositions are administered in an amount that reduces expression and/or biological activity of Gpr17. Similar formulations include agonists of Gpr17.

The pharmaceutical compositions of the present invention may be administered in a number of ways including oral, local intravenous, parenteral/intra-arterial, subcutaneous, intraperitoneal or intramuscular injection or infusion; or intracranial, e.g., intrathecal or intraventricular, administration. Pharmaceutical compositions of the present invention contain the therapeutic agent (such as antagonist/agonist or antisense nucleic acids or siRNA that reduce the expression of a targeted Gpr17 protein) in an amount sufficient to prevent or treat an enumerated disease. Enumerated diseases include those treated with antagonists and agents that reduce Gpr17 expression and biological activity thereby treating obesity, diabetes and impaired glucose tolerance; and also include those diseases treated with agonists such as anorexia nervosa. The therapeutic agent can be formulated with an acceptable carrier using methods well known in the art. The actual amount of therapeutic agent will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, and the route of administration, regime, and purity and activity of the composition.

New pharmaceutical formulations according to embodiments of the invention include combinations of two or more antagonists or two or more agonists. In an embodiment the combination of antagonists or agonists include one that targets/binds to the uracil nucleotide receptor and one that targets/binds to the cysteinyl-leukotriene receptor.

A suitable subject can be an individual or animal that is suspected of having, has been diagnosed as having, or is at risk of developing an enumerated disease, and like conditions as can be determined by one knowledgeable in the art.

Techniques for formulation and administration can be found in "Remington: The Science and Practice of Pharmacy" (20th edition, Gennaro (ed.) and Gennaro, Lippincott, Williams & Wilkins, 2000), incorporated herein by reference. The pharmaceutical compositions of the present invention can be administered to the subject by a medical device, such as, but not limited to, catheters, balloons, implantable devices, biodegradable implants, prostheses, grafts, sutures, patches, shunts, or stents. A detailed description of pharmaceutical formulations of oligonucleotides is set forth in U.S. Pat. No. 7,563,884.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients. Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

EXAMPLES

Example 1

Materials and Methods

Mice.
C57BL/6 and Gt(Rosa)26Sor$^{tm9(CAG-tdTomato)Hze}$ mice were from The Jackson Laboratories. The Columbia University Animal Care and Utilization Committee approved all procedures. Normal chow diet (NCD) had 62.1% calories from carbohydrates, 24.6% from protein and 13.2% from fat (PicoLab rodent diet 20, 5053; Purina Mills). Weight and length were measured to calculate body mass index and estimated body composition by nuclear magnetic resonance (Bruker Optics). Agrp-specific FoxO1 knockouts were generated by mating Agrp-Ires-Cre-transgenic mice (Tong et al., 2008) with Foxo1$^{loxP/loxP}$ mice (Paik et al., 2007) and genotyped them as previously described. Analyses Agrp-Foxo1$^{-/-}$ mice that showed somatic recombination owing to stochastic embryonic expression of Agrp-Tres-Cre were excluded.

Metabolic Analyses.

Food intake and refeeding response were measured as described (Plum et al., 2009), using a TSE Labmaster Platform (TSE Systems) for indirect calorimetry and activity measurements (Banks et al., 2008). Glucose clamps were performed as described (Okamoto et al., 2005). ELISA for leptin, insulin, and glucagon measurements (Millipore), and colorimetric assays for plasma free fatty acids and glycerol (Wako) were used.

Stereotactic Injections.

Stereotactic manipulations in 3-4 month-old C57BL/6 mice were performed. Cannulae were placed and allowed 1 week for recovery (−1.8 mm anterior and 0 mm lateral to bregma and 5.3 mm below the skull surface). Correct positioning of the cannulae was verified by monitoring drinking activity after angiotensin injection. After an overnight fast and 20 min before refeeding, cangrelor (0.455 nmol) was injected into the 3$^{rd}$ ventricle and measured food intake at the times indicated. For immunohistochemistry studies, mice 4-5 hr were perfused after refeeding. LTD4 0.02 nmol and UDP-glucose 0.45 nmol were perfused into the 3$^{rd}$ ventricle of satiated mice and measured food intake afterwards.

Immunostaining.

Mouse brains were processed and cut 10-µm-thick coronal sections for immunohistochemistry as described (Plum et al., 2009), using pAkt (Cell Signaling #4060), pSTAT3 (Cell Signaling #9131), and pS6 antibodies (Cell Signaling #4858); Foxo1 antibody (Santa Cruz, FKHR-H128, sc11350).

RNA Procedures.

RNA was extracted with Trizol (Invitrogen) and reverse transcribed with Superscript II reverse transcriptase. Quantitative PCR was performed using primers spanning introns. Primer sequences are available upon request.

Western Blotting.

RIPA buffer was used to extract protein and loaded equal amount of protein for gel electrophoresis.

Chromatin Immunoprecipitation Assays.

Intact chromatin was isolated from cultured N2A cells using ChIP-IT Express Enzymatic kit (Active Motif). Putative Foxo1 binding site on the Gpr17 promoter was identified by genomatrix software. Multiple pairs of primers were used for the subsequent amplification of Gpr17 promoter and yielded the same result. The pair used for electrophoresis is (forward) SEQ ID NO: 10 5'-CCACACAGCTTATGTAG-CATTGAGG-3' and (reverse) SEQ ID NO: 115'-AGCAG-GAAGGTCTCAGTAACTCCC-3'.

Hypothalamic Neuropeptide Assays.

Acid extracts were prepared from mediobasal hypothalamus, and measured AGRP and αMSH as previously described (Plum et al., 2009). HPLC was used to characterize AGRP immunoreactivity. The elution profile of AGRP immunoactivity in the MBH of Agrp-Foxo1$^{-/-}$ and WT mice was similar and consisted primarily of C-terminal AGRP$_{83-132}$, as reported (Breen et al., 2005).

Flow Cytometry and Gene Profiling of AgRP Neurons.

Mediobasal hypothalami was dissociated from Agrp-Foxo1$^{loxP/-}$ Rosa-tomato and Agrp-Foxo1$^{-/-}$ Rosa-tomato neonates (40-50 animals per genotype) with papain dissociation kit (Worthington Biochemical). Live neurons were gated to collect Rfp-positive Foxo1$^{+/loxP}$; Agrp-Ires-cre; Rfp and Foxo1$^{loxP/loxP}$; Agrp-Ires-cre; Rfp AgRP neurons. RNA was isolated with Trizol LS reagent, amplified it (NuGEN WT-Ovation Pico RNA Amplification System) and processed it for hybridization with Affymetrix chips (GeneChip Mouse Exon 1.0 ST Array). GOrilla and R were used for pathway analysis and heatmap generation.

Electrophysiology and Patch-Clamp.

300-µm coronal ARH slices were prepared from 6- to 8-week-old mice using ice cold sucrose-based cutting solution (adjusted to pH 7.3) containing (in mM): 10 NaCl, 25 NaHCO$_3$, 195 sucrose, 5 glucose, 2.5 KCl, 1.25 NaH$_2$PO$_4$, 2 Na pyruvate, 0.5 CaCl$_2$, and 7 MgCl$_2$ bubbled continuously with 95% O$_2$ and 5% CO$_2$. Slices were allowed to recover at least 45 minutes at room temperature in recording solution (adjusted to pH 7.3) containing (in mM): 125 NaCl, 5 glucose, 25 NaHCO$_3$, 2.5 KCl, 1.25 NaH$_2$PO$_4$, 2 CaCl$_2$, and 1 MgCl$_2$ bubbled continuously with 95% O$_2$ and 5% CO$_2$ before transferring them to a perfusion chamber for recording. Patch pipettes were pulled to resistances of 7-9 MΩ and filled them with solution (adjusted to pH 7.3) containing 128 K gluconate, 10 KCl, 10 HEPES, 0.1 EGTA, 2 MgCl$_2$, 0.3 Na-GTP, and 3 Mg-ATP. Cells were selected using an upright microscope fitted with fluorescence optics (Nikon) and patched under IR-DIC optics. Electrical access was assessed in the whole-cell recording mode using a small-voltage step-pulse before and at the end of the current clamp recordings. Recordings were discarded in which the series resistance had been >15 MΩ. Current clamp recordings were acquired with no current injection using a MultiClamp 700B amplifier and Clampex data acquisition software (Axon Instruments). Action potential (AP) firing frequency, membrane potential, and AP amplitude using MiniAnalysis (Synaptosoft) were recorded at room temperature and analyzed. Electrophysiological recording to measure mEPSC and mIPSC in brain slices was performed as previously described (Pinto et al., 2004).

Statistical Analyses.

Data were analyzed with Student's t test or one-way ANOVA using GraphPad Prism software. The customary threshold of $P<0.05$ was used to declare statistical significance.

Lentivirus—Gpr17-mCherry Lentivirus.

Mouse Gpr17 cDNA was cloned into pcDNA-mCherry to generate cDNA coding Gpr17-mCherry fusion protein. This DNA fragment was cloned into pLKO-CMV vector. Positive clones were identified and confirmed by sequencing. pLKOCMV-GPR17-mCherry was used to produce Lenti-GPR17-mCherry virus in 293T cells. The full sequence information about the Gpr17-mCherry lentivirus, is set forth below.

1. Subcloning strategy:
Cut pLKO-CMV (purchased from Sigma) with Nhe1/Xba1 and digested pcDNA3-GPR17-mCherry with Nhe1/Xba1 (=1.8 kb).
Screen positive clones with EcoR1.
2. A positive clone was sequenced. The result was showed the GPR17-mcherry was correctly inserted pLKOCMV vector.
3. Produced Lenti-GPR17-mCherry virus in 293T cells.
(II) Cell line—Gpr17-mCherry stable line Neuro2A cells were transduced with lentivirus encoding Gpr17-mCherry. Briefly, 5×105 cells were seeded into P100 tissue culture plate. 24 hrs after seeding, 1 ml 1×105 fu/ml lentivirus was added. Lentivirus was used as low titer stock to ensure single copy insertion per cell. Cells were cultured and propagated for 7 days before the initial sorting.

mCherry positive cells (~3% of total population) were collected. mCherry Cells were propagated for 7 days after which the cells were sorted for a second round, with the mCherry positive population reaching ~50%. These cells were further propagated and subjected for a third round of sorting. Finally, the mCherry positive population reached ~100%. These cells were used as Gpr17-mCherry stable line.

KO Mouse—Gpr17 Conditional Knockout Mouse.

A Gpr17 conditional targeting vector (clone name: PG00162_Z_4_B07) was purchased from KOMP (knockout mouse project). DNA was extracted and digested with restriction enzymes to ensure the correct digestion pattern. DNA was linearized and electroporized into ES cells. ES cell clones were selected and screened for targeting vector insertion. Six positive clones were selected and further propagated. Two ES clones were injected into mouse blastocysts to generate chimeric mice. Male chimeras were bred with C57B1a female mice to get germ-line transmission. The offspring were bred with beta-Actin-Flpe mice to delete the neo cassette. Heterozygous mice (Gpr17 lox/+) from this crossing were bred with AgRP-ires-Cre mice to get homozygous conditional knockout mice (Gpr17 lox/lox, AgRP-ires-Cre).

siRNA—Gpr17 siRNA.

Seven siRNA sequences were designed based on the gene sequence of mouse Gpr17. DNA oligomers were ligated into a MSCV-P2Gm vector and verified by sequencing. The correct clones were used for further evaluation of the effectiveness of each RNAi construct. Gpr17-mCherry-stable line was transfected with each of the seven constructs. The effectiveness of RNAi was scored by the diminished mCherry signal in cells. The most effective RNAi sequences were then cloned into MSCV-FLIP vector to generate adenovirus. The resultant adenovirus expresses RNAi upon Cre-dependent recombination. Seven oligomer sequences to generate Gpr17 RNAi. The 7 oligomers were ligated into the vector (MSCV-P2Gm) to generate RNAi specific for Gpr17 gene. The sequences are provided as following. The common adaptor sequence is provided, and the targeting siRNA (specific for mouse Gpr17) sequence is highlighted with underline.

SiRNA

SEQ ID NO. 3
TGCTGTTGACAGTGAGCGCTCAGTCTATGTGCTTCACTACTAGTGAAGCC

ACAGATGTAGTAGTGAAGCACATAGACTGAATGCCTACTGCCTCGGA

SiRNA

SEQ ID NO. 4
TGCTGTTGACAGTGAGCGACCACAGACAGTGCAGACCAACTAGTGAAGCC

ACAGATGTAGTTGGTCTGCACTGTCTGTGGGTGCCTACTGCCTCGGA

SiRNA

SEQ ID NO. 5
TGCTGTTGACAGTGAGCGACTCTTCTATCTGAACATGTATTAGTGAAGCC

ACAGATGTAATACATGTTCAGATAGAAGAGGTGCCTACTGCCTCGGA

SiRNA

SEQ ID NO. 6
TGCTGTTGACAGTGAGCGATGGCTTCCTCTTCTATCTGAATAGTGAAGCC

ACAGATGTATTCAGATAGAAGAGGAAGCCAGTGCCTACTGCCTCGGA

SiRNA

SEQ ID NO 7
TGCTGTTGACAGTGAGCGCCCGGATCACCTCCTGCCTCACTAGTGAAGCC

ACAGATGTAGTGAGGCAGGAGGTGATCCGGTTGCCTACTGCCTCGGA

SiRNA

SEQ ID NO. 8
TGCTGTTGACAGTGAGCGCGTTGTCTGCCTGCAACTGTACTAGTGAAGCC

ACAGATGTAGTACAGTTGCAGGCAGACAACTTGCCTACTGCCTCGGA

SiRNA

SEQ ID NO. 9
TGCTGTTGACAGTGAGCGAAACTGTACCGGGAGAAGGCCTTAGTGAAGCC

ACAGATGTAAGGCCTTC

SiRNA oligonucleotides that specifically hybridize to Gpr17 are commercially available, and these also can be used in embodiments of the invention. They include GPR17 siRNA (h) sc-76030, GPR17 siRNA (m) sc-76031, GPR17 (h)-PR sc-76030-PR, and GPR17 (m)-PR sc-76031-PR available from Santa Cruz Biotechnology. GPR17 shRNA Plasmid (h) are also available, including sc-76030-SH, and GPR17 shRNA (h) Lentiviral Particles sc-76030-V.

Generation and Analysis of Agrp-Specific FoxO1 Knockout Mice.

To ablate FoxO1 in AgRP neurons, Foxo1$^{loxP/loxP}$ and Agrp-Ires-cre mice (Tong et al., 2008) were crossed. Cre-mediated deletion of the loxP-flanked Foxo1 DNA resulted in null Foxo1 alleles in AgRP neurons (hereafter Agrp-Foxo1$^{-/-}$). To assess the extent of Foxo1 ablation, a reporter allele encoding red fluorescent protein upon Cre-mediated recombination (Rosa-tomato) was introduced into Agrp-Foxo1$^{-/-}$ animals. The resulting Agrp-Foxo1$^{-/-}$; Rosa-tomato mice displayed a red fluorescence pattern in the arcuate nucleus (ARH) consistent with AgRP neuron localization (FIG. 1A). Differences in the relative number or size of ARH AgRP neurons between wild-type and Agrp-Foxo1$^{-/-}$ mice were not detected. Immunohistochemistry indicated that FoxO1 was highly expressed in ARH neurons, including AgRP neurons, of wild-type mice, but was selectively undetectable in AgRP neurons of Agrp-Foxo1$^{-/-}$ mice (FIG. 1A).

FACS Detection.

After leptin stimulation, cells were collected and resuspended in 0.5 ml PBS. Formaldehyde was added to a final concentration of 2-4%. Cells were fixed for 10 min at 37° C. and then chilled on ice for 1 min. Cells were permeabilized by adding ice-cold 100% methanol slowly to pre-chilled cells, while gently vortexing, to a final concentration of 90% methanol. Subsequently, cells were incubated on ice for 30 min. For each sample, an aliquot of 0.5-1×10$^6$ cells was put into each assay tube. 2-3 ml Incubation Buffer was added to each tube and rinse by centrifugation. Repeat once. For blocking, cells were resuspended in 100 µl Incubation Buffer per assay tube and incubated 10 min at room temperature. Primary antibody Phospho-Stat3 (Tyr705) (D3A7) XP® Rabbit mAb (Cell Signaling Technology, Inc #9145) was added into the cell suspension. Cells were allowed to incubate with primary antibody for 1 hr at room temperature. Cells were rinsed as before in Incubation Buffer by centrifugation. Cells were incubated with secondary antibody—Alexa Fluor® 488 Goat Anti-Rabbit IgG (Invitrogen, A-11034) for 30 min at room temperature. Cells were rinsed as before in Incubation Buffer by centrifugation. Finally, cells were resuspended in 0.5 ml PBS and analyzed on flow cytometer. This method can be adapted to detect pSTAT3.

Example 2

Metabolic Features of Agrp-Foxo1$^{-/-}$ Mice

Improved Energy Homeostasis in Agrp-Foxo1$^{-/-}$ Mice

Figure 1B:
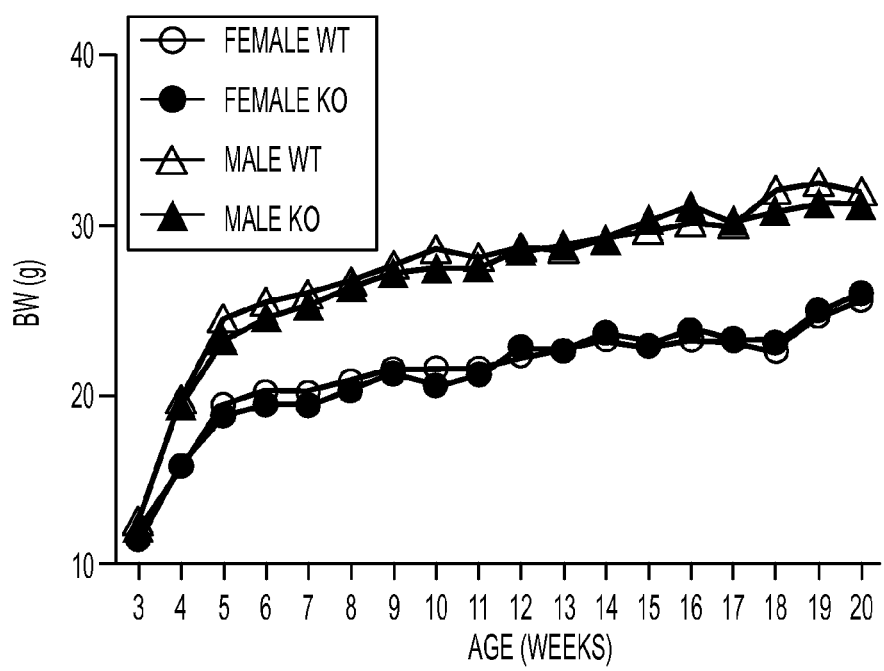

Body weight of female and male Agrp-Foxo1$^{-/-}$ mice was comparable to wild-type controls or trended lower without reaching statistical significance (FIG. 1B). Both female and male Agrp-Foxo1$^{-/-}$ mice showed altered body composition, with a remarkable 18-30% decrease of fat mass and a significant 3-5% increase of lean mass (FIG. 1C).

Male Mice of Matched Body Weight and Composition were Selected for Calorimetry Studies.

Respiratory exchanges, energy expenditure and food intake were measured. When fed ad libitum, Agrp-Foxo1$^{-/-}$ mice were comparable to wild-type controls with regard to oxygen consumption (VO$_2$), respiratory quotient (RQ), and energy expenditure (FIG. 8A-C), but showed reduced locomotor activity during light and dark phases of the light cycle (FIG. 1D), as well as reduced cumulative food intake during the 24-h period (FIG. 1E) that was accounted for by reduced intake during the dark phase of the light cycle (FIG. 1F).

To determine whether reduced food intake was due to increased satiety, mice were examined during fasting and refeeding. Male Agrp-Foxo1$^{-/-}$ mice showed significantly reduced locomotor activity during an overnight fast, consistent with reduced food foraging behavior (FIG. 1G). Moreover, they showed significantly reduced rebound food intake after an overnight fast (FIG. 1H). In light of the role of FoxO1 in orexigenic and anorexigenic neuropeptide expression (Kitamura et al., 2006; Plum et al., 2009), AGRP and MSH levels were examined. After fasting, AGRP was significantly reduced in the mediobasal hypothalamus (MBH) of male Agrp-Foxo1$^{-/-}$ mice, while αMSH was comparable to wild-type controls (FIG. 1I). Agrp is a transcriptional target of FoxO1 (Kitamura et al., 2006). Accordingly, we found decreased Agrp mRNA in ARH punch biopsies from overnight-fasted Agrp-Foxo1$^{-/-}$ mice (FIG. 1I). In contrast, transcript levels of the αMSH precursor, Pomc, were unaltered (FIG. 1I). Moreover, Agrp-Foxo1$^{-/-}$ mice were largely protected from high fat diet-induced weight gain (FIG. 1J). Thus, FoxO1 in AgRP neurons is important to regulate satiety and diet-induced obesity.

Decreased Hepatic Gluconeogenesis and Gene Expression were Seen in Agrp-Foxo1$^{-/-}$ Mice.

Figure 2A:
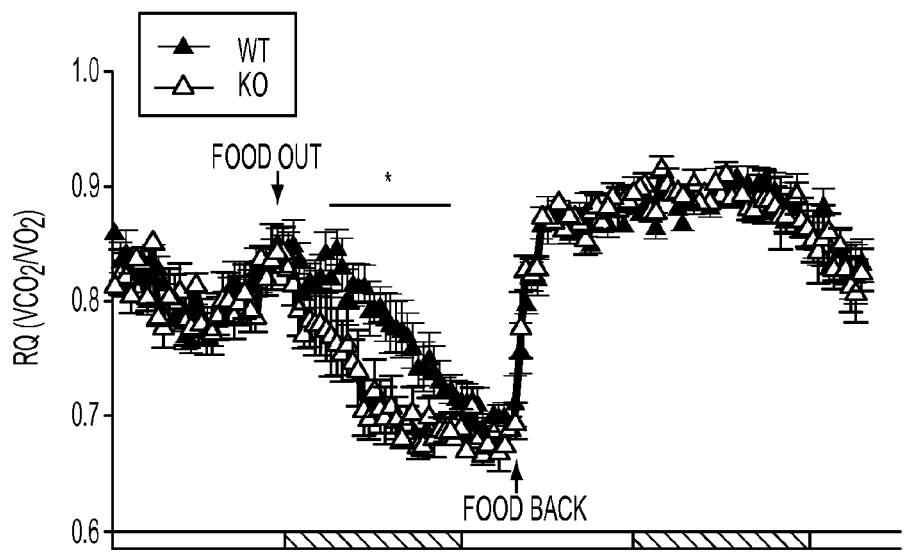
FIG. 2A-2F. Respiratory quotient and glucose production in Agrp-Foxo1$^{-/-}$ mice. (A) RQ measured during fasting and refeeding in Agrp-Foxo1$^{-/-}$ (KO) and wild-type (WT) mice (n=5-7 for each genotype). (B-D) Hyperinsulinemic euglycemic glucose clamps showing glucose infusion rates (GIR) (B), glucose disposal (Rd) (C), and hepatic glucose production (HGP) (D) with insulin (3.6 µM/ml) (n=6 for each genotype). (E,F) Time course (E) and area under curve (AUC) (F) of pyruvate tolerance tests (PTT) (n=6 for each genotype). Data presented as means±SEM. *=P<0.05.

Given the key role of FoxO1 in hormone-dependent hepatic glucose production (HGP) (Matsumoto et al., 2007), and the effect of insulin receptor signaling in AgRP neurons on this process (Konner et al., 2007), the liver response to FoxO1 ablation in AgRP neurons was investigated. After acclimating mice to the calorimetry cage for >72 hrs, they were subjected to an overnight fast; shortly upon starting the fast, Agrp-Foxo1$^{-/-}$ mice showed a more rapid drop of RQ than controls, but they had rebound RQ similar to controls once referred (FIG. 2A). This finding indicates that fasted Agrp-Foxo1$^{-/-}$ mice adapt more rapidly from carbohydrates to fatty acids as energy source.

Figure 2B:
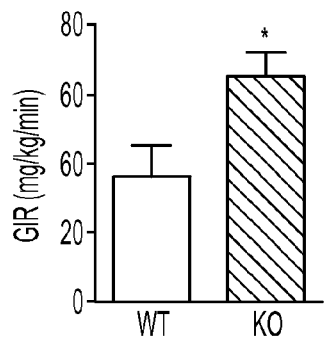
Figure 2C:
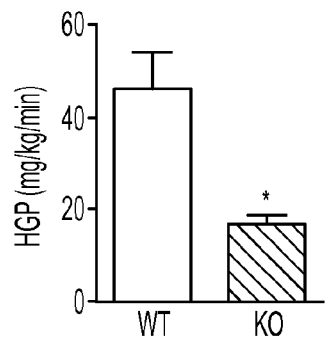
Figure 2D:
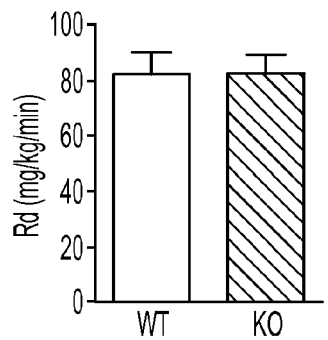
Figure 2E:
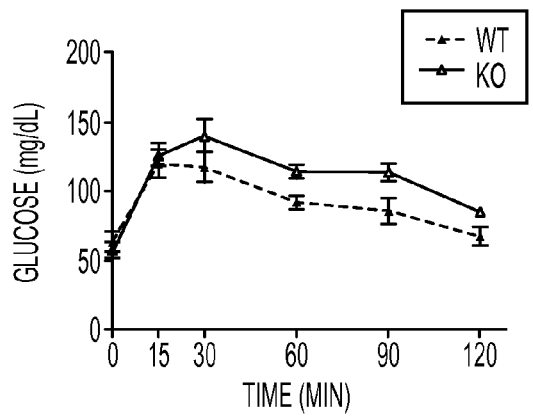
Figure 2F:
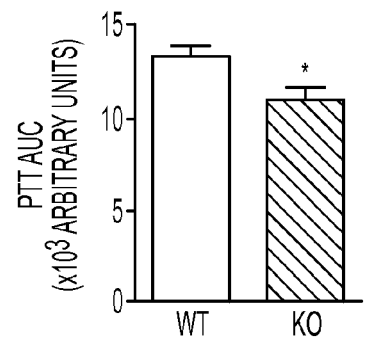

To avoid confounders due to differences in fat content (Butler and Kozak, 2010), hyperinsulinemic euglycemic clamps were performed in mice that were closely matched for body weight and composition. Agrp-Foxo1$^{-/-}$ mice had a 50% increase in glucose infusion rates (GIR) (FIG. 2B) and a 70% reduction of HGP (FIG. 2C), but comparable disposal rates (Rd) (FIG. 2D). Furthermore, when mice were challenged with pyruvate after an overnight fast, Agrp-Foxo1$^{-/-}$ mice had a significantly reduced rise in glucose levels, consistent with decreased hepatic gluconeogenesis (FIG. 2E,F). Therefore, Agrp-Foxo1$^{-/-}$ mice show altered energy partitioning during fasting and increased metabolic flexibility.

Figure 9A:
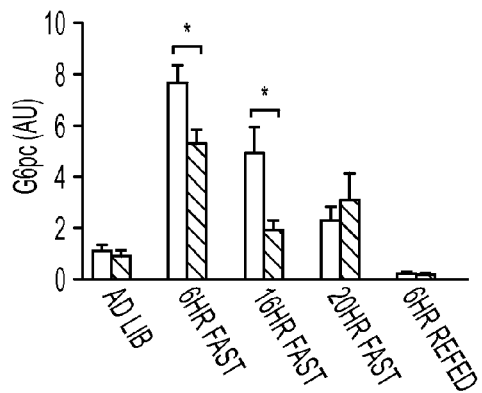
FIG. 9A-9G. ETC Liver gene expression and glycogen and lipid content. (A,B) Expression of G6pc (A) and Gck (B) in livers of Agrp-Foxo1–/– (KO) and wild-type mice (WT) under the following conditions: ad libitum-fed (WT n=5, KO n=4), 6-hr fast (WT n=7, KO n=10), 16-hr fast (WT n=7, KO n=9), 20-hr fast (WT n=6, KO n=6), 6-hr refed (WT n=8, KO n=7). (C) Hepatic glycogen content after a 16-hr fast (n=7-10 for each genotype). (D) Hepatic lipid content after a 20-hr fast. Scale bar 100 µm. (E-G) Expression of genes involved in lipid synthesis (E,F) and oxidation (G) analyzed under the same conditions and in the same groups of animals as in (A,B). Data presented as means±SEM. *=P<0.05, **=P<0.01. AU: arbitrary units.
Figure 9E:
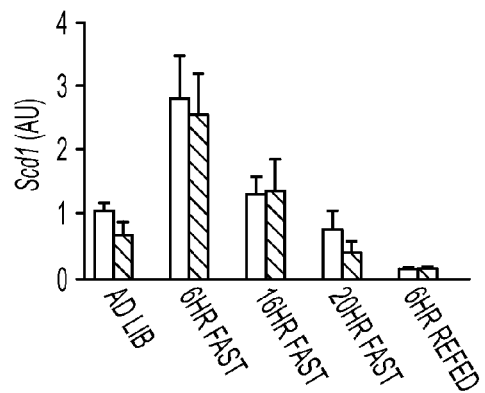
Figure 9B:
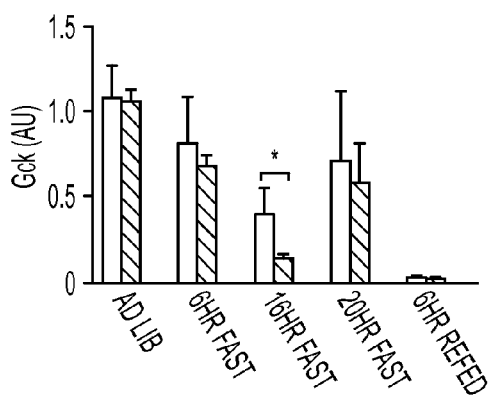
Figure 9F:
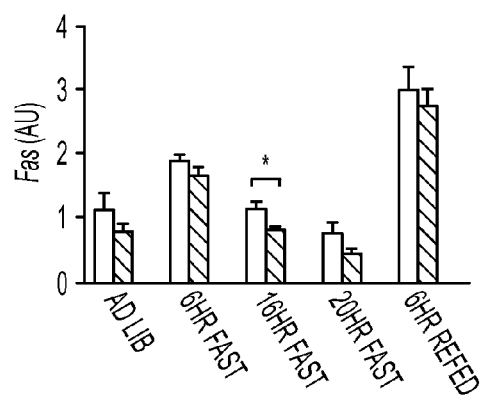
Figure 9C:
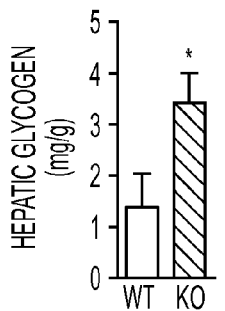
Figure 9D:
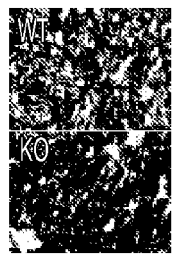
Figure 9G:
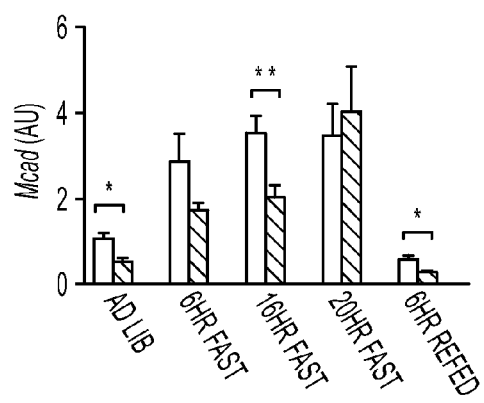

To examine mechanisms of decreased HGP, Agrp-Foxo1$^{-/-}$ mice were studied after fasting and refeeding. During fasting, mRNA levels of the gluconeogenic gene G6pc were decreased (FIG. 9A), as was glucokinase (Gck) (FIG. 9B). Phosphoenolpyruvate carboxykinase-1 (Pck1) and pyruvate dehydrogenase kinase-4 (Pdk4) remained unchanged (FIG. 10). During fasting, hepatic glycogenolysis is the main source of glucose (Lin and Accili, 2011). Consistent with decreased HGP, Agrp-Foxo1$^{-/-}$ mice had significantly increased hepatic glycogen and lipid after prolonged fasting (FIG. 9C,D). To test whether the latter was due to increased de novo hepatic lipogenesis, the expression of genes involved in fatty acid synthesis, oxidation, and mobilization were examined (FIG. 9E-G and FIG. 10). mRNAs encoding key lipogenic enzymes were either comparable to wild-type levels (FIG. 9E and FIG. 10) or slightly decreased in Agrp-Foxo1$^{-/-}$ mice (FIG. 9F and FIG. 10). In contrast, hepatic Mcad was expressed at lower levels—consistent with the possibility that fatty acid oxidation is decreased (FIG. 9G). Other genes involved in liver FFA metabolism were unchanged (FIG. 10). These data raised the possibility that the increased lipid accumulation in the liver of Agrp-Foxo1$^{-/-}$ mice was due to increased flux of FFA from adipose tissue.

Altered Adipocyte Metabolism in Agrp-Foxo1$^{-/-}$ Mice.

Figure 3A:
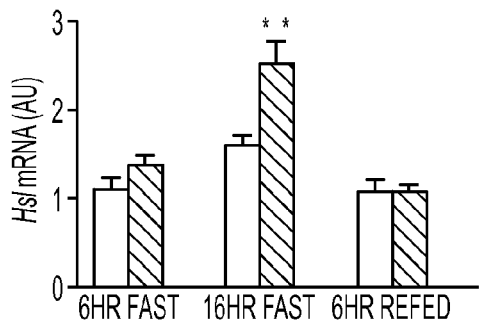
FIG. 3A-3J. Altered white adipose tissue metabolism in Agrp-Foxo1$^{-/-}$ mice. (A-C) Expression of lipolytic genes Hsl (A), Atgl (B), and Mgl1 (C) under the following conditions: 6-hr fast (WT n=7, KO n=10), 16-hr fast (WT n=7, KO n=9), 6-hr refed (WT n=8, KO n=7). (D-E) Fasting plasma NEFA and glycerol (n=7-11 for each genotype). Values are normalized by epididymal fat pad weight. (F) Fasting plasma glucagon (n=6-11 for each genotype). (G) Epididymal fat pad weight after 6-hr or 16-hr fasting (n=7-11 for each genotype). (H) Histomorphometry of epididymal adipose cells size (n=9-11 for each genotype). (I) Representative western blot and quantification of UCP1 expression in epididymal white adipose tissue (n=10 for each genotype). (J) Representative electron microscopic image illustrating larger mitochondria in epididymal adipocytes of Agrp-Foxo1$^{-/-}$ mice. Data presented as means±SEM. *=P<0.05, **=P<0.01. AU: arbitrary units.
Figure 3D:
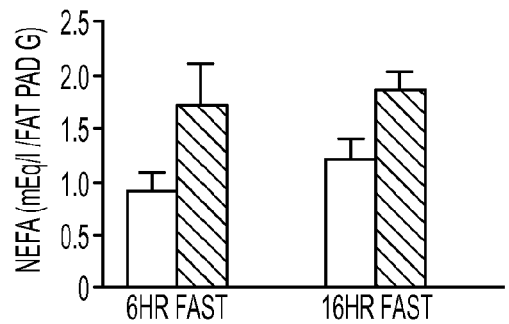
Figure 3B:
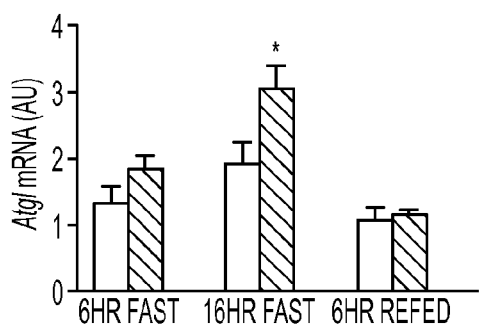
Figure 3E:
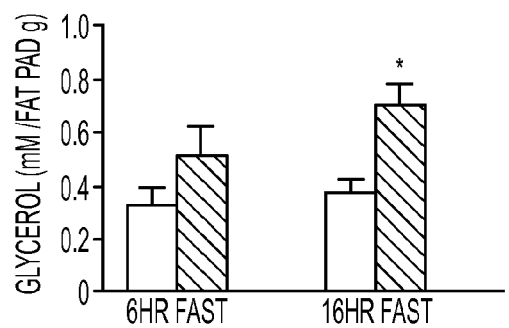
Figure 3C:
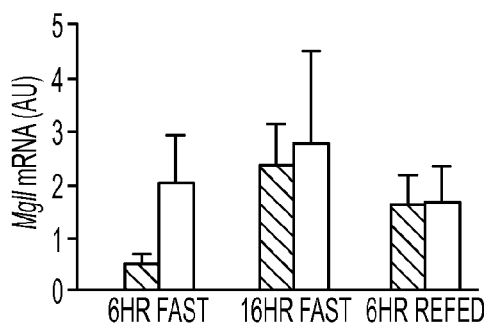
Figure 3F:
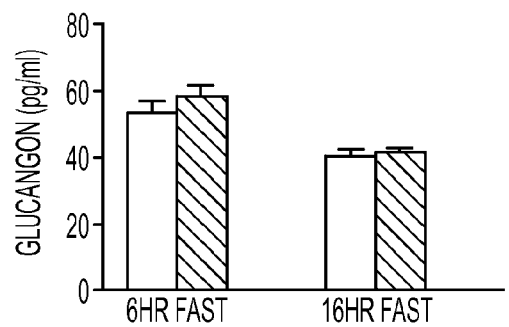
Figure 3G:
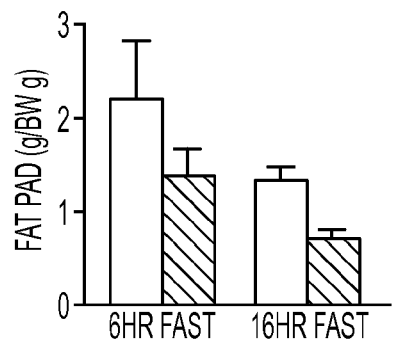
Figure 3H:
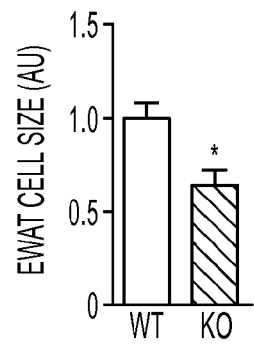
Figure 3I:
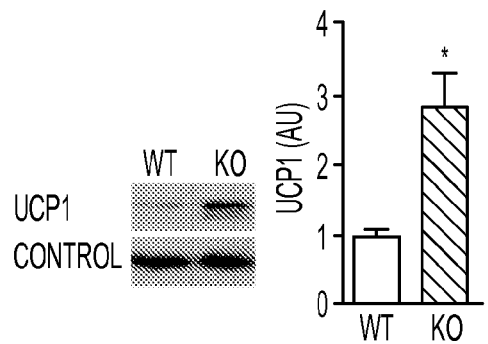
Figure 3J:

To test whether Agrp Foxo1−/− mice had an increased flux of FFA from adipose tissue, expression of lipolytic genes were examined. Both Hsl and Atgl showed significantly increased expression after an overnight fast (FIG. 3A,B), while Mgll showed a non-significant trend toward increase only at the 6-hr time point (FIG. 3C) in Agrp-Foxo1$^{-/-}$ mice. Consistently, fasting plasma FFA and glycerol were elevated (FIG. 3D,E). Glucagon levels were unchanged between control and Agrp-Foxo1$^{-/-}$ mice (FIG. 3F). Fat pad weight decreased in Agrp-Foxo1$^{-/-}$ mice (FIG. 3G), consistent with increased fasting-induced lipolysis. Histomorphometry of epididymal white adipose tissue (EWAT) demonstrated significantly smaller cells in Agrp-Foxo1$^{-/-}$ mice (FIG. 3H). Moreover, Agrp-Foxo1$^{-/-}$ mice showed increased UCP1 in EWAT (FIG. 3I). Electron microscopy revealed that EWAT from Agrp-Foxo1$^{-/-}$ mice contained larger mitochondria of normal morphology (FIG. 3J).

Increased Nutrient Signaling in CNS of Agrp-Foxo1$^{-/-}$ Mice.

The common thread in the sub-phenotypes observed in Agrp-Foxo1$^{-/-}$ mice is the dissociation between decreased food intake and reduced fasting response. These two aspects could be reconciled by increased sensitivity to hormonal and nutrient signals conveyed through AgRP neurons.

Figure 4A:
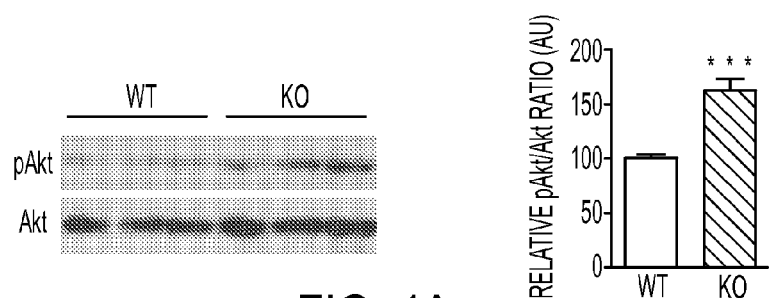
FIG. 4A-4H. Increased hypothalamic signaling by hormones and nutrients in mutant mice. (A,F) Representative western blotting and quantitative analysis on ARH protein extracts in 6-hr-fasted Agrp-Foxo1$^{-/-}$ (KO) and wild-type (WT) (A) or 4-hr-refed Agrp-Foxo1$^{-/-}$ (KO) and wild-type (WT) (F). Data presented as means±SEM. ***=P<0.001. (B-E, G-H) Representative immunohistochemistry with pSTAT3 (B,C), pAkt (D,E) and pS6 (G,H) in mice fasted overnight and refed for 3-4 hrs (n=6 for each genotype). Scale bar 100 µm.
Figure 4B:
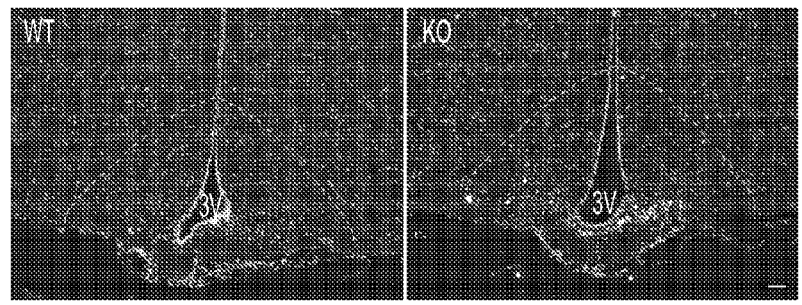
Figure 4C:
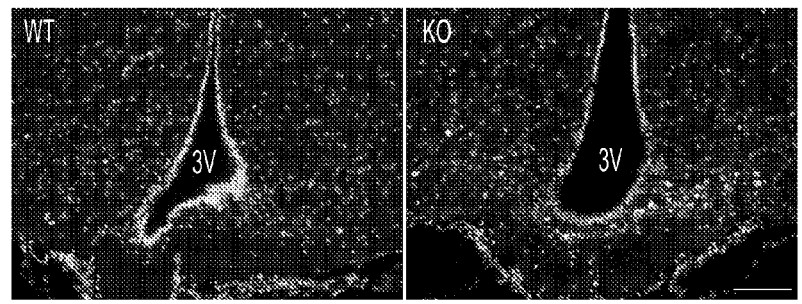
Figure 4D:
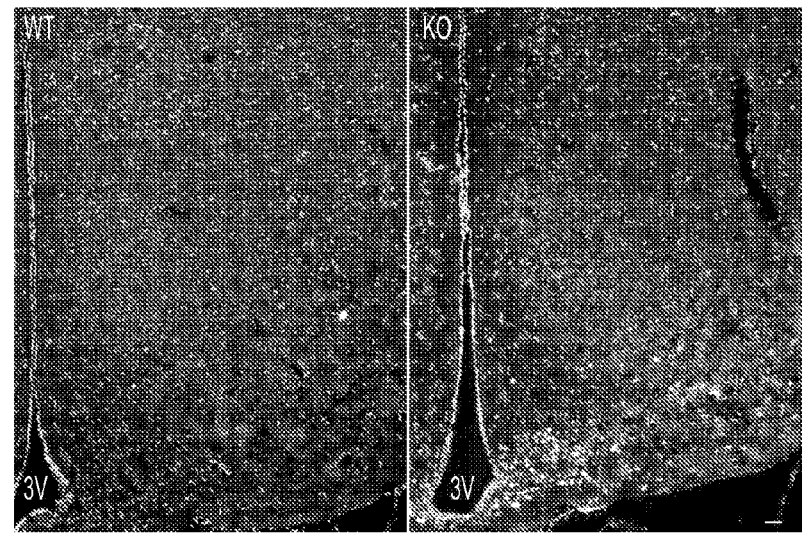
Figure 4E:
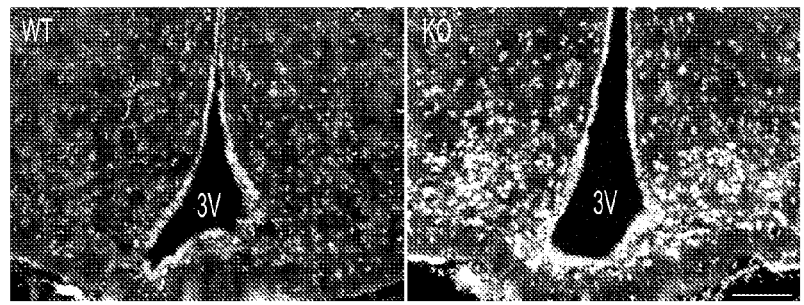
Figure 4F:
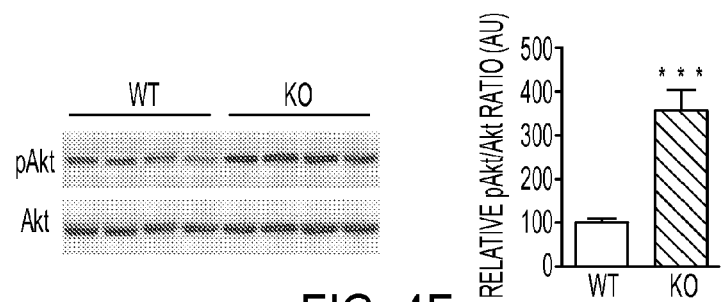
Figure 5D:
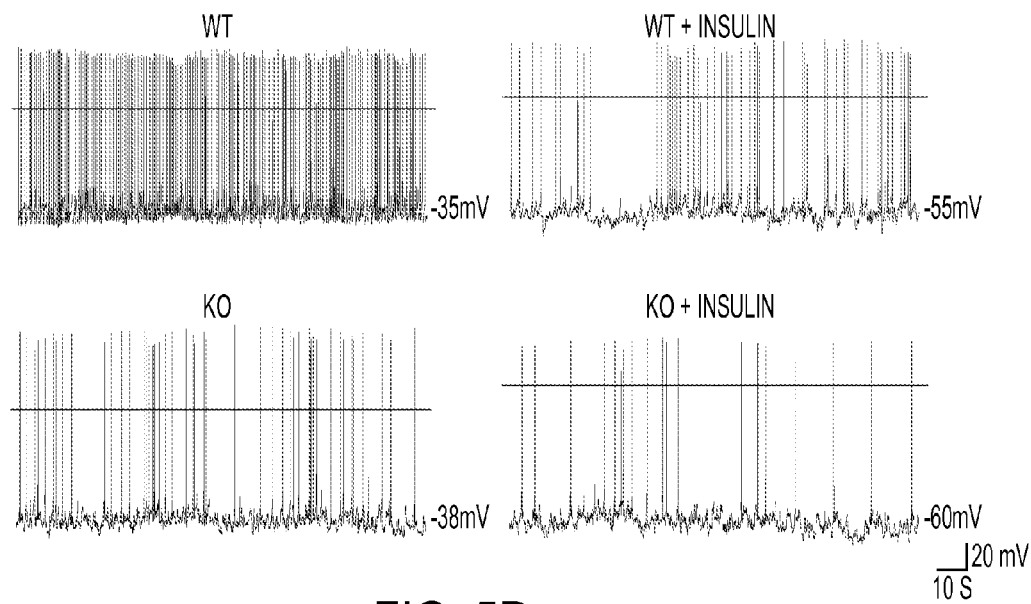
Figure 5E:
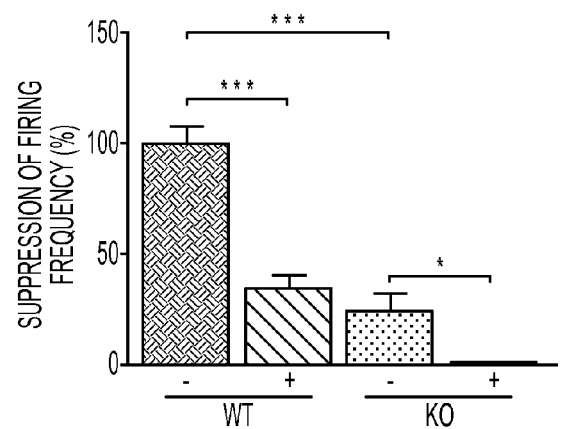
Figure 5F:
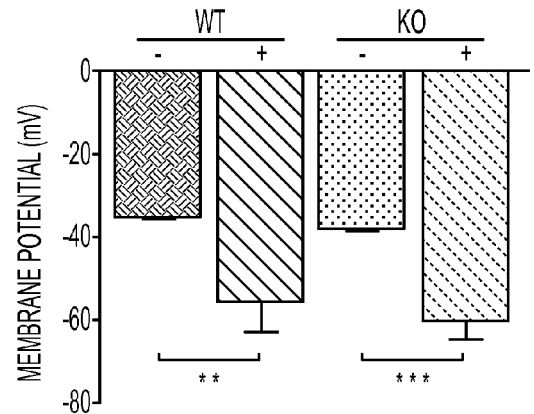
Figures 11A, 11B, 11C:
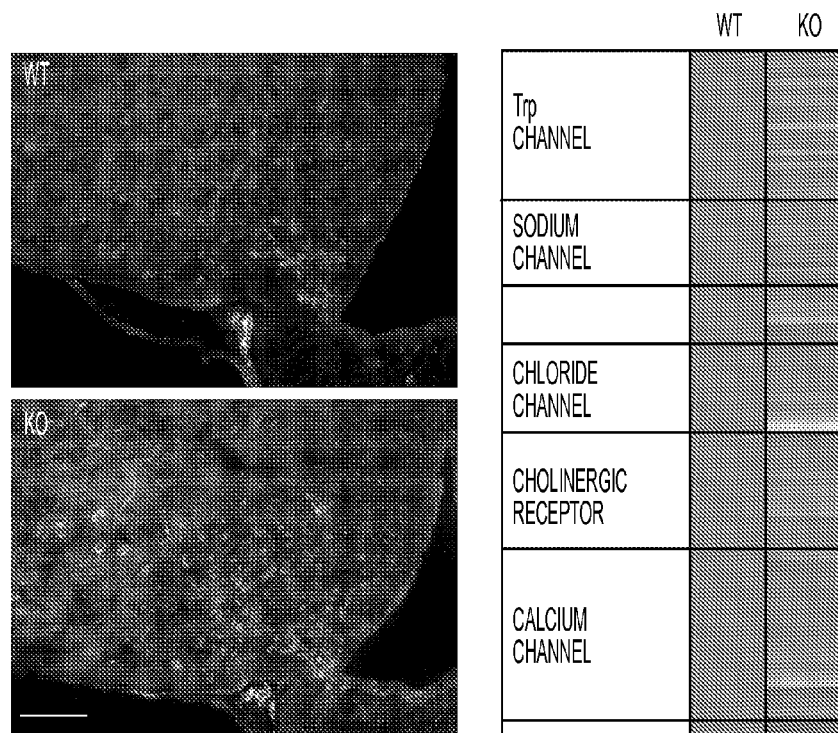
FIG. 11A-11C. Metabolic and gene expression characterization of AgRP neurons in Agrp-Foxo1−/− (KO) and wild-type (WT) mice. (A) AgRP neurons (shown by red fluorescence) in Agrp-Foxo1−/− (KO) have increased insulin sensitivity (shown by pAkt immunohistochemistry, green fluorescence) than those in wild-type (WT) mice during fasting. Scale bar 100 μm. (B,C) Gene expression heat maps of AgRP neurons from wild-type (WT) and Agrp-Foxo1−/− (KO) mice sorted based on red fluorescence (Tomato). Gene expression in KO mice was normalized to WT (value equals 1). Higher expression is marked with brighter color, while lower expression than WT is labeled with darker color.
Figure 12A:
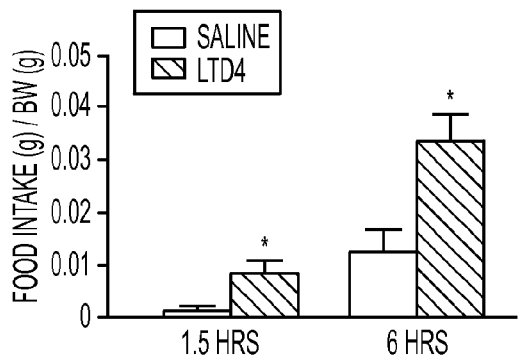
FIG. 12A-12D. Gpr17 agonist administration increases food intake and impairs neuronal regulation of glucose homeostasis. (A) Satiated mice were injected with saline or Gpr17 agonist LTD4 (n=5-7). Food intake was monitored for the following time course. (B) Locomotor activity counts of satiated mice during daytime within 1.5 hours following administration of Gpr17 agonist LTD4 (n=6). (C) After fasting for 6 hrs, saline or LTD4 were administered to the mice (n=6-7). Glucose tolerance test was performed 20 minutes after the administration. (D) Gpr17 agonist causes a sharp increase of blood glucose immediately after the administration. After fasting for 6 hrs, saline or UDP-glucose were administered to the mice (n=5-6). Glucose was measured before or 20 minutes after the administration.
Figure 12B:
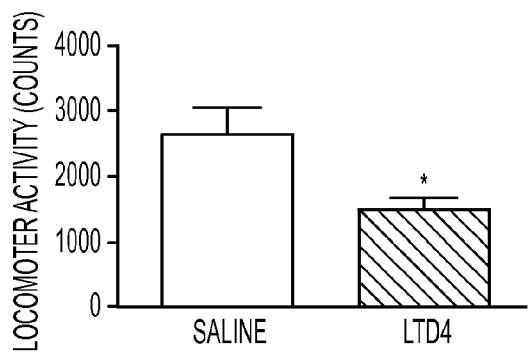
Figure 12C:
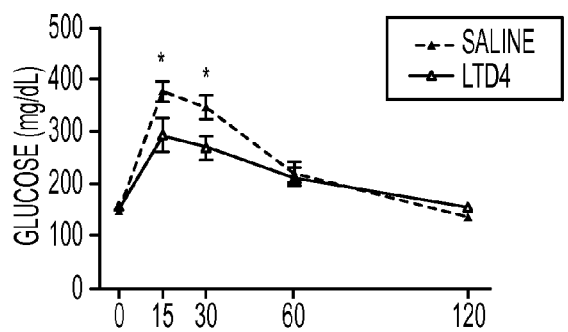
Figure 12D:
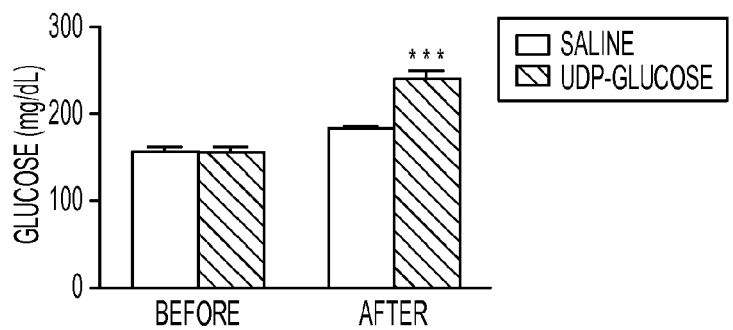

Insulin and leptin inhibit food intake (Halaas et al., 1995; Woods et al., 1979). Immunohistochemistry with phospho (p)Akt and pSTAT3, respectively, was used to examine hormonal and nutritional signaling pathways. Fasted Agrp-Foxo1$^{-/-}$ mice had increased pAkt staining in MBH that wasn't limited to AgRP neurons (red cells) (FIG. 11A). Western blots confirmed the increase of pAkt in MBH (FIG. 4A). After refeeding, despite decreased serum leptin (Table 1), Agrp-Foxo1$^{-/-}$ mice showed increased pSTAT3 staining in ARH (FIG. 4B,C) and increased hypothalamic pAkt (FIG. 4D), especially in ARH (FIG. 4E). Western blots confirmed the increase of pAkt in ARH (FIG. 4F). Therefore, knocking out Foxo1 in AgRP neurons renders mice more sensitive to leptin and insulin signaling in the hypothalamus.

Figure 4G:
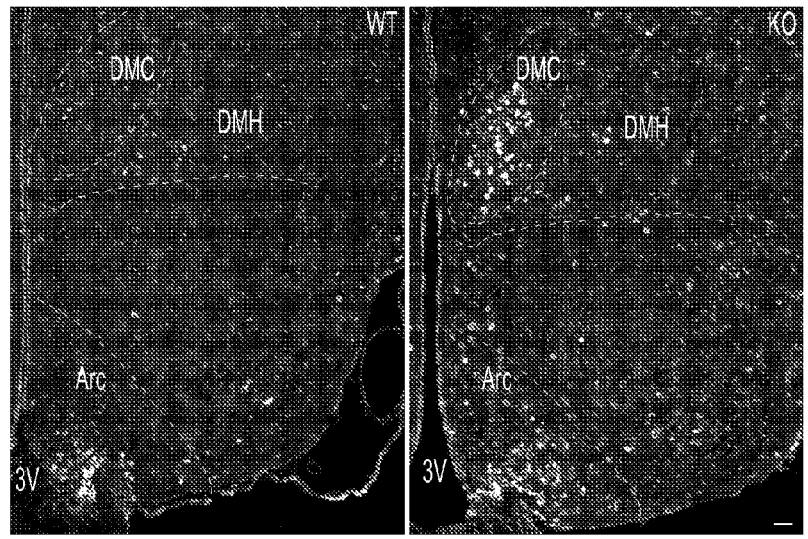
Figure 4H:
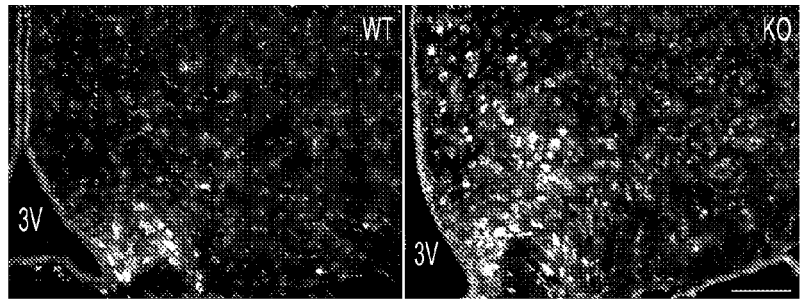

Amino acid sensing by the mTOR pathway promotes satiety (Cota et al., 2006). mTOR activity was monitored using immunohistochemistry with antibodies against its substrate ribosomal protein S6 in refed mice. ARH AgRP neurons project to DMH (Broberger et al., 1998). Agrp-Foxo1$^{-/-}$ mice showed increased pS6 staining in ARH and DMH (FIG. 4G,H). Thus, hormone and nutrient signaling is uniformly increased in Agrp-Foxo1$^{-/-}$ mice.

Example 3

Characteristics of FoxO1-Deficient AgRP Neurons

Functional and Gene Expression Analysis of FoxO1-Deficient AgRP Neurons.

To identify AgRP and Pomc neurons, Agrp-Foxo1$^{-/-}$ mice carrying Npy-Gfp (Agrp-Foxo1$^{-/-}$; Rosa-tomato; Npy-Gfp) or Pomc-Gfp transgenes (Agrp-Foxo1$^{-/-}$; Rosa-tomato; Pomc-Gfp) were generated. Foxo1-ablated AgRP neurons expressed Npy-gfp, but not Pomc-gfp (FIG. 5A). Thus, FoxO1-deficient AgRP neurons retained their neuronal identity, thereby excluding developmental defects due to trans-differentiation (Padilla et al., 2010). Next, Agrp-Foxo1$^{-/-}$; Rosa-tomato; Npy-Gfp mice were used to flow-sort green Npy neurons and red AgRP neurons. FACS analysis demonstrated that 100% of AgRP neurons (labeled by tomato in red) (FIG. 5B) are also Gfp-positive (i.e., they express Npy-Gfp). Having thus validated the FACS approach, mRNA were isolated from AgRP neurons of wild-type (Foxo1$^{loxP/+}$; Agrp-Cre; Rosa-tomato) and Agrp-Foxo1$^{-/-}$; Rosa-tomato mice (FIG. 5C) and performed transcriptome profiling. Gene set enrichment analysis of the microarray data demonstrated increased expression of genes encoding components of the electron transport chain, translation, generation of precursor metabolites and energy, mitochondrial genome maintenance, and cellular component biogenesis in FoxO1-deficient AgRP neurons (Table 2 and FIG. 11B). This anabolic gene expression profile of the mutant neurons is consistent with a state of increased energy availability, as one would predict based on increased insulin, leptin, and mTOR signaling (FIG. 4). In other words, FoxO1-deficient AgRP neurons display gene expression patterns consistent with a state of energy sufficiency.

The electrophysiological properties of AgRP neurons identified using fluorescent reporters in brain slices from wild-type and Agrp-Foxo1$^{-/-}$ mice (FIG. 5D-F) were studied. Under basal conditions, FoxO1-deficient AgRP neurons had significantly lower membrane potential and firing frequency. Furthermore, insulin suppressed the firing frequency of wild-type cells to ~35% of basal level, a nearly three-fold reduction. Despite the lower basal firing frequency, insulin further suppressed the firing frequency of knockout neurons, with a 100-fold reduction. Insulin caused a similar reduction in membrane potential in wild-type and knockout cells (~−20 mV). Therefore, the electrophysiological data are consistent with the physiologic and signaling findings in Agrp-Foxo1$^{-/-}$ mice, indicating that knockout neurons are more insulin-sensitive.

Expression of ion channels and neurotransmitter receptors (Table 3 and FIG. 11C) were studied. Of note, most GABAergic receptors showed increased expression, indicating that GABAergic activity is increased, whereas most glutaminergic receptors were expressed at lower levels in FoxO1-deficient AgRP neurons, indicating that glutaminergic signaling is decreased. To provide a functional validation of the mRNA measurements, electrophysiological responses of AgRP neurons identified in brain slices from control and Agrp-Foxo1$^{-/-}$ mice were studied. Mini excitatory post-synaptic currents (mEPSC) are typically mediated by glutaminergic neurotransmitters, while mini inhibitory post-synaptic currents (mIPSC) are elicited by GABAergic neurotransmitters (Pinto et al., 2004). FoxO1-ablated AgRP neurons showed a significant reduction of mEPSC peak amplitude (FIG. 5G), but no change in frequency (data not shown). Conversely, they showed a significant increase of peak amplitude and size distribution of mIPSC (FIG. 5H), without significantly altered frequency (data not shown). Therefore, the electrophysiological findings corroborate the results from gene expression profiling and indicate that Foxo1 ablation in AgRP neurons leads to increased GABAergic and decreased glutaminergic responses, as might be expected from altered neurotransmitter receptor expression at the post-synaptic level. Pre-synaptic plasticity of Npy neurons in ob/ob mice is modulated by acute exposure to leptin (Pinto et al., 2004). The changes at the post-synaptic level could partly contribute to or reflect adaptive consequences of the anorexigenic phenotype in Agrp-Foxo1$^{-/-}$ mice.

Example 4

Gpr17 and FoxO1 in AgRP Neurons

G Protein-Coupled Receptor Gpr17 is a FoxO1 Target in AgRP Neurons.

Given the favorable metabolic profile of Agrp-Foxo1$^{-/-}$ mice, experiments were designed to identify FoxO1 targets that mediate its effects and are readily targetable by chemical means. Microarray analysis indicated that mRNA encoding the G protein-coupled receptor, Gpr17, was profoundly decreased in flow-sorted FoxO1-deficient AgRP neurons. Neurons were labeled with Rfp by intercrossing Synapsin-Cre and Rosa-tomato mice, then flow-sorted neuron and non-neuron populations and measured Gpr17 levels. qPCR analysis showed that Gpr17 is overwhelmingly enriched in neurons (FIG. 6A). Next, Gpr17 regulation in ARH punch biopsies from fasted and refed mice was examined. Gpr17 was expressed at significantly higher levels during fasting (FIG. 6B). To investigate the function of Gpr17 in AgRP neurons, the electrophysiological properties of fluorescently labeled AgRP neurons in response to the Gpr17 antagonist, cangrelor were tested. Upon treatment with cangrelor, AgRP neurons showed significantly reduced firing frequency and lower membrane potential (FIG. 6C-E). Therefore, inhibition of Gpr17 can affect the electrical activity of AgRP neurons in an insulin-mimetic fashion, supporting our hypothesis.

Consistent with the microarray data, Gpr17 expression in FoxO1-deficient AgRP neurons (FIG. 6F) was dramatically reduced (18-fold over control) (FIG. 6G). Gpr17 levels are extremely high in AgRP neurons, being comparable to β-actin (qPCR Ct=18.44±0.02 vs. 20.61±0.06 for β-actin and Gpr17, respectively). Foxo1, in contrast, is considerably less abundant (Ct=23.43±0.03).

Potential FoxO1 binding sites were identified by analyzing the mouse Gpr17 promoter. Accordingly, chromatin immunoprecipitation (ChIP) assays showed that FoxO1 binds to the Gpr17 promoter (FIG. 6H).

Furthermore, quantitative analysis of the ChIP data indicated a 40-fold enrichment of the FoxO1 ChIP compared with IgG controls, indicating that binding is extremely robust. Thus, Gpr17 is a direct FoxO1 target.

Cultured Neuro2A cells were used to test the role of FoxO1 in Gpr17 regulation. Endogenous Foxo1 and Gpr17 are expressed at low levels in this cell line. Transfection of either wild-type FoxO1-Gfp or constitutively active FoxO1 (FoxO1-ADA, in which the key phosphorylation sites have been mutated by prevent FoxO1 inactivation) (Nakae et al., 2003) significantly increased Gpr17 levels (FIG. 6I).

Example 5

Gpr17 Agonists Increase Appetite while Gpr17 Antagonists Reduce Appetite

Opposing Actions of GPR17 Agonists and Antagonists on AgRP Neuron Signaling and Food Intake In Vivo.

To test whether Gpr17 function affects ARH hormonal signaling in vivo, cangrelor was delivered directly into the 3$^{rd}$ ventricle of mice after an overnight fast and the co-localization of pSTAT3, pS6, and pAkt was determined in either POMC or AgRP neurons, identified by fluorescent reporter, after refeeding. Cangrelor treatment specifically and dramatically increased pSTAT3 content in AgRP neurons, but not in POMC neurons (FIG. 7A, compare yellow fluorescence in the third row, and lack thereof in the second row). Cangrelor also increased pAkt (FIG. 7B, third row) and pS6 (FIG. 7C, third row) in a subset of AgRP neurons, without effecting detectable changes in POMC neurons, as indicated by the dearth of yellow merged fluorescence in the POMC neuron panels (FIG. 7B,C, second row panels). This striking result indicates that Gpr17 antagonism can directly and specifically increased pSTAT3 content in AgRP neurons in vivo, with lesser increases in pS6 and pAkt. The specificity of the effect of cangrelor in AgRP neurons may be related to the fact that Gpr17 mRNA is exceedingly abundant in this cell type.

The effect of delivering cangrelor into the 3$^{rd}$ ventricle of mice on food intake was studied. In wild-type mice, a significant decrease of food intake was detected starting 1 hr after re-feeding (FIG. 7D). Consistent with previous data (FIG. 2), Agrp-Foxo1$^{-/-}$ mice had a significantly decreased re-feeding intake during the same period of time that was completely unaffected by cangrelor administration.

Figure 7F:
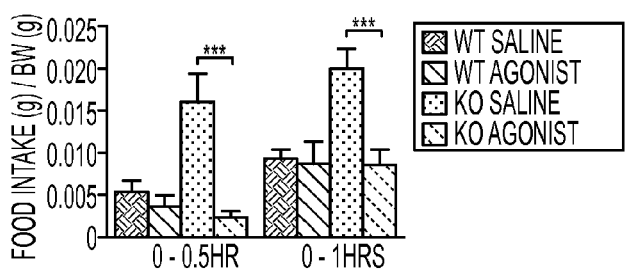
Figure 7G:
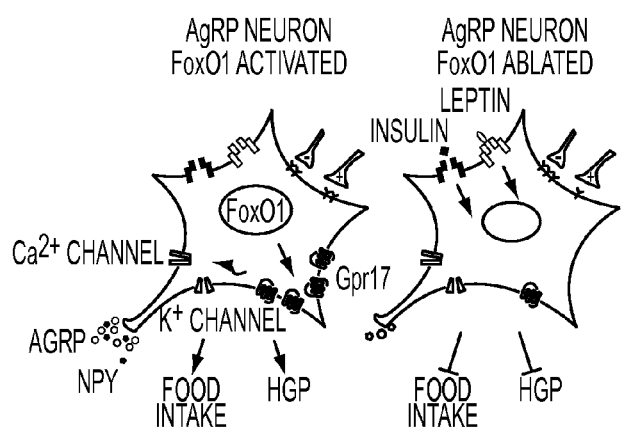

Next, the consequences of activating Gpr17 in vivo were studied. First, LTD4 was delivered directly into the 3$^{rd}$ ventricle of mice after an overnight fast and the co-localization of pSTAT3 was determined in AgRP neurons after refeeding. LTD4 treatment decreased pSTAT3 content in AgRP neurons (FIG. 7E, compare yellow fluorescence in the first and second row, and lack thereof in the third row). Second, based on data indicating a synergistic effect of the two classes of Gpr17 ligands—purines and leukotrienes—on Gpr17 signaling (Daniele et al., 2011) UDP-Glucose and LTD4 was directly infused into the 3$^{rd}$ ventricle of satiated mice and measured food intake was measured. Activating Gpr17 by this approach rapidly induced food intake in wild type, but not in Agrp-Foxo1$^{-/-}$ mice (FIG. 7F). Thus, functional data support the hypothesis that Gpr17 is a direct FoxO1 target, and that its decreased expression mediates—at least partly—the anorexigenic phenotype of Agrp-Foxo1$^{-/-}$ mice.

Example 6

Knocking Out FoxO Reduced Gpr17, which was Discovered to Contribute to Diabetes

More experiments were conducted to study the in vivo regulation of Gpr17 expression by FoxO1. It was discovered that Knocking out FoxO using Synapsin-Cre in mediobasal hypothalamus (MBH) caused a concomitant reduction of Gpr17, further showing that Gpr17 is the endogenous target of FoxO. FIG. 13, panel A. Moreover, Gpr17 expression was elevated in the hippocampus of insulin resistant diabetic GIRKO mice. FIG. 13, panel B. Further studies of Gpr17 expression showing that it contributes to the causality of diabetes, were conducted using Neuro2A (N2A) cells that express minimal endogenous Gpr17. Wild type N2A cells (treated with or without cangrelor) were serum starved overnight and then stimulated with insulin. Insulin signaling activity was gauged by measuring pAkt by western blot. It was shown that antagonizing Gpr17 using cangrelor had minimal effect on insulin signaling in wild type N2A cells. FIG. 14. These results show that N2A cells are a suitable model to study the physiological consequences of Gpr17 overexpression and the molecular mechanisms of Gpr17 signaling.

Figure 16:
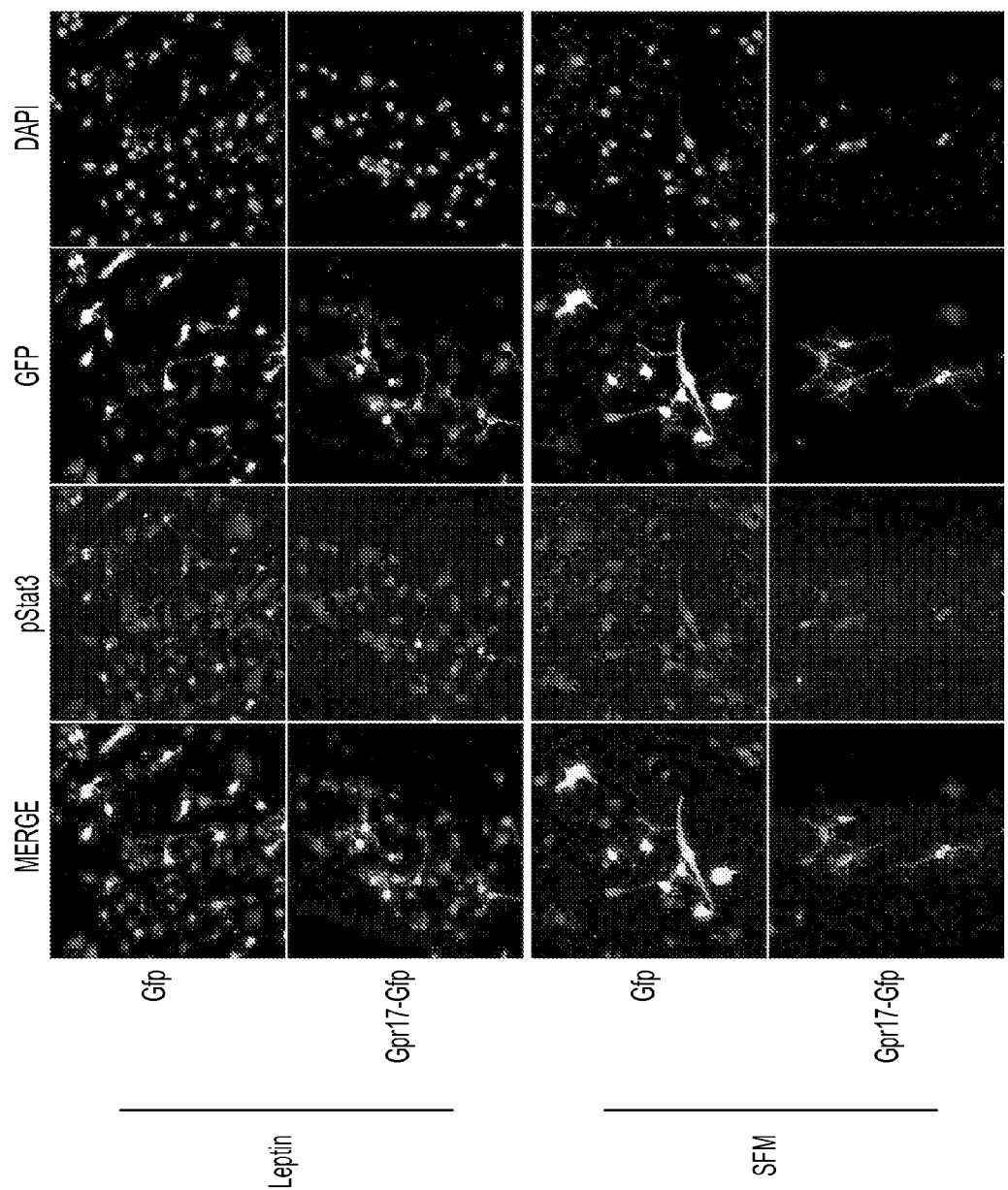
FIG. 16. Gpr17 reduces leptin signaling in N2A cells. N2A cells were transfected with control or Gpr17-Gfp construct and leptin signaling activity was measured by pSTAT3 staining (red color). N2A cells transfected with Gpr17-Gfp have reduced pSTAT3 in response to leptin stimulation, showing Gpr17 directly antagonizes leptin signaling.

It was discovered that Gpr17 reduced insulin signaling in N2A cells transfected with a control or Gpr17-Gfp construct by measuring pAkt. N2A cells transfected with Gpr17-Gfp had reduced pAkt in response to insulin stimulation, showing that Gpr17 directly antagonized insulin signaling. FIG. 15. N2A cells (expressing LepRb) transfected with Gpr17-Gfp had reduced leptin signaling activity that was shown by reduced pSTAT3 staining in response to leptin stimulation. Thus, Gpr17 directly antagonized leptin signaling in N2A cells. FIG. 16

Figure 17:
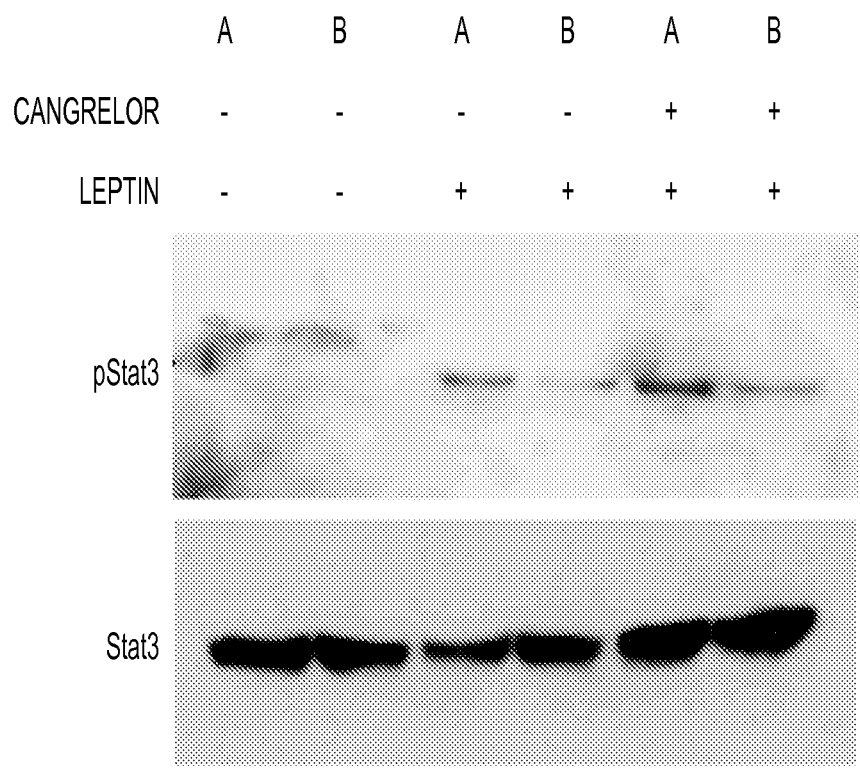
FIG. 17. Gpr17 reduces leptin signaling in N2A cells. N2A cells were transfected with control or Gpr17-Gfp construct. Leptin signaling activity was measured by pSTAT3 western blot. N2A cells transfected with Gpr17-Gfp have reduced pSTAT3 in response to leptin stimulation, suggesting Gpr17 directly antagonizes leptin signaling.

Gpr17 reduces leptin signaling in N2A cells transfected with control or Gpr17-Gfp construct was measured by pSTAT3 USING western blot. N2A cells transfected with Gpr17-Gfp have reduced pSTAT3 in response to leptin stimulation, suggesting Gpr17 directly antagonizes leptin signaling. FIG. 17.

Figure 18A:
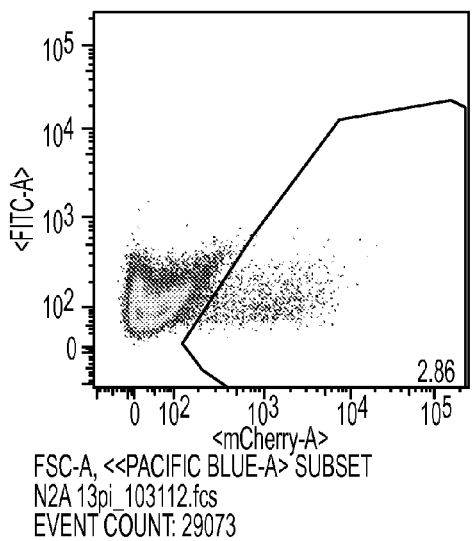
FIG. 18A-18E. Enriching Gpr17-mCherry expressing cells by flow cytometry. N2A cells were transduced with Gpr17-mCherry and were sorted based on red fluorescent marker mCherry. Population segregation and histogram were shown in (A) and (B), respectively. mCherry positive cells (2.86% of total population) from the initial sort were propagated and sorted again. Population segregation and histogram were shown in (C) and (D), respectively. Histogram (E) was generated by superimposing (B) and (D).
Figure 18C:
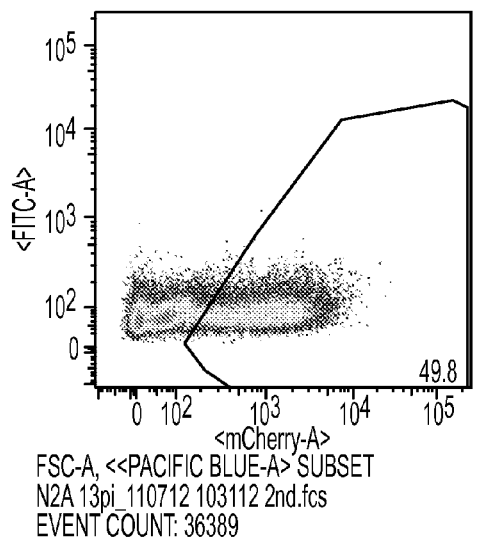
Figure 18B:
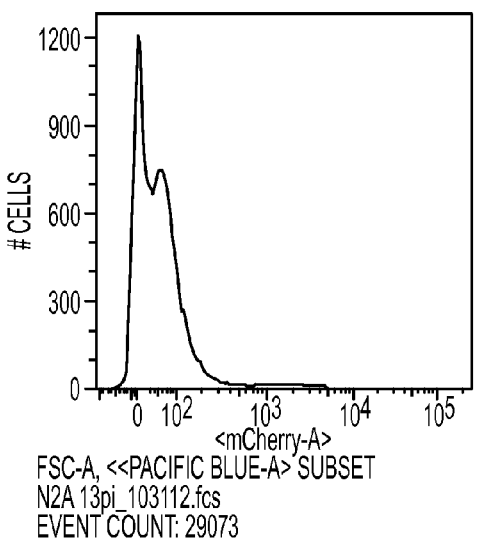
Figure 18D:
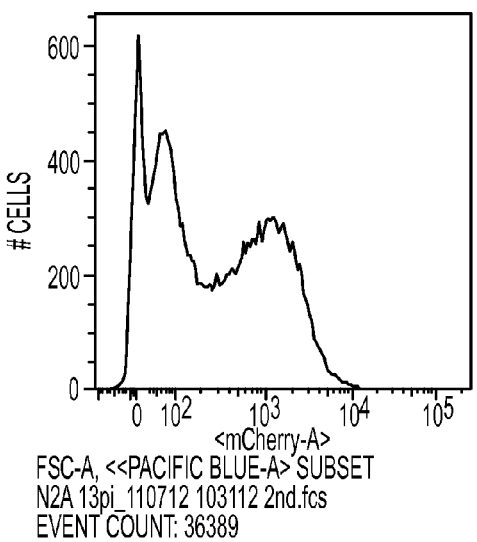
Figure 18E:
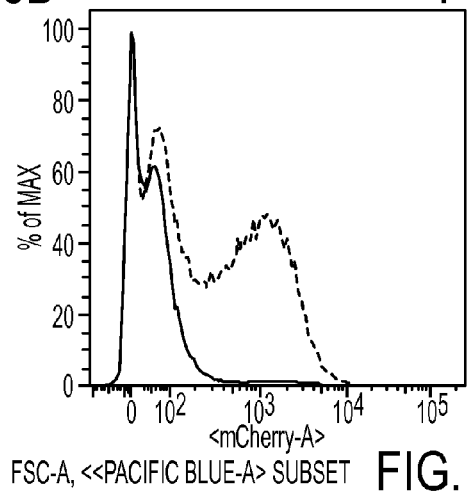

Further studies on insulin signaling were facilitated by obtaining a population of cells enriched in Gpr17-mCherry-expressing N2A cells by flow cytometry. FIG. 18A and FIG. 18B show population segregation and histograms, respectively. mCherrry positive cells (2.86% of total population) from the initial sort were propagated and sorted again as is shown in population segregation and histogram FIGS. 18, C and D, respectively. Histogram E was generated by superimposing B and D.

Figure 19:
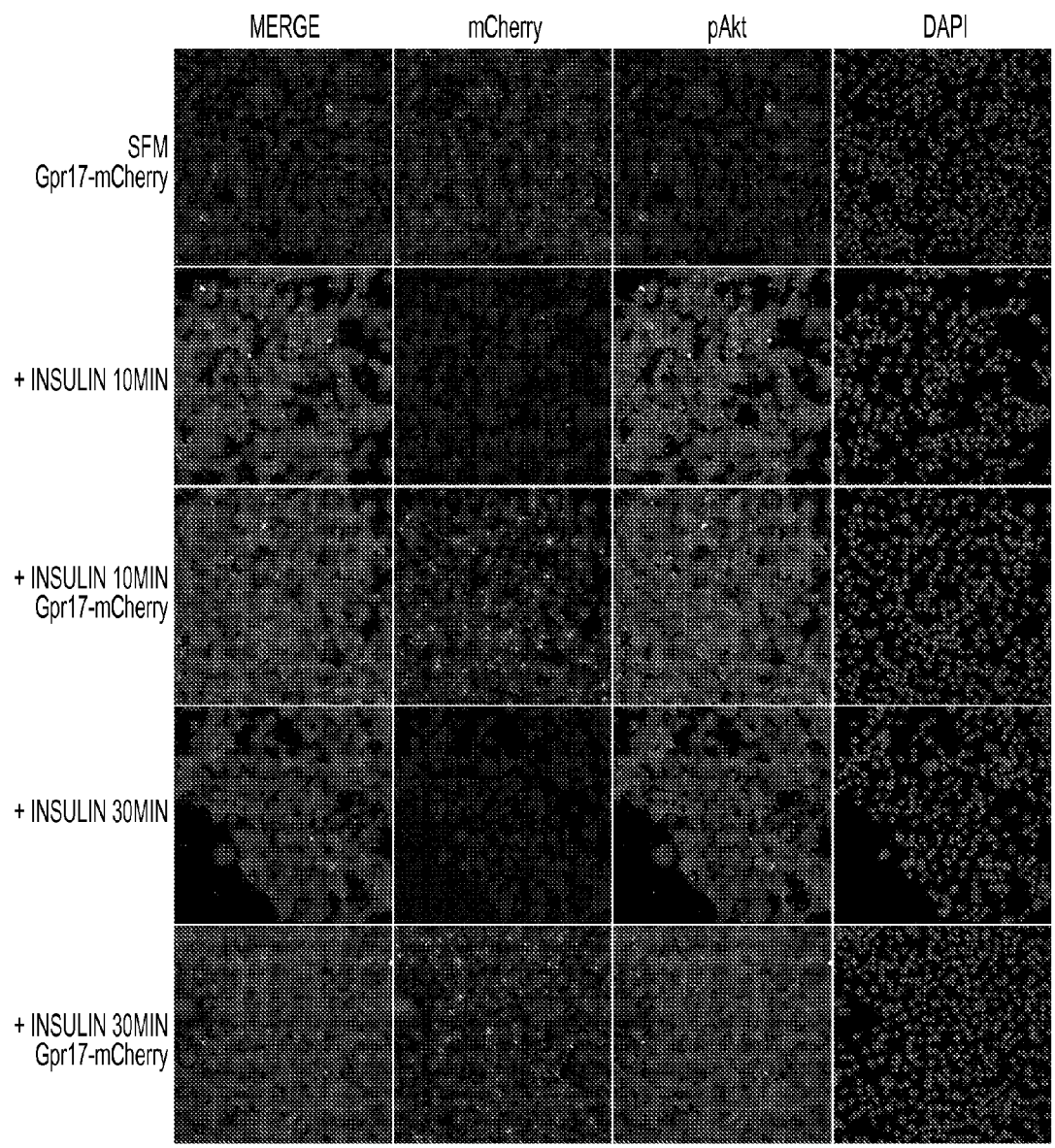
FIG. 19. Testing the insulin signaling activity using Gpr17-mCherry stable line. Ten minutes after insulin treatment, Gpr17-mCherry cells had less plasma membrane-localized pAkt compared with wild type cells. 30 minutes after insulin treatment, both Gpr17-mCherry and wild type cells have diminished pAkt staining.

Insulin signaling activity was studied using the Gpr17-mCherry N2A stable line. Wild type N2A cells and Gpr17-mCherry cells were serum starved overnight and then treated with insulin for a various durations of time, while control cells stayed in serum free medium (SFM) (i.e. without insulin stimulation). Insulin-induced pAkt was visualized by staining (green fluorescence), and Gpr17-mCherry cells were identified by red fluorescence. 10 min after insulin treatment, Gpr17-mCherry cells had less plasma membrane-localized pAkt compared with wild type cells. 30 min after insulin treatment, both Gpr17-mCherry and wild type cells had diminished pAkt staining. This result shows that Akt activation peaked 10 minutes after insulin stimulation shown by the clear plasma membrane staining. However, Gpr17-mCherry cells have less intense plasma membrane pAkt staining. FIG. 19.

Figure 20:
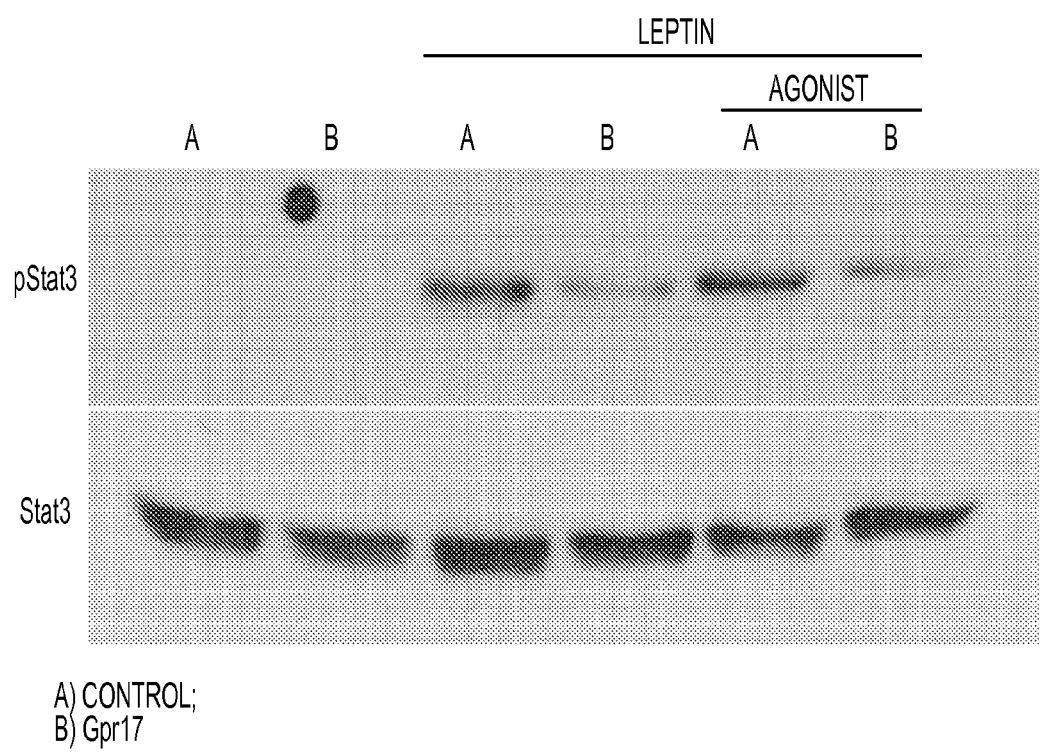
FIG. 20. Gpr17 (without Gfp tag) function reduces leptin signaling. Control or Gpr17-expressing cells were treated with leptin and leptin signaling activity was measured by pSTAT3 western blot.

To study the effect of Gpr17 (without Gfp tag) on leptin signaling, control or Gpr17-expressing cells were treated with leptin and leptin signaling activity was measured by pSTAT3 western blot. FIG. 20. The result showed that overexpressing Gpr17 caused the reduction of pSTAT3 as overexpressing the tagged Gpr17 (e.g. Gpr17-Gfp). The conclusion is that Gpr17 overexpression is the cause of reduced leptin sensitivity.

Figure 21:
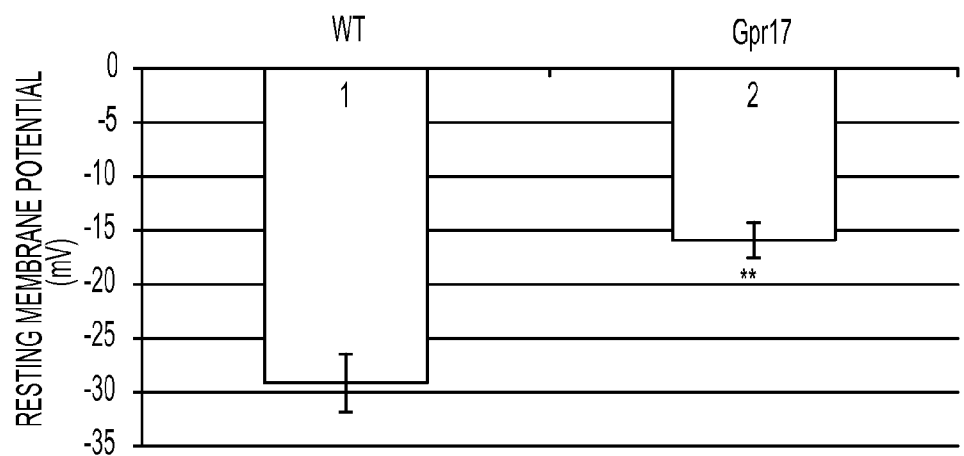
FIG. 21. Gpr17 increases neuronal cell line membrane potential. Resting membrane potential (RMP) was measured in wild type (WT) and Gpr17-mCherry stable line (Gpr17). Gpr17-mCherry cells have significantly increased RMP ($p<0.01$).
Figure 22:
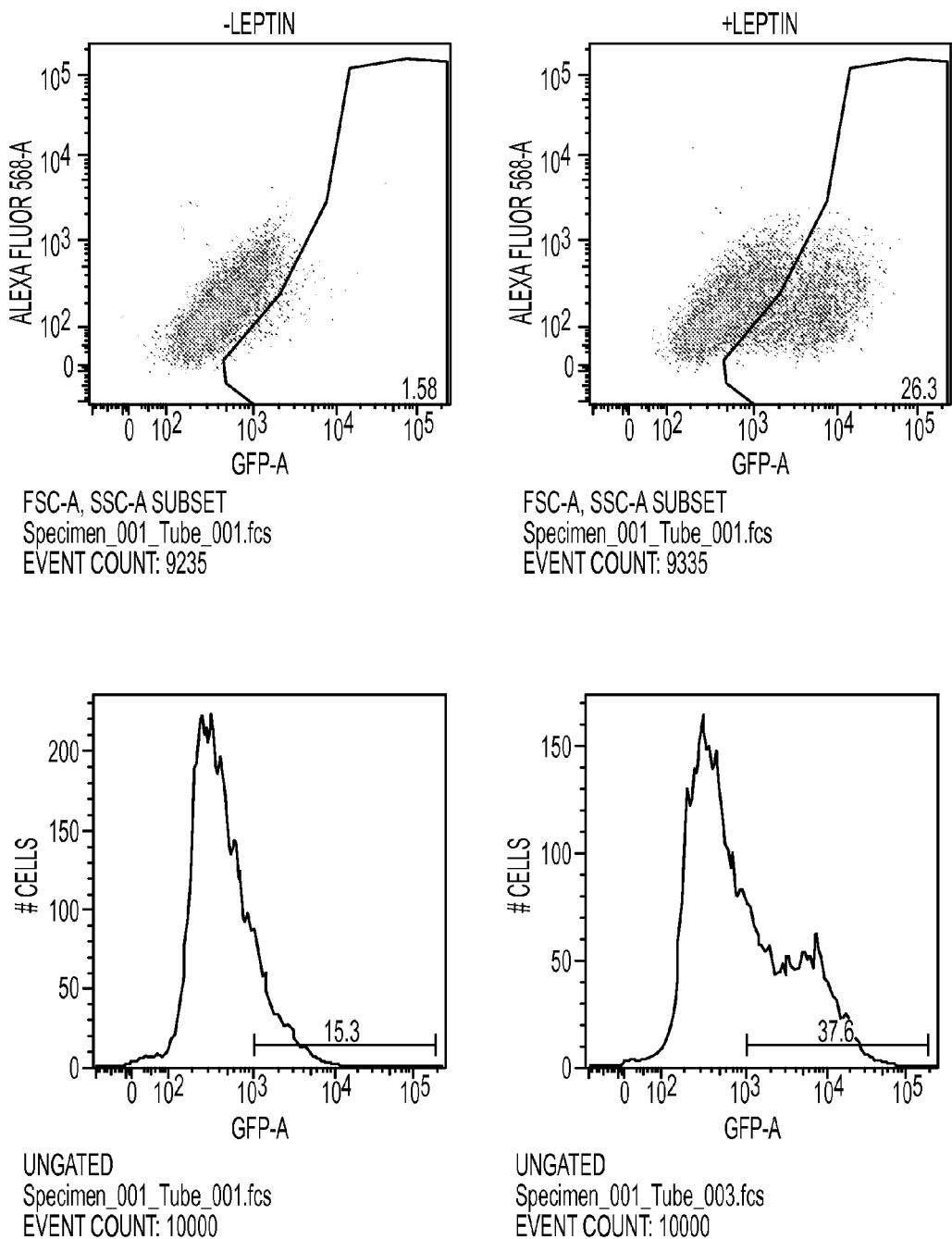
FIG. 22. Quantification of pSTAT3 positive cells by FACS. N2A cells were transfected with leptin receptor and stimulated with (+ leptin) or without leptin (− leptin). Cellular pSTAT3 signal was analyzed by FACS. pSTAT3 positive cells can be identified from the total population (upper panel). The percentage of pSTAT3 positive cells can be quantified by graphing histogram (lower panel).

Experiments were designed to quantify pSTAT3-positive cells by FACS using N2A cells transfected with leptin receptor and were either stimulated with (+ leptin) or not (− leptin). FIG. 22. The results showed that pSTAT3 can be effectively quantified by FACS, which has the potential of being an automated screening platform. Furthermore, overexpressing Gpr17 directly increased neuronal cell line membrane potential. Resting membrane potential (RMP) in Gpr17-mCherry stable line (Gpr17) was significantly increased compared to wild type (WT) cells. (p<0.01). FIG. 21.

Figure 23:
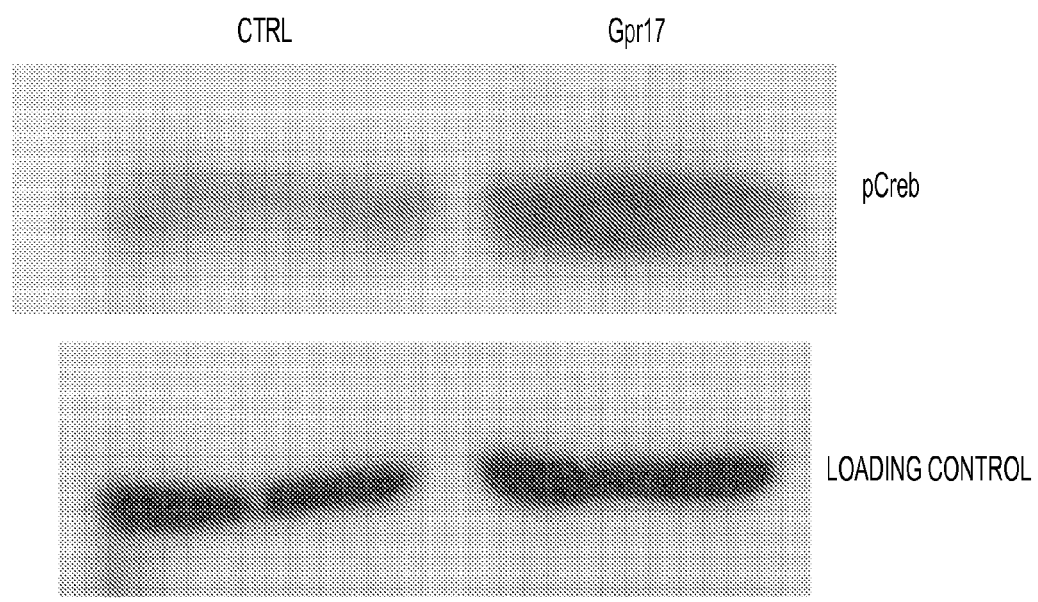
FIG. 23. pCreb as an alternative readout for quantifying Gpr17 signaling activity. Creb can be activated by cAMP generated downstream of GPCR signaling. Thereby it may serve as a readout for GPCR signaling. N2A cells with or without Gpr17 expression was serum starved. pCreb was measured by western blot.

In other experiments, pCreb was measured as an alternative readout for quantifying Gpr17 signaling activity as Creb can be activated by cAMP generated downstream of GPCR signaling. N2A cells with or without Gpr17 expression were serum starved and pCreb was measured by western blot. FIG. 23. The results showed that Gpr17 can modulate Creb phosphorylation possibly through cAMP production. Neuronal cells respond to insulin and leptin signaling by increased Akt and Stat3 activation, respectively (i.e., increased pAkt and pSTAT3). Increased Gpr17 expression in neuronal cells directly correlates with reduced pAkt or pSTAT3 after insulin or leptin stimulation. Collectively, these studies show that Gpr17 interferes with insulin and leptin signaling.

Figure 24:
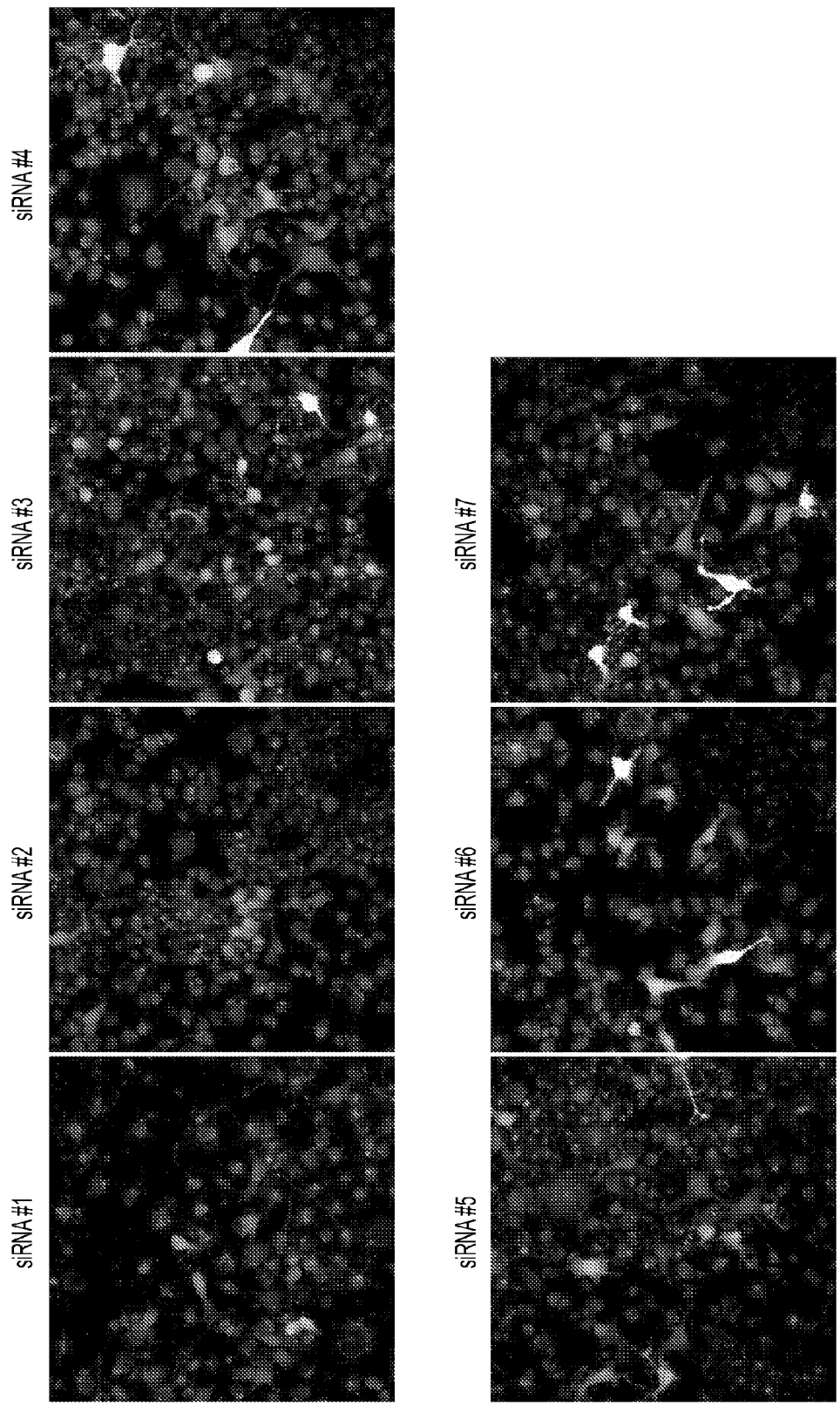
FIG. 24. Screening candidate siRNA sequences for knocking down Gpr17. Images showing the Gpr17-mCherry stable line (red) expressing the seven RNAi constructs, express Gfp (green) simultaneously.

In another series of experiments, siRNA sequences that knock down Gpr17 were identified. Seven candidate siRNA sequences conjugated to Gfp (green) and directed against mouse Gpr17 were cloned into a vector and their ability to inhibit Gpr17 expression was determined in Gpr17-mCherry stable line by their effectiveness in diminishing red fluorescence. Images showing the Gpr17-mCherry stable line (red) expressing the Gfp-7 RNAi constructs are shown in FIG. 24. Seven candidate sequences against mouse Gpr17 were cloned into vector. The resultant adenovirus expresses RNAi upon Cre-dependent recombination. Various degrees of knockdown of Gpr17 were achieved using siRNA. The most effective siRNA sequences are SEQ ID Nos. 6, 7 and 9.

Figure 25:
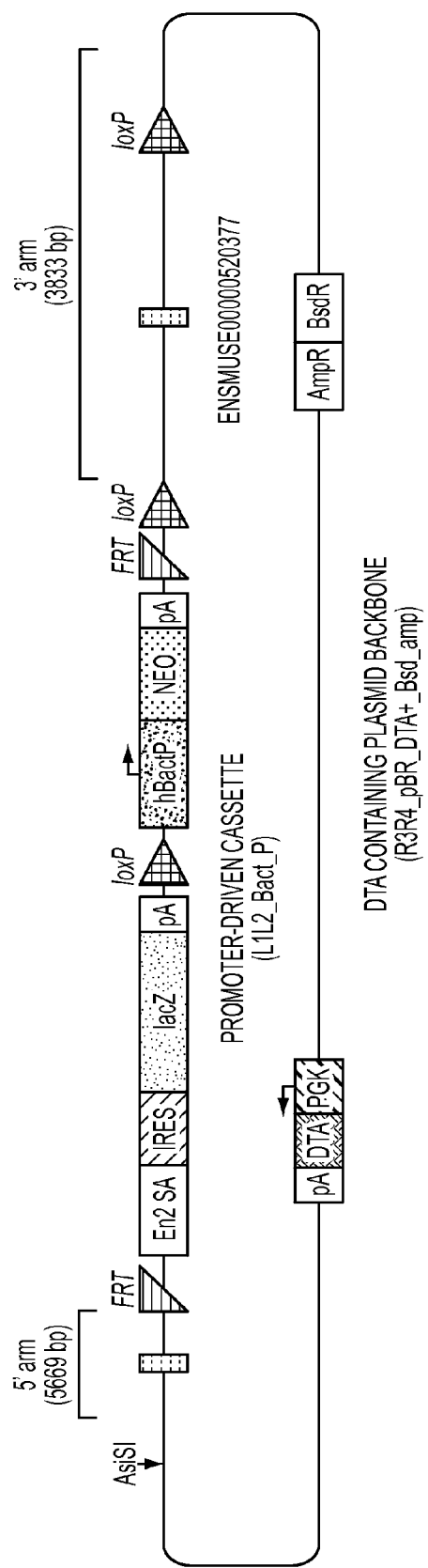
FIG. 25. Schematic showing Gpr17 conditional allele targeting vector (purchased from KOMP).
Figure 26:
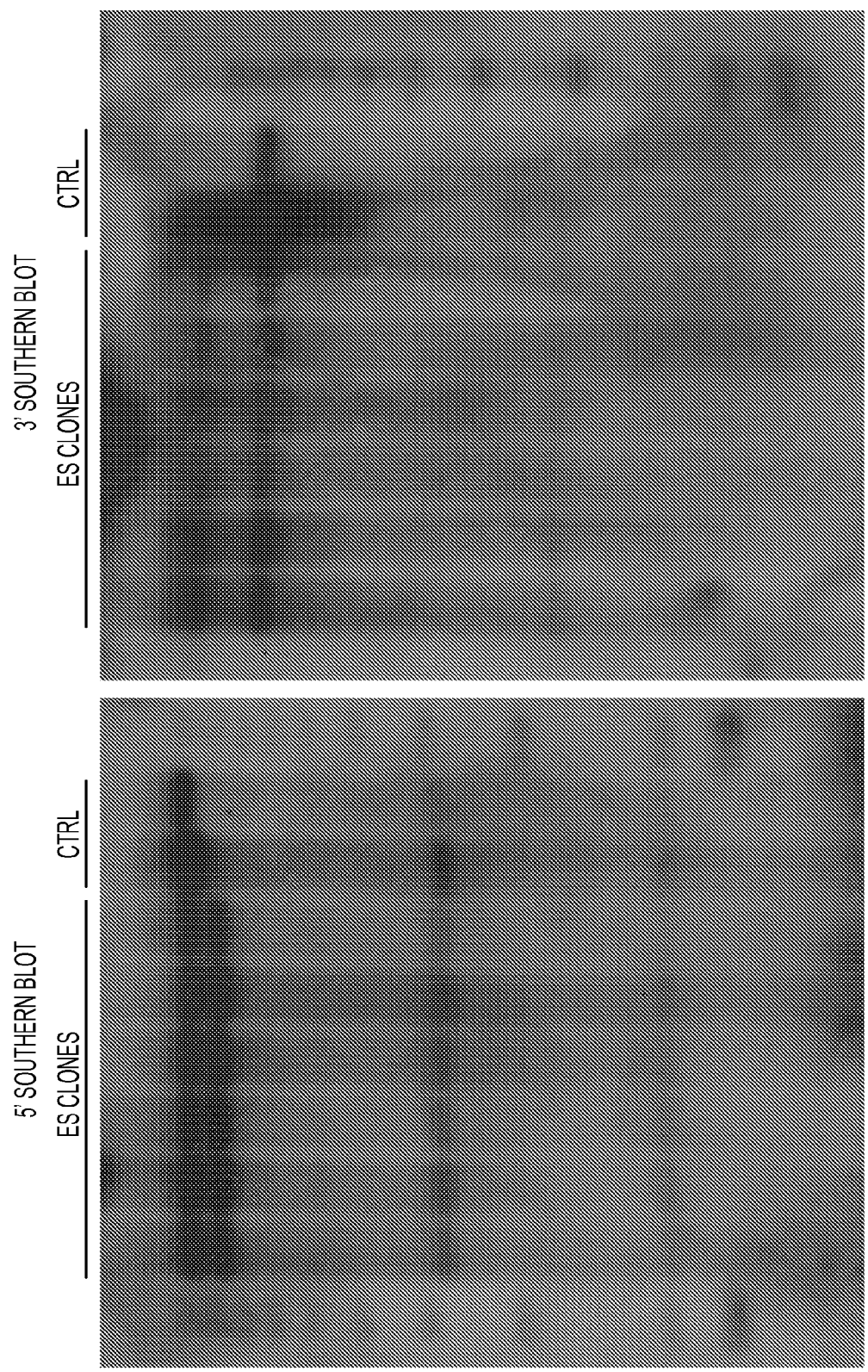
FIG. 26. ES cell lines with Gpr17 targeting allele. Southern blot showing 6 independent ES clones have Gpr17 conditional allele correctly targeted to the mouse genome at the 5' and 3' end. Control (Ctrl) is genomic DNA from wild type mice.

FIG. 25 is a schematic showing a Gpr17 conditional allele-targeting vector (purchased from KOMP) and FIG. 26 shows embryonic stem (ES) cell lines that express Gpr17 targeting allele. Southern blot showed 6 independent ES clones having the Gpr17 conditional allele correctly targeted to the mouse genome at the 5' and 3' end. Control (Ctrl) is genomic DNA from wild type mice. FIG. 26.

Figure 27:
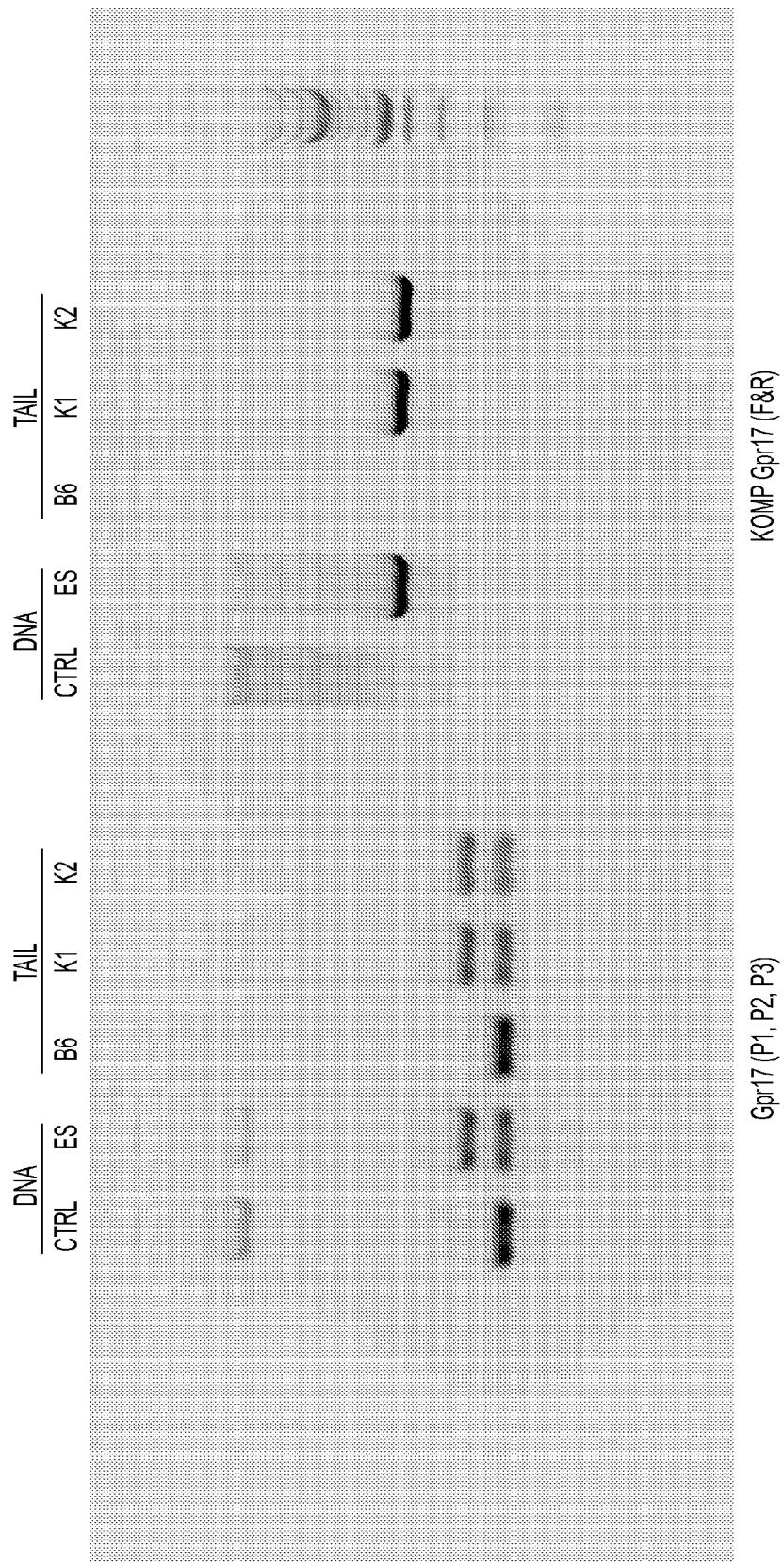
FIG. 27. Establishing genotyping PCR reactions for Gpr17 conditional allele in chimera mice ES clone with Gpr17 conditional allele was injected into mice. Genomic DNA was extracted from the tail of wild type (B6) and chimera mice (K1 & K2). Control DNA samples include: negative control (Ctrl, purified genomic DNA from wild type mice), and positive control (ES, purified DNA from ES clone with Gpr17 targeting allele).

Chimeric mice: In an experiment, an ES clone with a Gpr17 conditional allele was injected into female mice to create chimeric mice. Genomic DNA was extracted from the tail of both wild type (B6) and chimeric mice (K1 & K2). Control DNA samples included: a negative control (Ctrl, purified genomic DNA from wild type mice), and a positive control (ES, purified DNA from the ES clone with Gpr17 targeting allele). FIG. 27. This shows that the chimeric mice are suitable for making transgenic mice with a Gpr17 conditional allele. Indeed, we have bred the chimera with B6 mice and obtained progeny with germline transmission of the transgene-Gpr17 conditional allele. These results validate the feasibility of the transgenic mice and further establish a valid genotyping protocol for the subsequent genetic procedures.

The invention is illustrated herein by the experiments described above, which should not be construed as limiting. The contents of all references, pending patent applications and published patents, cited throughout this application are hereby expressly incorporated by reference. U.S. Provisional Application No. 61/591,909 and U.S. Provisional Application No. 61/646,544 are incorporated by reference herein. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

REFERENCES

Aponte, Y., Atasoy, D., and Sternson, S. M. (2011). AGRP neurons are sufficient to orchestrate feeding behavior rapidly and without training. Nature neuroscience 14, 351-355.

Balthasar, N., Coppari, R., McMinn, J., Liu, S. M., Lee, C. E., Tang, V., Kenny, C. D., McGovern, R. A., Chua, S. C., Jr., Elmquist, J. K., et al. (2004). Leptin receptor signaling in POMC neurons is required for normal body weight homeostasis. Neuron 42, 983-991.

Banks, A. S., Kon, N., Knight, C., Matsumoto, M., Gutierrez-Juarez, R., Rossetti, L., Gu, W., and Accili, D. (2008). SirT1 gain of function increases energy efficiency and prevents diabetes in mice. Cell Metab 8, 333-341.

Breen, T. L., Conwell, I. M., and Wardlaw, S. L. (2005). Effects of fasting, leptin, and insulin on AGRP and POMC peptide release in the hypothalamus. Brain Res 1032, 141-148.

Broberger, C., Johansen, J., Johansson, C., Schalling, M., and Hokfelt, T. (1998). The neuropeptide Y/agouti gene-related protein (AGRP) brain circuitry in normal, anorectic, and monosodium glutamate-treated mice. Proc Natl Acad Sci USA 95, 15043-15048.

Butler, A. A., and Kozak, L. P. (2010). A recurring problem with the analysis of energy expenditure in genetic models expressing lean and obese phenotypes. Diabetes 59, 323-329.

Chen, Y., Wu, H., Wang, S., Koito, H., Li, J., Ye, F., Hoang, J., Escobar, S. S., Gow, A., Arnett, H. A., et al. (2009). The oligodendrocyte-specific G protein-coupled receptor GPR17 is a cell-intrinsic timer of myelination. Nature neuroscience 12, 1398-1406.

Ciana, P., Fumagalli, M., Trincavelli, M. L., Verderio, C., Rosa, P., Lecca, D., Ferrario, S., Parravicini, C., Capra, V., Gelosa, P., et al. (2006). The orphan receptor GPR17 identified as a new dual uracil nucleotides/cysteinyl-leukotrienes receptor. Embo J 25, 4615-4627.

Cota, D., Proulx, K., Smith, K. A., Kozma, S. C., Thomas, G., Woods, S. C., and Seeley, R. J. (2006). Hypothalamic mTOR signaling regulates food intake. Science 312, 927-930.

Daniele, S., Trincavelli, M. L., Gabelloni, P., Lecca, D., Rosa, P., Abbracchio, M. P., and Martini, C. (2011). Agonist-induced desensitization/resensitization of human G protein-coupled receptor 17: a functional cross-talk between purinergic and cysteinyl-leukotriene ligands. The Journal of pharmacology and experimental therapeutics 338, 559-567.

Erlinge, D. (2011). P2Y receptors in health and disease. Adv Pharmacol 61, 417-439.

Ernst, M. B., Wunderlich, C. M., Hess, S., Paehler, M., Mesaros, A., Koralov, S. B., Kleinridders, A., Husch, A., Munzberg, H., Hampel, B., et al. (2009). Enhanced Stat3 activation in POMC neurons provokes negative feedback inhibition of leptin and insulin signaling in obesity. J Neurosci 29, 11582-11593.

Fischer, W., and Krugel, U. (2007). P2Y receptors: focus on structural, pharmacological and functional aspects in the brain. Curr Med Chem 14, 2429-2455.

Gautron, L., and Elmquist, J. K. (2011). Sixteen years and counting: an update on leptin in energy balance. The Journal of clinical investigation 121, 2087-2093.

Haeusler, R. A., Kaestner, K. H., and Accili, D. (2010). FoxOs function synergistically to promote glucose production. J Biol Chem 285, 35245-35248.

Halaas, J. L., Gajiwala, K. S., Maffei, M., Cohen, S. L., Chait, B. T., Rabinowitz, D., Lallone, R. L., Burley, S. K., and Friedman, J. M. (1995). Weight-reducing effects of the plasma protein encoded by the obese gene. Science 269, 543-546.

Hill, J. W., Elias, C. F., Fukuda, M., Williams, K. W., Berglund, E. D., Holland, W. L., Cho, Y. R., Chuang, J. C., Xu, Y., Choi, M., et al. (2010). Direct insulin and leptin action on pro-opiomelanocortin neurons is required for normal glucose homeostasis and fertility. Cell metabolism 11, 286-297.

Kastrati, A., and Ndrepepa, G. (2009). Cangrelor—a champion lost in translation? The New England journal of medicine 361, 2382-2384.

Kaushik, S., Rodriguez-Navarro, J. A., Arias, E., Kiffin, R., Sahu, S., Schwartz, G. J., Cuervo, A. M., and Singh, R. (2011). Autophagy in hypothalamic AgRP neurons regulates food intake and energy balance. Cell metabolism 14, 173-183.

Kim, M. S., Pak, Y. K., Jang, P. G., Namkoong, C., Choi, Y. S., Won, J. C., Kim, K. S., Kim, S. W., Kim, H. S., Park, J. Y., et al. (2006). Role of hypothalamic Foxo1 in the regulation of food intake and energy homeostasis. Nat Neurosci 9, 901-906.

Kitamura, T., Feng, Y., Kitamura, Y. I., Chua, S. C., Jr., Xu, A. W., Barsh, G. S., Rossetti, L., and Accili, D. (2006). Forkhead protein FoxO1 mediates Agrp-dependent effects of leptin on food intake. Nat Med 12, 534-540.

Konner, A. C., Janoschek, R., Plum, L., Jordan, S. D., Rother, E., Ma, X., Xu, C., Enriori, P., Hampel, B., Barsh, G. S., et al. (2007). Insulin Action in AgRP-Expressing Neurons Is Required for Suppression of Hepatic Glucose Production. Cell Metab 5, 438-449.

Krashes, M. J., Koda, S., Ye, C., Rogan, S. C., Adams, A. C., Cusher, D. S., Maratos-Flier, E., Roth, B. L., and Lowell, B. B. (2011). Rapid, reversible activation of AgRP neurons drives feeding behavior in mice. The Journal of clinical investigation 121, 1424-1428.

Lecca, D., Trincavelli, M. L., Gelosa, P., Sironi, L., Ciana, P., Fumagalli, M., Villa, G., Verderio, C., Grumelli, C., Guerrini, U., et al. (2008). The recently identified P2Y-like receptor GPR17 is a sensor of brain damage and a new target for brain repair. PLoS One 3, e3579.

Levine, A. S., Jewett, D. C., Cleary, J. P., Kotz, C. M., and Billington, C. J. (2004). Our journey with neuropeptide Y: effects on ingestive behaviors and energy expenditure. Peptides 25, 505-510.

Lewis, G. F., Uffelman, K. D., Szeto, L. W., Weller, B., and Steiner, G. (1995). Interaction between free fatty acids and insulin in the acute control of very low density lipoprotein production in humans. J Clin Invest 95, 158-166.

Lin, H. V., and Accili, D. (2011). Hormonal regulation of hepatic glucose production in health and disease. Cell metabolism 14, 9-19.

Liu, T., Kong, D., Shah, B. P., Ye, C., Koda, S., Saunders, A., Ding, J. B., Yang, Z., Sabatini, B. L., and Lowell, B. B. (2012). Fasting Activation of AgRP Neurons Requires NMDA Receptors and Involves Spinogenesis and Increased Excitatory Tone. Neuron 73, 511-522.

Luquet, S., Perez, F. A., Hnasko, T. S., and Palmiter, R. D. (2005). NPY/AgRP neurons are essential for feeding in adult mice but can be ablated in neonates. Science 310, 683-685.

Matsumoto, M., Pocai, A., Rossetti, L., Depinho, R. A., and Accili, D. (2007). Impaired regulation of hepatic glucose production in mice lacking the forkhead transcription factor Foxo1 in liver. Cell Metab 6, 208-216.

Mesaros, A., Koralov, S. B., Rother, E., Wunderlich, F. T., Ernst, M. B., Barsh, G. S., Rajewsky, K., and Bruning, J. C. (2008). Activation of Stat3 signaling in AgRP neurons promotes locomotor activity. Cell Metab 7, 236-248.

Nakae, J., Kitamura, T., Kitamura, Y., Biggs, W. H., 3rd, Arden, K. C., and Accili, D. (2003). The forkhead transcription factor Foxo1 regulates adipocyte differentiation. Dev Cell 4, 119-129.

Okamoto, H., Obici, S., Accili, D., and Rossetti, L. (2005). Restoration of liver insulin signaling in Insr knockout mice fails to normalize hepatic insulin action. J Clin Invest 115, 1314-1322.

Ollmann, M. M., Wilson, B. D., Yang, Y. K., Kerns, J. A., Chen, Y., Gantz, I., and Barsh, G. S. (1997). Antagonism of central melanocortin receptors in vitro and in vivo by agouti-related protein. Science 278, 135-138.

Padilla, S. L., Carmody, J. S., and Zeltser, L. M. (2010). Pomc-expressing progenitors give rise to antagonistic neuronal populations in hypothalamic feeding circuits. Nature medicine 16, 403-405.

Paik, J. H., Kollipara, R., Chu, G., Ji, H., Xiao, Y., Ding, Z., Miao, L., Tothova, Z., Horner, J. W., Carrasco, D. R., et al. (2007). FoxOs Are Lineage-Restricted Redundant Tumor Suppressors and Regulate Endothelial Cell Homeostasis. Cell 128, 309-323.

Pajvani, U. B., Shawber, C. J., Samuel, V. T., Birkenfeld, A. L., Shulman, G. I., Kitajewski, J., and Accili, D. (2011). Inhibition of Notch signaling ameliorates insulin resistance in a FoxO1-dependent manner. Nature medicine 17, 961-967.

Pinto, S., Roseberry, A. G., Liu, H., Diano, S., Shanabrough, M., Cai, X., Friedman, J. M., and Horvath, T. L. (2004). Rapid rewiring of arcuate nucleus feeding circuits by leptin. Science 304, 110-115.

Plum, L., Lin, H. V., Dutia, R., Tanaka, J., Aizawa, K. S., Matsumoto, M., Kim, A. J., Cawley, N. X., Paik, J. H., Loh, Y. P., et al. (2009). The obesity susceptibility gene Cpe links FoxO1 signaling in hypothalamic pro-opiomelanocortin neurons with regulation of food intake. Nat Med 15, 1195-1201.

Plum, L., Rother, E., Munzberg, H., Wunderlich, F. T., Morgan, D. A., Hampel, B., Shanabrough, M., Janoschek, R., Konner, A. C., Alber, J., et al. (2007). Enhanced Leptin-Stimulated Pi3k Activation in the CNS Promotes White Adipose Tissue Transdifferentiation. Cell Metab 6, 431-445.

Pugliese, A. M., Trincavelli, M. L., Lecca, D., Coppi, E., Fumagalli, M., Ferrario, S., Failli, P., Daniele, S., Martini, C., Pedata, F., et al. (2009). Functional characterization of two isoforms of the P2Y-like receptor GPR17: [35S]GTP-gammaS binding and electrophysiological studies in 1321N1 cells. American journal of physiology Cell physiology 297, C1028-1040.

Qian, S., Chen, H., Weingarth, D., Trumbauer, M. E., Novi, D. E., Guan, X., Yu, H., Shen, Z., Feng, Y., Frazier, E., et al. (2002). Neither agouti-related protein nor neuropeptide Y is critically required for the regulation of energy homeostasis in mice. Molecular and cellular biology 22, 5027-5035.

Rossi, M., Kim, M. S., Morgan, D. G., Small, C. J., Edwards, C. M., Sunter, D., Abusnana, S., Goldstone, A. P., Russell, S. H., Stanley, S. A., et al. (1998). A C-terminal fragment of Agouti-related protein increases feeding and antagonizes the effect of alpha-melanocyte stimulating hormone in vivo. Endocrinology 139, 4428-4431.

Schwartz, M. W., Woods, S. C., Seeley, R. J., Barsh, G. S., Baskin, D. G., and Leibel, R. L. (2003). Is the energy homeostasis system inherently biased toward weight gain? Diabetes 52, 232-238.

Shi, H., Strader, A. D., Sorrell, J. E., Chambers, J. B., Woods, S. C., and Seeley, R. J. (2008). Sexually different actions of leptin in proopiomelanocortin neurons to regulate glucose homeostasis. American journal of physiology Endocrinology and metabolism 294, E630-639.

Takahashi, K. A., and Cone, R. D. (2005). Fasting induces a large, leptin-dependent increase in the intrinsic action potential frequency of orexigenic arcuate nucleus neuropeptide Y/Agouti-related protein neurons. Endocrinology 146, 1043-1047.

Tong, Q., Ye, C. P., Jones, J. E., Elmquist, J. K., and Lowell, B. B. (2008). Synaptic release of GABA by AgRP neurons is required for normal regulation of energy balance. Nature neuroscience 11, 998-1000.

van de Wall, E., Leshan, R., Xu, A. W., Balthasar, N., Coppari, R., Liu, S. M., Jo, Y. H., MacKenzie, R. G., Allison, D. B., Dun, N. J., et al. (2008). Collective and individual functions of leptin receptor modulated neurons controlling metabolism and ingestion. Endocrinology 149, 1773-1785.

Wang, Y. C., McPherson, K., Marsh, T., Gortmaker, S. L., and Brown, M. (2011). Health and economic burden of the projected obesity trends in the USA and the UK. Lancet 378, 815-825.

Woods, S. C., Lotter, E. C., McKay, L. D., and Porte, D., Jr. (1979). Chronic intracerebroventricular infusion of insulin reduces food intake and body weight of baboons. Nature 282, 503-505.

Yang, Y., Atasoy, D., Su, H. H., and Sternson, S. M. (2011). Hunger States Switch a Flip-Flop Memory Circuit via a Synaptic AMPK-Dependent Positive Feedback Loop. Cell 146, 992-1003.

TABLE 1

Blood metabolite measurements

|  | Ad lib WT n = 5 KO n = 4 | 6 hr fast WT n = 7 KO n = 10 | 16 hr fast WT n = 7 KO n = 9 | 20 hr fast WT n = 6 KO n = 6 | 6 hr refed WT n = 8 KO n = 7 |
|---|---|---|---|---|---|
| Glucose (mg/dL) | 116 ± 4.85 <br> 98 ± 9.65 | 44 ± 2.72 <br> 46 ± 2.85 | 47 ± 5.47 <br> 43 ± 2.53 | 42 ± 2.20 <br> 40 ± 3.64 | 92 ± 3.31 <br> 88 ± 2.27 |
| Insulin (ng/ml) | 0.76 ± 0.04 <br> 0.66 ± 0.07 | 0.48 ± 0.06 <br> 0.51 ± 0.06 | 0.43 ± 0.04 <br> 0.39 ± 0.07 | 0.33 ± 0.02 <br> 0.31 ± 0.01 | 1.81 ± 0.36 <br> 3.06 ± 0.53 |
| Leptin (ng/ml) | 5.13 ± 1.11 <br> 3.12 ± 0.48 | 1.87 ± 1.18 <br> 0.63 ± 0.29 | 0.66 ± 0.30 <br> 0.16 ± 0.15 | NA <br> NA | 9.87 ± 1.62 <br> 4.67 ± 1.47 * |

NA: not measured;
* = P < 0.05.
We present data as means ± SEM.

TABLE 2

Pathway analysis following expression profiling of FoxO1-deficient flow-sorted AgRP neurons

| GO Term | Description | P-value | Enrichment |
|---|---|---|---|
| GO:0022900 | Electron transport chain | 2.99E−06 | 3.86 |
| GO:0006412 | Translation | 3.80E−06 | 2.70 |
| GO:0006091 | Generation of precursor metabolites and energy | 4.13E−04 | 2.31 |
| GO:0000002 | Mitochondrial genome maintenance | 4.47E−04 | 15.36 |
| GO:0044085 | Cellular component biogenesis | 7.82E−04 | 3.09 |

TABLE 3

Gene expression profiling (log value and ratio) of AgRP neurons from wild-type (WT) and Agrp-Foxo1$^{-/-}$ (KO) mice.

| Probe set | WT | KO | Ratio | Gene symbol |
|---|---|---|---|---|
| 6967593 | 7.334915 | 8.229675 | 1.8593 | Gabra5 |
| 7017520 | 8.65706 | 9.42809 | 1.7065 | Gabra3 |
| 6979181 | 8.497617 | 9.176637 | 1.6011 | Gabarapl2 |
| 6787525 | 7.742589 | 8.377478 | 1.5528 | Gabrg2 |
| 6938999 | 8.623663 | 9.2274 | 1.5196 | Gabrg1 |
| 6847659 | 6.851241 | 7.351151 | 1.4141 | Grik1 |
| 6939005 | 7.082098 | 7.476961 | 1.3148 | Gabra2 |
| 6780332 | 7.849636 | 8.18437 | 1.2611 | Gabrb2 |
| 6886732 | 8.106435 | 8.406344 | 1.2311 | Cacnb4 |
| 6950160 | 9.817965 | 10.10382 | 1.2191 | Gabarapl1 |
| 6780331 | 7.104427 | 7.38193 | 1.2121 | Gabrb2 |
| 6927253 | 6.520467 | 6.647771 | 1.0923 | Gabrd |
| 6967584 | 8.23948 | 8.27064 | 1.0218 | Gabrg3 |
| 6912521 | 5.155926 | 5.177533 | 1.0151 | Gabrr1 |
| 6787196 | 5.245202 | 5.213418 | 0.9782 | Gabrp |
| 6960885 | 11.26103 | 11.22604 | 0.9760 | Gabrb3 |
| 6912520 | 5.63561 | 5.597581 | 0.9740 | Gabrr2 |
| 7017513 | 10.52148 | 10.47368 | 0.9674 | Gabre |
| 6931512 | 8.54521 | 8.460707 | 0.9431 | Gabrb1 |
| 6787531 | 4.47922 | 4.384243 | 0.9363 | Gabra6 |
| 6939019 | 6.06497 | 5.963992 | 0.9324 | Gabra4 |
| 6850271 | 9.84164 | 9.657647 | 0.8803 | Gabbr1 |
| 6787527 | 7.194375 | 6.852592 | 0.7891 | Gabra1 |
| 6906261 | 9.807928 | 10.26532 | 1.3731 | Gria2 |
| 6993204 | 9.276702 | 9.324981 | 1.0340 | Gria4 |
| 7010835 | 7.83755 | 7.583404 | 0.8385 | Gria3 |
| 6781201 | 10.10458 | 9.628842 | 0.7191 | Gria1 |
| 6847659 | 6.851241 | 7.351151 | 1.4141 | Grik1 |
| 6994947 | 7.036166 | 7.030791 | 0.9963 | Grik4 |
| 6773802 | 8.190992 | 8.148666 | 0.9711 | Grik2 |
| 6965906 | 8.111919 | 7.581288 | 0.6923 | Grik5 |
| 6957715 | 7.906801 | 8.38035 | 1.3885 | Grin2b |
| 6843861 | 5.977024 | 6.374393 | 1.3171 | Grin2a |
| 6792418 | 6.543379 | 6.471032 | 0.9511 | Grin2c |

TABLE 3-continued

Gene expression profiling (log value and ratio) of AgRP neurons from wild-type (WT) and Agrp-Foxo1$^{-/-}$ (KO) mice.

| Probe set | WT | KO | Ratio | Gene symbol |
|---|---|---|---|---|
| 6769175 | 7.146412 | 7.049402 | 0.9350 | Grin3b |
| 6967014 | 7.233267 | 7.02848 | 0.8677 | Grin2d |
| 6885399 | 9.24327 | 8.866004 | 0.7699 | Grin1 |
| 6921569 | 5.16358 | 4.683928 | 0.7172 | Grin3a |
| 6839607 | 6.884823 | 6.909034 | 1.0169 | Abcc1 |
| 6839607 | 6.884823 | 6.909034 | 1.0169 | Abcc1 |
| 6950789 | 6.396797 | 6.375153 | 0.9851 | Abcc9 |
| 6967022 | 7.119905 | 7.033912 | 0.9421 | Abcc6 |
| 6844447 | 8.311327 | 8.217323 | 0.9369 | Abcc5 |
| 6869893 | 5.205484 | 5.077345 | 0.9150 | Abcc2 |
| 6855684 | 7.069956 | 6.889968 | 0.8827 | Abcc10 |
| 6958063 | 5.833824 | 5.586271 | 0.8423 | Abcc9 |
| 6790944 | 6.441928 | 6.176674 | 0.8321 | Abcc3 |
| 6983966 | 5.707139 | 5.402333 | 0.8096 | Abcc12 |
| 6816720 | 6.907582 | 8.140664 | 2.3507 | Kctd6 |
| 6870781 | 5.502103 | 6.067524 | 1.4798 | Kcnk18 |
| 6836305 | 7.314005 | 7.701155 | 1.3078 | Kcnq3 |
| 6803020 | 5.827271 | 6.205155 | 1.2994 | Kcnk10 |
| 6785133 | 6.505141 | 6.730864 | 1.1694 | Kctd2 |
| 6959116 | 6.374486 | 6.531417 | 1.1149 | Kcnn4 |
| 6820361 | 5.749503 | 5.885937 | 1.0992 | Kctd4 |
| 6967012 | 7.596197 | 7.70837 | 1.0809 | Kcnj14 |
| 6960456 | 7.665802 | 7.744672 | 1.0562 | Kcnc1 |
| 6837109 | 6.976925 | 7.043262 | 1.0471 | Kcnj4 |
| 6967026 | 5.610319 | 5.67602 | 1.0466 | Kcnj11 |
| 6960291 | 6.135087 | 6.190924 | 1.0395 | Kcnc3 |
| 6960457 | 7.117462 | 7.169259 | 1.0366 | Kcnc1 |
| 6867782 | 5.955575 | 6.002457 | 1.0330 | Kcnk7 |
| 6789358 | 6.187944 | 6.224165 | 1.0254 | Kctd11 |
| 6937986 | 8.765806 | 8.789629 | 1.0166 | Kcnip4 |
| 6848102 | 6.743556 | 6.752539 | 1.0062 | Kcnj6 |
| 6758310 | 5.469614 | 5.469614 | 1.0000 | Kctd18 |
| 6966448 | 6.64381 | 6.635556 | 0.9943 | Kctd15 |
| 6823284 | 7.673025 | 7.66258 | 0.9928 | Kcnma1 |
| 6987932 | 4.783345 | 4.770676 | 0.9913 | Kcnj1 |
| 6892888 | 7.187672 | 7.171233 | 0.9887 | Kcns1 |
| 6960370 | 6.290734 | 6.273255 | 0.9880 | Kcna7 |
| 6781492 | 6.625689 | 6.602062 | 0.9838 | Kcnj12 |
| 6974770 | 4.474943 | 4.444184 | 0.9789 | Kcnu1 |
| 6784844 | 4.555975 | 4.521375 | 0.9763 | Kcnj16 |
| 6765129 | 9.022768 | 8.971121 | 0.9648 | Kcnk2 |
| 6962759 | 6.009056 | 5.954184 | 0.9627 | Kctd14 |
| 6934657 | 6.264603 | 6.205727 | 0.9600 | Kctd7 |
| 6829687 | 8.220935 | 8.152759 | 0.9538 | Kcns2 |
| 6994423 | 6.003305 | 5.932381 | 0.9520 | Kcnj5 |
| 6965319 | 6.498583 | 6.4261 | 0.9510 | Kcnq1 |
| 6833153 | 7.360452 | 7.280484 | 0.9461 | Kcnh3 |
| 6887205 | 5.367066 | 5.276448 | 0.9391 | Kcnh7 |
| 6941202 | 7.059582 | 6.961515 | 0.9343 | Kctd10 |
| 6985813 | 7.520754 | 7.421107 | 0.9333 | Kcng4 |
| 6900277 | 8.040482 | 7.927094 | 0.9244 | Kcna3 |
| 6936719 | 7.09716 | 6.975229 | 0.9190 | Kcnh2 |
| 7009791 | 6.647227 | 6.51741 | 0.9139 | Kcnd1 |
| 6797383 | 5.982976 | 5.852443 | 0.9135 | Kcnk13 |
| 6782002 | 6.255998 | 6.123306 | 0.9121 | Kcnab3 |
| 6983232 | 6.907239 | 6.770917 | 0.9098 | Kcnn1 |
| 6843216 | 5.48262 | 5.312694 | 0.8889 | Kcne2 |
| 7020314 | 5.135297 | 4.958828 | 0.8849 | Kctd12b |
| 6755237 | 6.579461 | 6.39515 | 0.8801 | Kcnj10 |
| 6873368 | 6.778925 | 6.589808 | 0.8771 | Kcnip2 |
| 6798933 | 8.638136 | 8.447819 | 0.8764 | Kcns3 |
| 6962922 | 5.059389 | 4.866602 | 0.8749 | Kcne3 |
| 6858033 | 7.046924 | 6.830075 | 0.8604 | Kcnk12 |
| 6799239 | 7.988412 | 7.77102 | 0.8601 | Kcnf1 |
| 6784845 | 5.191991 | 4.971441 | 0.8582 | Kcnj2 |
| 6857763 | 5.104472 | 4.882034 | 0.8571 | Kcng3 |
| 6929622 | 8.186102 | 7.957447 | 0.8534 | Kcnk3 |
| 6860576 | 5.355231 | 5.12622 | 0.8532 | Kcnn2 |
| 6899254 | 8.649492 | 8.418308 | 0.8519 | Kcnn3 |
| 6750362 | 6.096981 | 5.863516 | 0.8506 | Kcne4 |
| 6984971 | 6.600798 | 6.365135 | 0.8493 | Kctd19 |
| 6927145 | 6.871956 | 6.632909 | 0.8473 | Kcnab2 |
| 6868902 | 6.081023 | 5.837927 | 0.8449 | Kcnv2 |
| 6779955 | 6.602043 | 6.351574 | 0.8406 | Kcnmb1 |
| 6979914 | 8.194757 | 7.943488 | 0.8402 | Kcnk1 |
| 6843419 | 6.646601 | 6.394507 | 0.8397 | Kcnj15 |
| 6957246 | 6.705725 | 6.421413 | 0.8211 | Kcna1 |
| 6900287 | 7.682659 | 7.386522 | 0.8144 | Kcna2 |
| 6801807 | 6.017248 | 5.718288 | 0.8128 | Kcnh5 |
| 6849581 | 8.281224 | 7.98038 | 0.8118 | Kctd20 |
| 6871264 | 7.622015 | 7.303193 | 0.8017 | Kcnk4 |
| 6823011 | 5.455785 | 5.13425 | 0.8002 | Kcnk5 |
| 6896557 | 6.159178 | 5.837061 | 0.7999 | Kcnmb2 |
| 6938947 | 7.307624 | 6.978423 | 0.7960 | Kctd8 |
| 6847948 | 6.585924 | 6.205316 | 0.7681 | Kcne1 |
| 7019865 | 8.397593 | 8.011468 | 0.7652 | Kcne1l |
| 6954648 | 10.53646 | 10.1488 | 0.7644 | Kcmf1 |
| 6890699 | 7.708419 | 7.317696 | 0.7627 | Kcnip3 |
| 6827123 | 8.753757 | 8.358816 | 0.7605 | Kctd12 |
| 6877229 | 7.820024 | 7.416324 | 0.7559 | Kcnj3 |
| 6958061 | 7.176657 | 6.76761 | 0.7531 | Kcnj8 |
| 6908029 | 7.280336 | 6.8413 | 0.7376 | Kcnc4 |
| 6900214 | 8.955211 | 8.507743 | 0.7333 | Kcnd3 |
| 6894265 | 7.643235 | 7.118929 | 0.6953 | Kcnq2 |
| 6765119 | 8.155873 | 7.630047 | 0.6946 | Kctd3 |
| 6879833 | 7.529752 | 6.988301 | 0.6871 | Kcna4 |
| 6764140 | 7.819049 | 7.218174 | 0.6594 | Kcnj9 |
| 6835454 | 6.749304 | 6.144689 | 0.6576 | Kcnv1 |
| 6898063 | 6.469952 | 5.822975 | 0.6386 | Kcnab1 |
| 6819957 | 6.932791 | 6.280385 | 0.6362 | Kctd9 |
| 6854314 | 7.764872 | 7.099676 | 0.6306 | Kctd5 |
| 6756419 | 6.593691 | 5.902424 | 0.6193 | Kcnh1 |
| 6787197 | 8.295441 | 7.57121 | 0.6053 | Kcnip1 |
| 6893131 | 7.722034 | 6.971058 | 0.5942 | Kcnb1 |
| 6777249 | 7.808446 | 7.012626 | 0.5760 | Kcnmb4 |
| 6944514 | 9.130609 | 8.333671 | 0.5756 | Kcnd2 |
| 6964256 | 8.706901 | 7.890445 | 0.5678 | Kctd13 |
| 6957240 | 8.08505 | 7.200551 | 0.5417 | Kcna5 |
| 6957248 | 8.06916 | 7.174156 | 0.5377 | Kcna6 |
| 6863582 | 8.294314 | 7.355973 | 0.5218 | Kctd1 |
| 6898721 | 4.240388 | 4.178139 | 0.9578 | Accn5 |
| 6750632 | 7.536539 | 7.434797 | 0.9319 | Accn4 |
| 6929300 | 6.523788 | 6.417257 | 0.9288 | Accn3 |
| 6833183 | 8.242703 | 7.457219 | 0.5802 | Accn2 |
| 6790135 | 9.334405 | 8.355479 | 0.5074 | Accn1 |
| 6763196 | 8.739561 | 9.28271 | 1.4572 | Cacna1e |
| 6886732 | 8.106435 | 8.406344 | 1.2311 | Cacnb4 |
| 6833100 | 7.775428 | 7.864439 | 1.0636 | Cacnb3 |
| 6790947 | 7.283747 | 7.331674 | 1.0338 | Cacna1g |
| 6854420 | 7.46104 | 7.413315 | 0.9675 | Cacna1h |
| 6885345 | 8.532759 | 8.479668 | 0.9639 | Cacna1b |
| 6753412 | 6.380148 | 6.278577 | 0.9320 | Cacna1s |
| 6875191 | 9.28346 | 9.174083 | 0.9270 | Cacnb2 |
| 7009773 | 6.365812 | 6.212637 | 0.8993 | Cacna1f |
| 6956902 | 8.028773 | 7.871789 | 0.8969 | Cacna1c |
| 6823659 | 8.278301 | 8.080484 | 0.8719 | Cacna1d |
| 6977751 | 8.395246 | 8.191644 | 0.8684 | Cacna1a |
| 6792019 | 6.543362 | 6.32517 | 0.8596 | Cacng1 |
| 6791233 | 7.695617 | 7.475136 | 0.8583 | Cacnb1 |
| 6836991 | 9.290387 | 8.999383 | 0.8173 | Cacng2 |
| 6792030 | 9.386881 | 9.066093 | 0.8006 | Cacng5 |
| 6823635 | 7.734582 | 7.409837 | 0.7984 | Cacna2d3 |
| 6928909 | 8.905806 | 8.575617 | 0.7954 | Cacna2d1 |
| 6992215 | 9.09226 | 8.616541 | 0.7191 | Cacna2d2 |
| 6792024 | 8.610157 | 7.927448 | 0.6230 | Cacng4 |
| 6807268 | 5.354183 | 5.536858 | 1.1350 | Catsper3 |
| 6890387 | 4.950604 | 4.907309 | 0.9704 | Catsper2 |
| 6966215 | 5.759496 | 5.672224 | 0.9413 | Catsperg2 |
| 6926005 | 6.379701 | 6.238837 | 0.9070 | Catsper4 |
| 6797453 | 3.801451 | 3.654016 | 0.9029 | Catsperb |
| 6867747 | 5.030708 | 4.83593 | 0.8737 | Catsper1 |
| 6966194 | 7.43607 | 6.80115 | 0.6440 | Catsperg2 |
| 6981342 | 5.547506 | 5.675637 | 1.0929 | Chrna6 |
| 6906846 | 7.026364 | 7.122074 | 1.0686 | Chrnb2 |
| 6789441 | 5.932626 | 5.983113 | 1.0356 | Chrne |
| 6751330 | 6.996738 | 7.04171 | 1.0317 | Chrng |
| 6967837 | 6.802946 | 6.839207 | 1.0255 | Chrna7 |
| 6889764 | 7.315837 | 7.317598 | 1.0012 | Chrm5 |
| 6819893 | 6.882961 | 6.882961 | 1.0000 | Chrna2 |
| 6887853 | 5.897502 | 5.790549 | 0.9285 | Chrna1 |

TABLE 3-continued

Gene expression profiling (log value and ratio) of AgRP neurons from wild-type (WT) and Agrp-Foxo1$^{-/-}$ (KO) mice.

| Probe set | WT | KO | Ratio | Gene symbol |
|---|---|---|---|---|
| 6974851 | 5.122431 | 5.008183 | 0.9239 | Chrnb3 |
| 6789343 | 5.887108 | 5.677177 | 0.8646 | Chrnb1 |
| 6995800 | 7.822301 | 7.594886 | 0.8542 | Chrnb4 |
| 6989238 | 4.464463 | 4.144917 | 0.8013 | Chrna5 |
| 6995799 | 5.994014 | 5.534096 | 0.7270 | Chrna3 |
| 6894253 | 7.794354 | 6.633564 | 0.4473 | Chrna4 |
| 6926864 | 8.070415 | 8.869244 | 1.7397 | Clcn6 |
| 6900409 | 7.05413 | 7.454255 | 1.3196 | Clcc1 |
| 6844480 | 7.247182 | 7.379725 | 1.0962 | Clcn2 |
| 7015375 | 8.792747 | 8.818684 | 1.0181 | Clcn5 |
| 6910129 | 4.950957 | 4.97547 | 1.0171 | Clca4 |
| 6910123 | 4.616422 | 4.553361 | 0.9572 | Clca1 |
| 6910137 | 5.314289 | 5.235714 | 0.9470 | Clca3 |
| 6910126 | 4.943043 | 4.833047 | 0.9266 | Clca2 |
| 6962773 | 9.439229 | 9.30075 | 0.9085 | Clns1a |
| 6945782 | 6.039642 | 5.894645 | 0.9044 | Clcn1 |
| 6926440 | 5.979173 | 5.819836 | 0.8954 | Clcnka |
| 6910133 | 5.225082 | 4.994046 | 0.8520 | Clca6 |
| 6850564 | 6.246818 | 6.014132 | 0.8510 | Clic5 |
| 6910142 | 4.672229 | 4.428946 | 0.8448 | Clca5 |
| 6850097 | 6.782398 | 6.533001 | 0.8412 | Clic1 |
| 6982786 | 9.579406 | 9.292712 | 0.8198 | Clcn3 |
| 6926443 | 6.757221 | 6.461262 | 0.8145 | Clcnkb |
| 6849342 | 7.02943 | 6.676212 | 0.7828 | Clcn7 |
| 6972505 | 7.869383 | 7.425797 | 0.7353 | Clcn4-2 |
| 6843244 | 5.687223 | 5.175894 | 0.7016 | Clic6 |
| 6926072 | 7.700567 | 6.497643 | 0.4344 | Clic4 |
| 6956852 | 7.797189 | 8.24886 | 1.3676 | Fxyd4 |
| 6988722 | 10.47938 | 10.50239 | 1.0161 | Fxyd6 |
| 6966337 | 6.596895 | 6.599205 | 1.0016 | Fxyd5 |
| 6966339 | 6.788862 | 6.788862 | 1.0000 | Fxyd1 |
| 6988728 | 6.545043 | 6.429797 | 0.9232 | Fxyd2 |
| 6966338 | 8.745025 | 8.59282 | 0.8999 | Fxyd7 |
| 6966343 | 5.771404 | 5.346621 | 0.7450 | Fxyd3 |
| 6948964 | 7.954214 | 8.468273 | 1.4281 | Grm7 |
| 6934119 | 5.560084 | 5.947661 | 1.3082 | Hvcn1 |
| 7015521 | 4.770474 | 5.032136 | 1.2849 | Cybb |
| 6924235 | 6.560891 | 6.772144 | 1.1577 | Bsnd |
| 6912018 | 4.888092 | 4.863471 | 0.9831 | Cngb3 |
| 6972473 | 5.98423 | 5.900929 | 0.9439 | Ano1 |
| 6748695 | 6.807873 | 6.651307 | 0.8972 | Cnga3 |
| 7011893 | 4.520422 | 4.353275 | 0.8906 | Cnga2 |
| 6998640 | 10.64992 | 10.42842 | 0.8577 | Gnai2 |
| 6769139 | 6.739503 | 6.472573 | 0.8311 | Hcn2 |
| 6995420 | 6.627321 | 6.332412 | 0.8151 | Htr3b |
| 6762234 | 7.631552 | 7.313537 | 0.8022 | Cntn2 |
| 6962502 | 10.18456 | 9.839222 | 0.7871 | Dlg2 |
| 6810563 | 8.16794 | 7.801076 | 0.7755 | Hcn1 |
| 6976233 | 5.026196 | 4.637506 | 0.7638 | Glra3 |
| 6784246 | 7.650186 | 7.179326 | 0.7215 | Cntnap1 |
| 6936140 | 5.778099 | 5.260024 | 0.6983 | Grm3 |
| 7020724 | 7.649497 | 6.728772 | 0.5282 | Glra2 |
| 6970749 | 4.773738 | 7.550964 | 6.8553 | Rps13 |
| 6990067 | 4.95818 | 6.528723 | 2.9702 | Rps27l |
| 6992950 | 6.429844 | 7.940375 | 2.8491 | Rpl14 |
| 6919296 | 8.541787 | 9.776727 | 2.3537 | Rps20 |
| 6785078 | 8.822414 | 9.993315 | 2.2515 | Rpl38 |
| 6909376 | 5.388285 | 6.401404 | 2.0183 | Rpl34 |
| 6831706 | 10.2321 | 11.04868 | 1.7612 | Rpl8 |
| 6969735 | 9.264075 | 10.0685 | 1.7464 | Rps3 |
| 6834865 | 7.79767 | 8.544039 | 1.6776 | Rpl30 |
| 6748841 | 8.416846 | 9.013694 | 1.5124 | Rpl31 |
| 6973282 | 11.44462 | 12.04055 | 1.5114 | Rpl5 |
| 6992920 | 7.653173 | 8.197017 | 1.4579 | Rpsa |
| 6861340 | 11.95621 | 12.40703 | 1.3668 | Rps14 |
| 6790500 | 8.098507 | 8.541962 | 1.3599 | Rps6kb1 |
| 6840603 | 6.983395 | 7.399116 | 1.3340 | Rpl35a |
| 6963012 | 3.840936 | 4.237166 | 1.3161 | Rpl31 |
| 6791222 | 8.997905 | 9.318871 | 1.2492 | Rpl23 |
| 6813317 | 7.841756 | 8.1499 | 1.2381 | Rps24 |
| 6970821 | 8.610354 | 8.907266 | 1.2285 | Rps15a |
| 6951200 | 8.623147 | 8.912549 | 1.2221 | Rps4y2 |
| 6855725 | 7.532882 | 7.802547 | 1.2055 | Rpl7l1 |
| 6837189 | 8.728898 | 8.970183 | 1.1820 | Rps19bp1 |
| 6781955 | 8.528721 | 8.756363 | 1.1709 | Rpl26 |
| 6988638 | 9.123616 | 9.310006 | 1.1379 | Rps25 |
| 6799645 | 5.229911 | 5.316449 | 1.0618 | Rps7 |
| 6972998 | 11.69396 | 11.77777 | 1.0598 | Rps9 |
| 6849543 | 6.682199 | 6.754283 | 1.0512 | Rpl10a |
| 6777287 | 6.339289 | 6.301088 | 0.9739 | Rps15 |
| 6935555 | 8.289394 | 8.229845 | 0.9596 | Rpl21 |
| 6849315 | 5.985846 | 5.773498 | 0.8631 | Rpl31 |
| 6933677 | 7.862966 | 7.628572 | 0.8500 | Rplp0 |
| 6992174 | 5.528226 | 5.275781 | 0.8395 | Rpl29 |
| 6839320 | 3.821193 | 3.541981 | 0.8240 | Rpl39l |
| 6985812 | 7.618377 | 7.322585 | 0.8146 | Rps13 |
| 6919017 | 9.471935 | 9.067886 | 0.7557 | Rpl22 |
| 6989868 | 7.553273 | 7.123382 | 0.7423 | Rpl4 |
| 6963364 | 10.79643 | 10.26698 | 0.6928 | Rpl27a |
| 6860430 | 8.288536 | 7.655913 | 0.6450 | Rpl21 |
| 6924833 | 8.74034 | 8.028321 | 0.6105 | Rps8 |
| 6959161 | 7.578933 | 6.733189 | 0.5564 | Rps19 |
| 6828417 | 8.28103 | 6.528413 | 0.2968 | Rpl37 |
| 6970155 | 6.035659 | 8.814373 | 6.8624 | Mrpl17 |
| 6811140 | 5.352678 | 6.764998 | 2.6616 | Mrpl32 |
| 6903095 | 7.312938 | 8.410316 | 2.1397 | Mrps28 |
| 6847517 | 8.292976 | 9.380087 | 2.1245 | Mrpl39 |
| 6932878 | 9.354049 | 10.41669 | 2.0888 | Mrps18c |
| 6949853 | 6.025676 | 7.056403 | 2.0431 | Mrpl51 |
| 6835806 | 6.396913 | 7.39868 | 2.0025 | Mrpl13 |
| 6932598 | 5.960342 | 6.83689 | 1.8360 | Mrpl1 |
| 6955604 | 6.648792 | 7.454556 | 1.7481 | Mrps25 |
| 6885353 | 9.096296 | 9.757523 | 1.5814 | Mrpl41 |
| 6921559 | 8.13278 | 8.787737 | 1.5746 | Mrpl50 |
| 6977073 | 8.528312 | 9.167829 | 1.5578 | Mrpl34 |
| 6843207 | 8.324337 | 8.957569 | 1.5510 | Mrps6 |
| 6850661 | 8.348651 | 8.964278 | 1.5322 | Mrpl14 |
| 6809447 | 6.145016 | 6.733224 | 1.5034 | Mrps27 |
| 6754476 | 8.153103 | 8.734402 | 1.4962 | Mrps14 |
| 6844362 | 6.455678 | 6.999997 | 1.4583 | Mrpl40 |
| 6899029 | 9.859091 | 10.37628 | 1.4312 | Mrpl24 |
| 6867706 | 9.050636 | 9.52491 | 1.3892 | Mrpl11 |
| 6917124 | 8.878555 | 9.344883 | 1.3816 | Mrps15 |
| 6954584 | 7.960523 | 8.395581 | 1.3520 | Mrpl35 |
| 6919184 | 7.26353 | 7.682282 | 1.3368 | Mrpl20 |
| 6871177 | 8.507818 | 8.921099 | 1.3317 | Mrpl49 |
| 6961889 | 7.787746 | 8.140642 | 1.2771 | Mrps11 |
| 6867565 | 6.607678 | 6.958776 | 1.2755 | Mrpl21 |
| 6785441 | 8.699657 | 9.01288 | 1.2425 | Mrpl12 |
| 6783367 | 6.812157 | 7.114583 | 1.2332 | Mrps3 |
| 6850678 | 9.36124 | 9.647982 | 1.2199 | Mrps18a |
| 6775449 | 8.349211 | 8.619127 | 1.2057 | Mrpl54 |
| 6934631 | 8.092247 | 8.347298 | 1.1934 | Mrps17 |
| 6929713 | 8.370893 | 8.622998 | 1.1909 | Mrpl33 |
| 6951121 | 6.041161 | 6.290709 | 1.1888 | Mrps35 |
| 6850780 | 7.432817 | 7.676719 | 1.1842 | Mrps10 |
| 6968647 | 8.692122 | 8.920585 | 1.1716 | Mrpl46 |
| 6785742 | 9.001454 | 9.225364 | 1.1679 | Mrps42 |
| 6954935 | 7.554811 | 7.772572 | 1.1629 | Mrpl19 |
| 6966164 | 10.43736 | 10.64041 | 1.1511 | Mrps12 |
| 6849326 | 8.087709 | 8.265957 | 1.1315 | Mrps34 |
| 6924281 | 8.029355 | 8.207158 | 1.1312 | Mrpl37 |
| 6808209 | 7.152382 | 7.32373 | 1.1261 | Mrpl36 |
| 6992093 | 7.579606 | 7.7317 | 1.1112 | Mrpl3 |
| 6849433 | 7.879142 | 8.015533 | 1.0992 | Mrpl28 |
| 6748729 | 9.360878 | 9.47761 | 1.0843 | Mrpl30 |
| 6785148 | 7.890301 | 7.984417 | 1.0674 | Mrps7 |
| 6749009 | 7.556159 | 7.646928 | 1.0649 | Mrps9 |
| 6904074 | 7.079347 | 7.164521 | 1.0608 | Mrpl47 |
| 6819425 | 8.526014 | 8.598465 | 1.0515 | Mrp63 |
| 6899519 | 7.825697 | 7.891083 | 1.0464 | Mrpl9 |
| 6783909 | 6.486808 | 6.528283 | 1.0292 | Mrpl45 |
| 6783884 | 8.169281 | 8.191765 | 1.0157 | Mrpl10 |
| 6875961 | 8.200056 | 8.205725 | 1.0039 | Mrps2 |
| 6923155 | 3.504194 | 3.503824 | 0.9997 | Mrpl48 |
| 6819152 | 8.626955 | 8.621492 | 0.9962 | Mrpl52 |
| 6792497 | 6.946844 | 6.903034 | 0.9701 | Mrpl38 |
| 6823059 | 9.113974 | 9.050158 | 0.9567 | Mrps16 |
| 6816371 | 6.394837 | 6.325842 | 0.9533 | Mrps30 |
| 6781247 | 7.58606 | 7.505204 | 0.9455 | Mrpl22 |

TABLE 3-continued

Gene expression profiling (log value and ratio) of AgRP neurons from wild-type (WT) and Agrp-Foxo1$^{-/-}$ (KO) mice.

| Probe set | WT | KO | Ratio | Gene symbol |
|---|---|---|---|---|
| 6998165 | 7.708451 | 7.597955 | 0.9263 | Mrps22 |
| 6987348 | 7.877725 | 7.751063 | 0.9159 | Mrpl4 |
| 6868128 | 8.883749 | 8.752434 | 0.9130 | Mrpl16 |
| 6881008 | 7.967422 | 7.800491 | 0.8907 | Mrps5 |
| 6815551 | 8.815508 | 8.590834 | 0.8558 | Mrps36 |
| 6969811 | 8.255061 | 8.011483 | 0.8446 | Mrpl48 |
| 6781321 | 8.965443 | 8.624922 | 0.7898 | Mrpl55 |
| 6974619 | 9.13947 | 8.793584 | 0.7868 | Mrps31 |
| 6855145 | 7.36724 | 6.952289 | 0.7500 | Mrps18b |
| 6756625 | 7.925919 | 7.505145 | 0.7470 | Mrpl15 |
| 6850711 | 8.044054 | 7.604998 | 0.7376 | Mrpl2 |
| 6881204 | 9.540852 | 9.037279 | 0.7054 | Mrps26 |
| 6873307 | 7.659211 | 7.063057 | 0.6615 | Mrpl43 |

The invention claimed is:

1. A method, comprising
   (a) providing a cell that overexpresses Gpr17,
   (b) determining a first level of pSTAT3 in the cell,
   (c) contacting the cell with a test compound under conditions and for a time sufficient to allow the test compound to interact with Gpr17, and for a time sufficient to allow for pSTAT3 levels in the cell to change in response to the effect of an interaction of the test compound with Grp17,
   (d) determining a second level of pSTAT3 in the test cell at a predetermined time after contact with the test compound,
   (e) comparing the first and second levels of pSTAT3, and
   (f) if the second level is significantly higher compared to the first level, then identifying the test compound as a Gpr17 antagonist useful for treatment of obesity or diabetes or impaired glucose tolerance; and if the second level is significantly lower compared lower than the first level, then identifying the test compound as a Gpr17 agonist useful for treatment of anorexia.

2. The method of claim 1, wherein the pSTAT3 level is determined using Fluorescence-activated cell sorting or luciferase reporter system.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
aactgtaccg ggagaaggcc                                               20

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA

<400> SEQUENCE: 2
gggatcacaa gtcaggcac                                                19

<210> SEQ ID NO 3
<211> LENGTH: 97
<212> TYPE: DNA
<213> ORGANISM: Artificial Sequence
<220> FEATURE:
<223> OTHER INFORMATION: Synthetic siRNA

<400> SEQUENCE: 3
tgctgttgac agtgagcgct cagtctatgt gcttcactac tagtgaagcc acagatgtag    60
tagtgaagca catagactga atgcctactg cctcgga                            97

<210> SEQ ID NO 4
<211> LENGTH: 97
<212> TYPE: DNA
<213> ORGANISM: Artificial Sequence
<220> FEATURE:
<223> OTHER INFORMATION: Synthetic siRNA

<400> SEQUENCE: 4
tgctgttgac agtgagcgac cacagacagt gcagaccaac tagtgaagcc acagatgtag    60
ttggtctgca ctgtctgtgg gtgcctactg cctcgga                            97

<210> SEQ ID NO 5
<211> LENGTH: 97
<212> TYPE: DNA
<213> ORGANISM: Artificial Sequence
<220> FEATURE:
<223> OTHER INFORMATION: Synthetic siRNA
```

<400> SEQUENCE: 5
tgctgttgac agtgagcgac tcttctatct gaacatgtat tagtgaagcc acagatgtaa    60
tacatgttca gatagaagag gtgcctactg cctcgga    97

<210> SEQ ID NO 6
<211> LENGTH: 97
<212> TYPE: DNA
<213> ORGANISM: Artificial Sequence
<220> FEATURE:
<223> OTHER INFORMATION: Synthetic siRNA

<400> SEQUENCE: 6
tgctgttgac agtgagcgat ggcttcctct tctatctgaa tagtgaagcc acagatgtat    60
tcagatagaa gaggaagcca gtgcctactg cctcgga    97

<210> SEQ ID NO 7
<211> LENGTH: 97
<212> TYPE: DNA
<213> ORGANISM: Artificial Sequence
<220> FEATURE:
<223> OTHER INFORMATION: Synthetic siRNA

<400> SEQUENCE: 7
tgctgttgac agtgagcgcc cggatcacct cctgcctcac tagtgaagcc acagatgtag    60
tgaggcagga ggtgatccgg ttgcctactg cctcgga    97

<210> SEQ ID NO 8
<211> LENGTH: 97
<212> TYPE: DNA
<213> ORGANISM: Artificial Sequence
<220> FEATURE:
<223> OTHER INFORMATION: Synthetic siRNA

<400> SEQUENCE: 8
tgctgttgac agtgagcgcg ttgtctgcct gcaactgtac tagtgaagcc acagatgtag    60
tacagttgca ggcagacaac ttgcctactg cctcgga    97

<210> SEQ ID NO 9
<211> LENGTH: 67
<212> TYPE: DNA
<213> ORGANISM: Artificial Sequence
<220> FEATURE:
<223> OTHER INFORMATION: Synthetic siRNA

<400> SEQUENCE: 9
tgctgttgac agtgagcgaa actgtaccgg gagaaggcct tagtgaagcc acagatgtaa    60
ggccttc    67

<210> SEQ ID NO 10
<211> LENGTH: 25
<212> TYPE: DNA
<213> ORGANISM: Artificial Sequence
<220> FEATURE:
<223> OTHER INFORMATION: Synthetic DNA

<400> SEQUENCE: 10
ccacacagct tatgtagcat tgagg    25

<210> SEQ ID NO 11
<211> LENGTH: 24
<212> TYPE: DNA
<213> ORGANISM: Artificial Sequence

```
<220> FEATURE:
<223> OTHER INFORMATION: Synthetic DNA

<400> SEQUENCE: 11
agcaggaagg tctcagtaac tccc                                              24
```